US011788053B2

(12) United States Patent
Wong et al.

(10) Patent No.: US 11,788,053 B2
(45) Date of Patent: Oct. 17, 2023

(54) MICROORGANISMS AND METHODS FOR REDUCING BACTERIAL CONTAMINATION

(71) Applicant: Melio Peptide Systems Inc., Vancouver (CA)

(72) Inventors: Steve Good-Sung Wong, Vancouver (CA); Hendrik Jurgens Jansen Van Vuuren, Brentwood Bay (CA)

(73) Assignee: Melio Peptide Systems Inc., Vancouver (CA)

(*) Notice: Subject to any disclaimer, the term of this patent is extended or adjusted under 35 U.S.C. 154(b) by 243 days.

(21) Appl. No.: 17/347,413

(22) Filed: Jun. 14, 2021

(65) Prior Publication Data

US 2021/0388311 A1     Dec. 16, 2021

Related U.S. Application Data

(60) Provisional application No. 63/039,238, filed on Jun. 15, 2020.

(51) Int. Cl.
| *A61K 35/646* | (2015.01) |
| *A61K 39/00* | (2006.01) |
| *C07K 14/435* | (2006.01) |
| *C12N 1/16* | (2006.01) |

(52) U.S. Cl.
CPC ............. *C12N 1/16* (2013.01); *A61K 35/646* (2013.01); *A61K 39/0003* (2013.01); *C07K 14/43527* (2013.01)

(58) Field of Classification Search
None
See application file for complete search history.

(56) References Cited

U.S. PATENT DOCUMENTS

| 4,368,268 | A  | 1/1983  | Gong |
| 5,965,408 | A  | 10/1999 | Short |
| 6,582,944 | B1 | 6/2003  | Hallborn et al. |
| 7,226,735 | B2 | 6/2007  | Jeffries et al. |
| 7,985,567 | B2 | 7/2011  | Chou et al. |
| 8,071,298 | B2 | 12/2011 | Abbas et al. |
| 8,114,641 | B2 | 2/2012  | Picataggio et al. |
| 8,530,226 | B2 | 9/2013  | Festel et al. |
| 8,900,841 | B2 | 12/2014 | Medoff et al. |
| 8,975,049 | B2 | 3/2015  | Liao et al. |
| 9,068,204 | B2 | 6/2015  | Donovan et al. |
| 9,333,227 | B2 | 5/2016  | Gabant |
| 10,188,114 | B2 | 1/2019  | Gabant |
| 10,435,721 | B2 | 10/2019 | Luo et al. |
| 2004/0142456 | A1 | 7/2004 | Jeffries et al. |
| 2004/0231661 | A1 | 11/2004 | Griffin et al. |
| 2005/0153411 | A1 | 7/2005 | Wahlbom et al. |
| 2006/0234364 | A1 | 10/2006 | Rajgarhia et al. |
| 2009/0047719 | A1 | 2/2009 | Burgard et al. |
| 2009/0104157 | A1 | 4/2009 | Solomon et al. |
| 2010/0330041 | A1 | 12/2010 | Bayrock |
| 2013/0035515 | A1 | 2/2013 | Dobson et al. |
| 2014/0148379 | A1 | 5/2014 | Liu et al. |
| 2015/0056253 | A1* | 2/2015 | Bancel ............... A61K 38/1729 424/278.1 |
| 2015/0320829 | A1 | 11/2015 | Liu et al. |
| 2018/0087073 | A1 | 3/2018 | Steele et al. |

FOREIGN PATENT DOCUMENTS

| JP | 2018-016548 A | 2/2018 |
| WO | WO 2007/050671 A2 | 5/2007 |
| WO | WO 2008/098227 A2 | 8/2008 |
| WO | WO 2009/103533 A1 | 9/2008 |
| WO | WO 2011/153144 A1 | 12/2011 |
| WO | WO 2012/011962 A2 | 1/2012 |
| WO | WO 2012/017365 A1 | 2/2012 |
| WO | WO 2013/178699 A1 | 12/2013 |
| WO | WO 2018/156998 A1 | 8/2018 |

OTHER PUBLICATIONS

Saito et al., "Identification and characterization of antimicrobial peptide, defensin, in the taiga tick, Ixodes persulcatus," *Insect Mol. Biol.*, 18(4):531-539 (2009).
Ahmad et al., "Enhancement of xylitol production in Candida tropicalis by co-expression of two genes involved in pentose phosphate pathway," *Bioprocess Biosyst. Eng.*, 35:199-204 (2012).
Ahmad et al., "Enhancement of xylitol production in glycerol kinase disrupted Candida tropicalis by co-expression of three genes involved in glycerol metabolic pathway," *Bioprocess Biosyst. Eng.*, 36(9):1279-1284 (2013).
Arnold et al., "Optimizing industrial enzymes by directed evolution," *Adv. Biochem. Eng. Biotechnol.*, 58:1-14 (1997).
Avalos et al., "Compartmentalization of metabolic pathways in yeast mitochondria improves the production of branched-chain alcohols," *Nat. Biotechnol.*, 31(4):335-341 (2013).
Barbosa et al., "Screening of yeasts for production of xylitol fromD-xylose and some factors which affect xylitol yield in Candida guilliermondii," *J. Ind. Microbiol.*, 3(4):241-251 (1988).
Barrero et al., "An improved secretion signal enhances the secretion of model proteins from Pichia pastoris," *Microb. Cell Fact.*, 17:161 (2018).
Beckner et al., "Microbial contamination of fuel ethanol fermentations," *Lett. Appl. Microbiol.*, 53(4):387-394 (2011).
Bertozzi Silva et al., "Bacteriophages as antimicrobial agents against bacterial contaminants in yeast fermentation processes," *Biotechnol. Biofuels* 7:123 (2014).

(Continued)

*Primary Examiner* — S. Devi

(74) *Attorney, Agent, or Firm* — Greenberg Traurig LLP

(57) ABSTRACT

Provided herein are compositions and methods for reducing bacterial contamination during cell culture. Such compositions and methods utilize engineered peptides or recombinant cells capable of secreting such peptides into culture medium. Also provided are methods of using the engineered peptides for inhibiting bacterial growth during culturing of cells.

14 Claims, 35 Drawing Sheets

Specification includes a Sequence Listing.

(56) References Cited

OTHER PUBLICATIONS

Bhandiwad et al., "Metabolic engineering of Thermoanaerobacterium saccharolyticum for n-butanol production," *Metab. Eng.*, 21:17-25 (2014).
Bischoff et al., "Modeling bacterial contamination of fuel ethanol fermentation," *Biotechnol. Bioeng.*, 103(1):117-122 (2009).
Brat et al., "Isobutanol production from D-xylose by recombinant *Saccharomyces cerevisiae*," *FEMS Yeast Res.*, 13(2):241-244 (2013).
Bura et al., "Novel endophytic yeast Rhodotorula mucilaginosa strain PTD3 I: production of xylitol and ethanol," *J. Ind. Microbiol. Biotechnol.*, 39:1003-1011 (2012).
Cadete et al., "*Cyberlindnera xylosilytica* sp. nov., a xylitol-producing yeast species isolated from lignocellulosic materials," *Int. J. Syst. Evolv. Microbiol.*, 65(9):2968-2974 (2015).
Ceccato-Antonini, "Conventional and nonconventional strategies for controlling bacterial contamination in fuel ethanol fermentations," *World J. Microbiol. Biotechnol.*, 34:1-11 (2018).
Cheng et al., "Genetically engineered Pichia pastoris yeast for conversion of glucose to xylitol by a single-fermentation process," *Appl. Microbiol. Biotechnol.*, 98(8):3539-3552 (2014).
Cheng et al., "Xylitol production from xylose mother liquor: a novel strategy that combines the use of recombinant Bacillus subtilis and Candida maltose," *Microbial. Cell Fact.*, 10:5 (2011).
Chin et al., "Codon Optimization OnLine (COOL): a web-based multi-objective optimization platform for synthetic gene design," *Bioinformatics*, 30(15):2210-2212 (2014).
Chung et al., "Computational codon optimization of synthetic gene for protein expression," *BMC Syst Biol.*, 6:134 (2012).
Chung et al., "Stable expression of xylose reductase gene enhances xylitol production in recombinant *Saccharomyces cerevisiae*," *Enzyme Microb. Technol.*, 30:809-816 (2002).
Crameri et al., "DNA shuffling of a family of genes from diverse species accelerates directed evolution," *Nature*, 391:288-291 (1998).
Dahabieh et al., "Functional expression of the DUR3 gene in a wine yeast strain to minimize ethyl carbamate in Chardonnay wine," *J. Enol. Vitic.*, 60(4):537-541 (2009).
Dahiya et al., "Xylitol production from sugar cane bagasse by fermentation," *Modernization of Indian Sugar Industry*, Gehlawat ed., New Delhi, India, pp. 292-303 (1990).
De Man et al., "A medium for the cultivation of lactobacilli," *J. Appl. Bact.* 23:130-135 (1960).
Dellomonaco et al., "Engineered reversal of the β-oxidation cycle for the synthesis of fuels and chemicals," *Nature*, 10:476(7360):355-359 (2011).
Felpeto-Santero et al., "Engineering alternative isobutanol production platforms," *AMB Express*, 5(1):119 (2015).
Fenton et al., "Recombinant bacteriophage lysins as antibacterials," *Bioeng. Bugs*, 1:9-16 (2010).
Fitzgerald et al., "Secretion of a foreign protein from budding yeasts is enhanced by cotranslational translocation and by suppression of vacuolar targeting," *Microb. Cell Fact.*, 13(1):125 (2014).
Fleet, "Wine yeasts for the future," *FEMS Yeast Res.*, 8(7):979-995 (2008).
Gibson et al., "New yeasts-new brews: modern approaches to brewing yeast design and development," *FEMS Yeast Res.*, 17(4):fox038 (2017).
Gietz et al., "Large-scale high-efficiency yeast transformation using the LiAc/SS carrier DNA/PEG method," *Nat. Protoc.*, 2(1):38-41 (2007).
Giovinden et al., "Xylitol production by recombinant *Saccharomyces cerevisiae* expressing the Pichia stipitis and Candida shehatae XYLI genes," *Appl. Microbiol. Biotechnol.*, 55(1):76-80 (2001).
GNügge et al., "*Saccharomyces cerevisiae* Shuttle vectors," *Yeast*, 34(5):205-221 (2017).
Gong et al., "Conversion of pentoses by yeasts," *Biotechnol. Bioeng.*, 25(1):85-102 (1983).
Gong et al., "Quantitative production of xylitol from D-xylose by a high-xylitol producing yeast mutant Candida tropicalis HXP2," *Biotechnol. Lett.*, 3(3):130-135 (1981).
Guaman-Burneo et al., "Xylitol production by yeasts isolated from rotting wood in the Galápagos Islands, Ecuador, and description of *Cyberlindnera galapagoensis f.a.*, sp. Nov," *Antonie Van Leeuwenhoek*, 108(4):919-931 (2015).
Guex et al., "Automated comparative protein structure modeling with SWISS-MODEL and Swiss-PdbViewer: A historical perspective," *Electrophoresis*, S162-S173 (2009). doi: 10.1002/elps.200900140.
Guirimand et al., "Cell surface engineering of *Saccharomyces cerevisiae* combined with membrane separation technology for xylitol production from rice straw hydrolysate," *Appl. Microbiol. Biotechnol.*, 100(8):3477-3487 (2016).
Hallborn et al., "The influence of cosubstrate and aeration on xylitol formation by recombinant *Saccharomyces cerevisiae* expressing the XYLI gene," *Appl. Microbiol. Biotechol.* 42:326-333 (1994).
Hallborn et al., "Xylitol production by recombinant *Saccharomyces cerevisiae*," *Biotechnology*, 9(11):1090-1095 (1991).
Hammami et al., "BACTIBASE second release: a database and tool platform for bacteriocin characterization," *BMC Microbiol.*, 10:22 (2010).
Hanai et al., "Engineered synthetic pathway for isopropanol production in *Escherichia coli*," *Appl. Environ. Microbiol.*, 73(24):7814-7818 (2007).
Hellinga, "Computational protein engineering," *Nat. Struct. Biol.*, 5(7):525-527 (1998).
Higashide et al., "Metabolic engineering of Clostridium cellulolyticum for production of isobutanol from cellulose," *Appl. Environ. Microb.*, 77(8):2727-2733 (2011).
Isogai et al., "Tertiary structure-related activity of tick defensin (persulcatusin) in the taiga tick, Ixodes persulcatus," *Exp. Appl. Acarol.* 53:71-77 (2011).
Jeffries et al., "Metabolic engineering for improved fermentation of pentoses by yeasts," *Appl. Microbiol. Biotechnol.*, 63(5):495-509 (2004).
Jeon et al., "Effect of heterologous xylose transporter expression in Candida tropicalis on xylitol production rate," *Bioprocess Biosyst. Eng.*, 36(6):809-817 (2013).
Jeon et al., "Xylitol production is increased by expression of codon-optimized Neurospora crassa xylose reductase gene in Candida tropicalis," *Bioprocess Biosyst. Eng.*, 35:191-198 (2012).
Jin et al., "*Saccharomyces cerevisiae* engineered for xylose metabolism exhibits a respiratory response," *App. Environ. Microbiol.*, 70(11):6816-6825 (2004).
Jin et al., "Stoichiometric network constraints on xylose metabolism by recombinant *Saccharomyces cerevisiae*," *Metab. Eng.*, 6(3):229-238 (2004).
Jo et al., "Dual utilization of NADPH and NADH cofactors enhances xylitol production in engineered *Saccharomyces cerevisiae*," *Biotechnol. J.*, 10(12):1935-1943 (2015).
Junyapate et al., "*Yamadazyma ubonensis f.a.*, sp. nov., a novel xylitol-producing yeast species isolated in Thailand," *Antonie Van Leeuwenhoek*, 105(3):471-480 (2014).
Kamat et al., "Xylitol production by Cyberlindnera (Williopsis) saturnus, a tropical mangrove yeast from xylose and corn cob hydrolysate," *J. App. Microbiol.*, 115(6):1357-1367 (2013).
Khatibi et al., "*Saccharomyces cerevisiae* expressing bacteriophage endolysins reduce Lactobacillus contamination during fermentation," *Biotechnol. Biofuels* 7: 104 (2014).
Kim et al., "Metabolic engineering of *Saccharomyces cerevisiae* for the production of 2-phenylethanol via Ehrlich pathway," *Biotechnol. Bioeng.*, 111(1):115-124 (2014).
Kim et al., "Yeast derived lysA2 can control bacterial contamination in ethanol fermentation," *Viruses* 10:281 (2018).
Klyachko et al., "Distiller yeasts producing antibacterial peptides," *Appl. Biochem. Microbiol.*, 51(5):585-590 (2015).
Ko et al., "Enhancement of xylitol productivity and yield using a xylitol dehydrogenase gene-disrupted mutant of Candida tropicalis under fully aerobic conditions," *Biotechnol. Lett.*, 28(15):1159-1162 (2006).
Ko et al., "Production of xylitol from D-xylose by a xylitol dehydrogenase gene-disrupted mutant of Candida tropicalis," *Appl. Environ. Microbiol.*, 72(6):4207-4213 (2006).

(56) References Cited

OTHER PUBLICATIONS

Kordowska-Wiater, "Production of arabitol by yeasts: current status and future prospects," *J. Appl. Microbiol.*, 119(2):303-314 (2015).
Kudahettige-Nilsson et al., "Biobutanol production by Clostridium acetobutylicum using xylose recovered from birch Kraft black liquor," *Bioresour. Technol.*, 176:71-79 (2015).
La Grange-Nel, "Characterisation and Improvement of Whiskey Yeast," Thesis, University of Stellenbosch, Apr. 2003.
Lee et al., "Characterization of two-substrate fermentation processes for xylitol production using recombinant *Saccharomyces cerevisiae* containing xylose reductase gene," *Process Biochem.*, 35:1199-1203 (2000).
Lee et al., "Cloning and characterization of the xyl1 gene, encoding an NADH-preferring xylose reductase from Candida parapsilosis, and its functional expression in Candida tropicalis," *Appl. Enviorn. Microbiol.*, 69(10):6179-6188 (2003).
Lee et al., "Isobutanol production in engineered *Saccharomyces cerevisiae* by overexpression of 2-ketoisovalerate decarboxylase and valine biosynthetic enzymes," *Bioprocess Biosyst. Eng.*, 35(9):1467-1475 (2012).
Liu et al., "Bacteriophage application restores ethanol fermentation characteristics disrupted by Lactobacillus fermentum," *Biotechnol. Biofuels*, 8:132 (2015).
Löser et al., "Perspectives for the biotechnological production of ethyl acetate by yeasts," *Appl. Microbiol. Biotechnol.*, 98:5397-5415 (2014).
Matsushika et al., "Ethanol production from xylose in engineered *Saccharomyces cerevisiae* strains: current state and perspectives," *Appl. Microbiol. Biotechnol.*, 84(1):37-53 (2009).
Miyoshi et al., "Activity of tick antimicrobial peptide from Ixodes persulcatus (persulcatusin) against cell membranes of drug-resistant *Staphylococcus aureus*," *J. Antibiot.*, 70:142-146 (2017).
Miyoshi et al., "Functional structure and antimicrobial activity of persulcatusin, an antimicrobial peptide from the hard tick Ixodes persulcatus," *Parasites & Vectors*, 9:85 (2016).
Morrissey et al., "Cell factory applications of the yeast Kluyveromyces marxianus for the biotechnological production of natural flavour and fragrance molecules," *Yeast*, 32(1):3-16 (2015).
Nair et al., "Evolution in reverse: engineering a D-xylose-specific xylose reductase," *ChemBioChem.*, 9(8):1213-1215 (2008).
Nora et al., "The art of vector engineering: towards the construction of next-generation genetic tools," *Microb. Biotechnol.*, 12(1):125-147 (2019).
Nozaki et al., "Production of D-arabitol by Metschnikowia reukaufii AJ14787," *Biosci. Biotechnol. Biochem.*, 67(9):1923-1929 (2003).
Oh et al., "Enhanced xylitol production through simultaneous co-utilization of cellobiose and xylose by engineered *Saccharomyces cerevisiae*," *Metab. Eng.*, 15:226-234 (2013).
Onishi et al., "Microbial production of xylitol from glucose," *Appl. Microbiol.*, 18(6):1031-1035 (1969).
Onishi et al., "The production of xylitol, L-arabinitol and ribitol by yeasts," *Agric. Biol. Chem.*, 30:1139-1144 (1966).
Osawa et al., "Recent evidence for evolution of the genetic code," *Microbiol Rev.*, 56(1):229- 264 (1992).
Pal et al., "Studies on xylitol production by metabolic pathway engineered Debaryomyces hansenii," *Bioresour. Technol.*, 147:449-455 (2013).
Pásztor et al., "A synthetic O2 -tolerant butanol pathway exploiting native fatty acid biosynthesis in *Escherichia coli*," *Biotechnol. Bioeng.*, 112(1):120-128 (2015).
Peng et al., "Controlling heterologous gene expression in yeast cell factories on different carbon substrates and across the diauxic shift: a comparison of yeast promoter activities," *Microb. Cell Fact.*, 14:91 (2015).
Peng et al., "*The role of nisin in fuel ethanol production with Saccharomyces cerevisiae,*" *Lett. Appl. Microbiol.*, 55:128-134 (2012).
Pitkanen, "Impact of Xylose and Mannose on Central Metabolism of Yeast *Saccharomyces cerevisiae*," Helsinki University of Technology, Dept. of Chem. Tech., Technical Biochemistry Report (Jan. 2005).
Porro et al., "Replacement of a metabolic pathway for large-scale production of lactic acid from engineered yeasts," *Appl. Env. Microbiol.*, 65(9):4211-4215 (1999).
Rich et al., "Resolving bacterial contamination of fuel ethanol fermentations with beneficial bacteria—An alternative to antibiotic treatment," *Bioresour. Technol.*, 247:357-362 (2018).
Roach et al., "Bacteriophage-encoded lytic enzymes control growth of contaminating Lactobacillus found in fuel ethanol fermentations," *Biotechnol. Biofuels*, 6:20 (2013).
Saha et al., "Production of D-arabitol by a newly isolated Zygosaccharomyces rouxii," *J. Ind. Microbiol. Biotechnol.*, 34(7):519-523 (2007).
Schoeman et al., "The development of bactericidal yeast strains by expressing the Pediococcus acidilactici pediocin gene (pedA) in *Saccharomyces cerevisiae,*" *Yeast*, 15)8):647-656 (1999).
Sharma et al., "Enhancement in xylose utilization using Kluyveromyces marxianus NIRE-K1 through evolutionary adaptation approach," *Bioprocess Biosyst. Eng.*, 39(5):835-843 (2016).
Shi et al., "Metabolic engineering of a synergistic pathway for n-butanol production in *Saccharomyces cerevisiae,*" *Sci. Rep.*, 6:25675 (2016).
Sirisansaneeyakul et al., "Screening of yeasts for production of xylitol from D-xylose," *J. Ferment. Bioeng.*, 80:565-570 (1995).
Skinner et al., "Bacterial contaminants of fuel ethanol production," *J. Ind. Microbiol. Biotechnol.*, 31(9):401-408 (2004).
Slininger et al., "Comparative evaluation of ethanol production by xylose-fermenting yeasts presented high xylose concentrations," *Biotechnol. Lett.*, 7(6):431-436 (1985).
Soma et al., "Direct isopropanol production from cellobiose by engineered *Escherichia coli* using a synthetic pathway and a cell surface display system," *J. Biosci. Bioeng.*, 114(1):80-85 (2012).
Steen et al., "Metabolic engineering of *Saccharomyces cerevisiae* for the production of n-butanol," *Microb. Cell Fact.* 7:36 (2008).
Sybirna et al., "A new Hansenula polymorpha HAP4 homologue which contains only the N-terminal conserved domain of the protein is fully functional in *Saccharomyces cerevisiae,*" *Curr. Genetics*, 47(3):172-181 (2005).
The Uniprot Consortium, "UniProt: the universal protein knowledgebase in 2021," *Nucl. Acids Res.*, 49:D480-D489 (2021).
Toivari et al., "Conversion of xylose to ethanol by recombinant *Saccharomyces cerevisiae:* importance of xylulokinase (XKS1) and oxygen availability," *Metabolic Eng.*, 3(3):236-249 (2001).
Toivari et al., "Metabolic engineering of *Saccharomyces cerevisiae* for conversion of D-glucose to xylitol and other five-carbon sugars and sugar alcohols," *Appl. Enviorn. Microbiol.*, 73(17):5471-5476 (2007).
Van Den Burg et al., "Engineering an enzyme to resist boiling," *Proc. Natl. Acad. Sci. USA*, 95(5):2056-2060 (1998).
Van Heel et al., "BAGEL3: automated identification of genes encoding bacteriocins and (non-)bactericidal posttranslationally modified peptides," *Nucl. Acids Res.*, 41:W448-W453 (2013).
Van Hoek et al., "Effects of pyruvate decarboxylase overproduction on flux distribution at the pyruvate branch point in *Saccharomyces cerevisiae,*" *Appl. Environ. Microbiol.*, 64(6):2133-2140 (1998).
Van Reenen et al., "Characterization and heterologous expression of a class IIa bacteriocin, plantaricin 423 from Lactobacillus plantarum 423, in *Saccharomyces cerevisiae,*" *Int. J. Food Microbial.*, 81(1):29-40 (2003).
Vandeska et al., "Effects of environmental conditions on production of xylitol byCandida boidinii," *World J. Microbiol. Biotechnol.*, 11(2):213-218 (1995).
Viña-Gonzalez et al., "Directed Evolution Method in *Saccharomyces cerevisiae*: Mutant Library Creation and Screening," *J. Vis. Exp.*, 110:e53761 (2016).
Voronovsky et al., "Expression of xylA genes encoding xylose isomerases from *Escherichia coli* and *Streptomyces coelicolor* in the methylotrophic yeast Hansenula polymorpha," *FEMS Yeast Res.*, 5(11):1055-1062 (2005).
Wang et al., "APD3: the antimicrobial peptide database as a tool for research and education," *Nucl. Acids Res.*, 44:D1087-D1093 (2016).
Waterhouse et al., "SWISS-MODEL: Homology modelling of protein structures and complexes," *Nucleic Acids Res.*, 46:W296-W303 (2018).

(56) References Cited

OTHER PUBLICATIONS

West, "Xylitol production by Candida species grown on a grass hydrolysate," *World J. Microbiol. Biotechnol.*, 25:913-916 (2009).

Xiao et al., "Metabolic engineering of D-xylose pathway in Clostridium beijerinckii to optimize solvent production from xylose mother liquid," *Metab. Eng.*, 14(5):569-578 (2012).

Xin et al., "Simultaneous fermentation of glucose and xylose to butanol by Clostridium sp. strain BOH3," *Appl. Environ. Microbiol.*, 80(15):4771-4778 (2014).

Yang et al., "Metabolic and process engineering of Clostridium cellulovorans for biofuel production from cellulose," *Metab. Eng.*, 32:39-48 (2015).

Yoon et al., "L-arabinose pathway engineering for arabitol-free xylitol production in Candida tropicalis," *Biotechnol. Lett.*, 33(4):747-753 (2011).

Yu et al., "Metabolic engineering of Clostridium tyrobutyricum for n-butanol production through co-utilization of glucose and xylose," *Biotechnol. Bioeng.*, 112(10):2134-2141 (2015).

Zha et al., "Optimization of CDT-1 and XYL1 expression for balanced co-production of ethanol and xylitol from cellobiose and xylose by engineered Saccharomyces cerevisiae," *PLOS One*, 8:e68317 (2013).

Zhang et al., "Improving xylitol production at elevated temperature with engineered Kluyveromyces marxianus through over-expressing transporters," *Bioresour. Technol.*, 175:642-645 (2015).

Zhang et al., "Simultaneous glucose and xylose uptake by an acetone/butanol/ethanol producing laboratory Clostridium beijerinckii strain SE-2," *Biotechnol. Lett.*, 38(4):611-617 (2016).

Zhang et al., "Xylitol production at high temperature by engineered Kluyveromyces marxianus," *Bioresour. Technol.*, 152:192-201 (2014).

Zhao et al., "Molecular evolution by staggered extension process (StEP) in vitro recombination," *Nature Biotechnol.*, 16(3):258-261 (1998).

\* cited by examiner

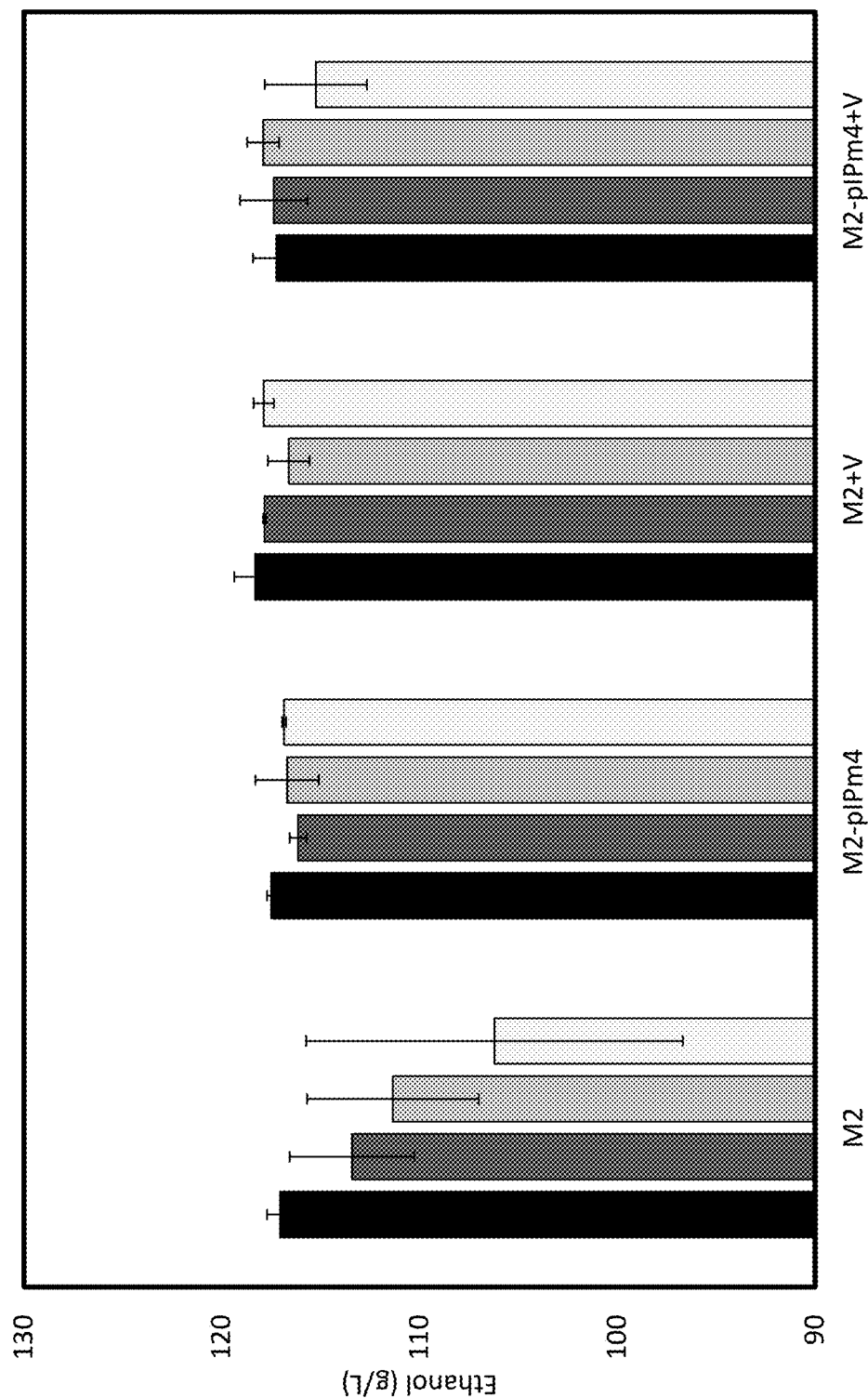

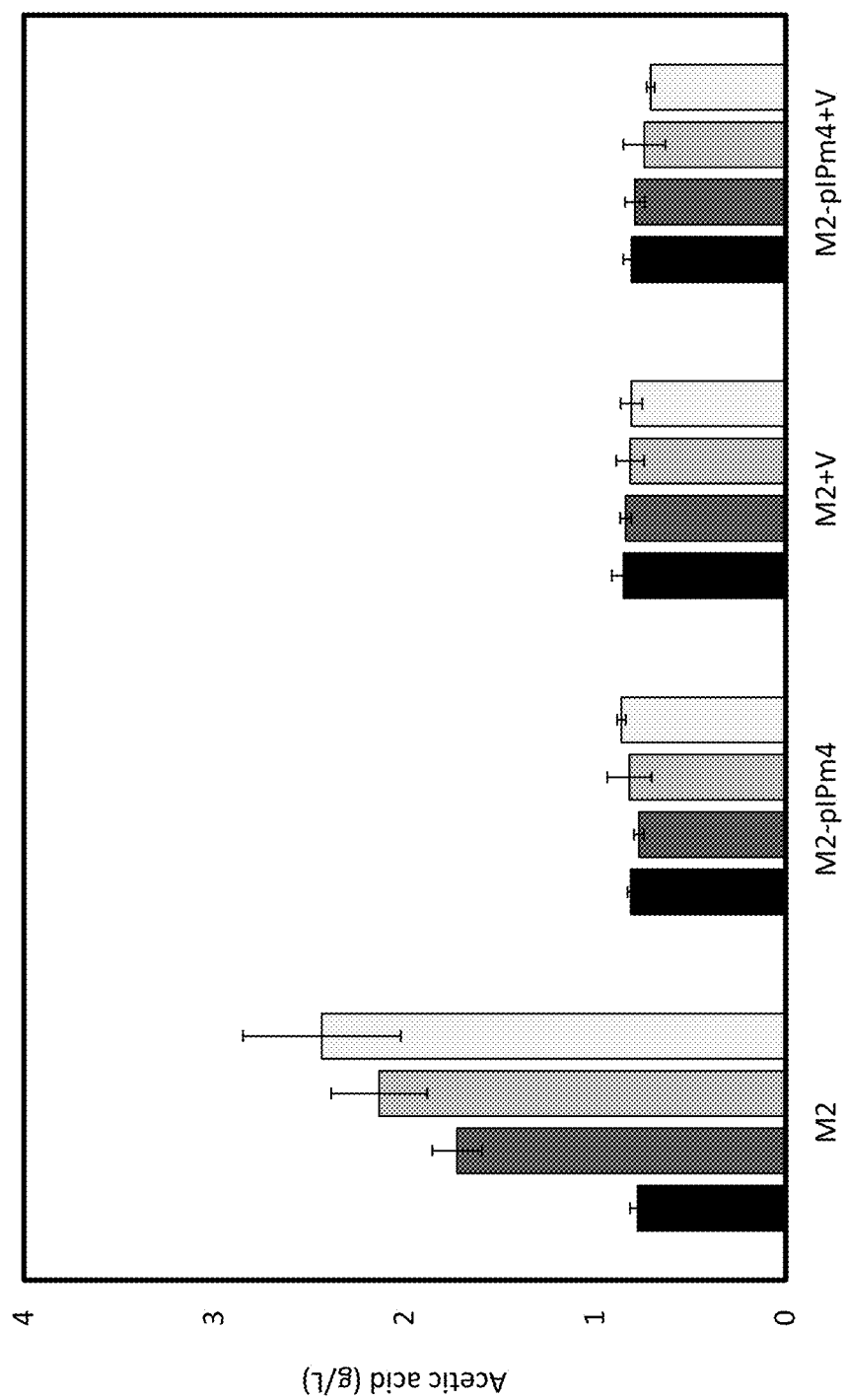

SEQUENCE LISTING

<160> NUMBER OF SEQ ID NOS: 102

<210> SEQ ID NO 1
<211> LENGTH: 38
<212> TYPE: PRT
<213> ORGANISM: Ixodes persulcatus

<400> SEQUENCE: 1

Gly Phe Gly Cys Pro Phe Asn Gln Gly Ala Cys His Arg His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
-continued

<400> SEQUENCE: 2

Gly Phe Gly Cys Pro Ala Asn Gln Gly Ala Cys His Arg His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
            35

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Phe Gly Cys Pro Phe Asn Gln Gly Ala Cys His Ala His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
            35

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Phe Gly Cys Pro Phe Asn Gln Gly Ala Cys His Arg His Cys Ala
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
            35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Phe Gly Cys Pro Phe Asn Gln Gly Ala Cys His Arg His Cys Arg
1               5                   10                  15

Ser Ile Gly Ala Arg Gly Gly Tyr Cys Ala Gly Leu Phe Lys Gln Thr
            20                  25                  30

Cys Thr Cys Tyr Ser Arg
            35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 6

Gly Phe Gly Cys Pro Phe Asn Gln Gly Ala Cys His Arg His Cys Arg
1               5                   10                  15

Ser Ile Gly Arg Ala Gly Gly Tyr Cys Ala Gly Leu Phe Lys Gln Thr
            20                  25                  30

Cys Thr Cys Tyr Ser Arg
            35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Phe Gly Cys Pro Phe Asn Gln Gly Ala Cys His Arg His Cys Arg
1               5                   10                  15

Ser Ile Gly Arg Arg Gly Gly Tyr Cys Ala Gly Ala Phe Lys Gln Thr
            20                  25                  30

Cys Thr Cys Tyr Ser Arg
            35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Phe Gly Cys Pro Phe Asn Gln Gly Ala Cys His Arg His Cys Arg
1               5                   10                  15

Ser Ile Gly Arg Arg Gly Gly Tyr Cys Ala Gly Leu Ala Lys Gln Thr
            20                  25                  30

Cys Thr Cys Tyr Ser Arg
            35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Phe Gly Cys Pro Phe Asn Gln Gly Ala Cys His Arg His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Ala
            35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 10

Gly Phe Gly Cys Pro Phe Asn Gln Gly Ala Cys His Ser His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Phe Gly Cys Pro Phe Asn Gln Gly Ala Cys His Arg His Cys Arg
1               5                   10                  15

Ser Ile Gly Arg Gly Gly Gly Tyr Cys Ala Gly Leu Phe Lys Gln Thr
            20                  25                  30

Cys Thr Cys Tyr Ser Arg
        35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Phe Gly Cys Pro Phe Asn Gln Gly Ala Cys His Arg His Cys Arg
1               5                   10                  15

Ser Ile Gly Arg Arg Gly Gly Tyr Cys Asp Gly Leu Phe Lys Gln Thr
            20                  25                  30

Cys Thr Cys Tyr Ser Arg
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Phe Gly Cys Pro Val Asn Gln Gly Ala Cys His Ser His Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 14
<211> LENGTH: 38
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 14

Gly Phe Gly Cys Pro Phe Asp Gln Gly Ala Cys His Arg His Cys Ser
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Phe Gly Cys Pro Phe Asp Gln Gly Ala Cys His Arg His Cys Arg
1               5                   10                  15

Ser Ile Gly Arg Arg Gly Gly Tyr Cys Ala Gly Leu Leu Lys Gln Thr
            20                  25                  30

Cys Thr Cys Tyr Ser Arg
        35

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Phe Gly Cys Pro Phe Asn Gln Asp Ala Cys His Arg Gln Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Phe Gly Cys Pro Phe Asn Gln Asp Ala Cys His Arg His Cys Arg
1               5                   10                  15

Ser Ile Gly Ser Arg Gly Gly Tyr Cys Ala Gly Leu Phe Lys Gln Thr
            20                  25                  30

Cys Thr Cys Tyr Ser Arg
        35

<210> SEQ ID NO 18
<211> LENGTH: 38
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 18

Gly Phe Gly Cys Pro Phe Asn Gln Gly Ala Cys His Ser His Cys Lys
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Phe Gly Cys Pro Phe Asn Gln Gly Ala Cys His Ser His Cys Arg
1               5                   10                  15

Ser Asn Gly Arg Arg Gly Gly Tyr Cys Ala Gly Leu Phe Lys Gln Thr
            20                  25                  30

Cys Thr Cys Tyr Ser Arg
        35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Phe Gly Cys Pro Phe Asn Gln Gly Ala Cys His Ser His Cys Arg
1               5                   10                  15

Ser Ile Gly Thr Arg Gly Gly Tyr Cys Ala Gly Leu Phe Lys Gln Thr
            20                  25                  30

Cys Thr Cys Tyr Ser Arg
        35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Phe Gly Cys Pro Phe Asn Gln Gly Ala Cys His Ser His Cys Arg
1               5                   10                  15

Ser Ile Gly Arg Gly Gly Gly Tyr Cys Ala Gly Leu Phe Lys Gln Thr
            20                  25                  30

Cys Thr Cys Tyr Ser Arg
        35

<210> SEQ ID NO 22
<211> LENGTH: 38
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 22

Gly Phe Gly Cys Pro Phe Asn Gln Gly Ala Cys His Ser His Cys Arg
1               5                   10                  15

Ser Ile Gly Arg Ser Gly Gly Tyr Cys Ala Gly Leu Phe Lys Gln Thr
            20                  25                  30

Cys Thr Cys Tyr Ser Arg
            35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Phe Gly Cys Pro Phe Asn Gln Gly Ala Cys His Ser His Cys Arg
1               5                   10                  15

Ser Ile Gly Arg Arg Gly Gly Tyr Cys Asp Gly Leu Phe Lys Gln Thr
            20                  25                  30

Cys Thr Cys Tyr Ser Arg
            35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Phe Gly Cys Pro Phe Asn Gln Gly Ala Cys His Ser His Cys Arg
1               5                   10                  15

Ser Ile Gly Arg Arg Gly Gly Tyr Cys Ala Gly Met Phe Lys Gln Thr
            20                  25                  30

Cys Thr Cys Tyr Ser Arg
            35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Phe Gly Cys Pro Phe Asn Gln Gly Ala Cys His Arg His Cys Ser
1               5                   10                  15

Ser Ile Gly Ser Arg Gly Gly Tyr Cys Ala Gly Leu Phe Lys Gln Thr
            20                  25                  30

Cys Thr Cys Tyr Ser Arg
            35

<210> SEQ ID NO 26
<211> LENGTH: 38

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Phe Gly Cys Pro Phe Asn Gln Gly Ala Cys His Arg His Cys Gly
1               5                   10                  15

Ser Ile Gly Arg Arg Gly Gly Tyr Cys Ala Gly Leu Val Lys Gln Thr
            20                  25                  30

Cys Thr Cys Tyr Ser Arg
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Phe Gly Cys Pro Phe Asn Gln Gly Ala Cys His Arg His Cys Arg
1               5                   10                  15

Ser Ile Gly Ser Gly Gly Gly Tyr Cys Ala Gly Leu Phe Lys Gln Thr
            20                  25                  30

Cys Thr Cys Tyr Ser Arg
        35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Phe Gly Cys Pro Leu Asp Gln Gly Ala Cys His Arg Gln Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Phe Gly Cys Pro Leu Asn Gln Asp Ala Cys His Arg Gln Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 30
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Phe Gly Cys Pro Leu Asn Gln Asp Ala Cys His Arg His Cys Arg
1               5                   10                  15

Ser Ile Gly Lys Arg Gly Gly Tyr Cys Ala Gly Leu Phe Lys Gln Thr
            20                  25                  30

Cys Thr Cys Tyr Ser Arg
        35

<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Phe Gly Cys Pro Val Asn Gln Gly Ala Cys His Ser His Cys Arg
1               5                   10                  15

Ser Ile Gly Arg Arg Gly Gly Tyr Cys Asp Gly Leu Phe Lys Gln Thr
            20                  25                  30

Cys Thr Cys Tyr Ser Arg
        35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Phe Gly Cys Pro Phe Asp Gln Gly Ala Cys His Arg Phe Cys Ser
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Phe Gly Cys Pro Phe Asn Gln Asp Ala Cys His Arg His Cys Arg
1               5                   10                  15

Ser Phe Gly Arg Arg Gly Gly Tyr Cys Ala Gly Leu Leu Lys Gln Thr
            20                  25                  30

Cys Thr Cys Tyr Ser Arg
        35
```

```
<210> SEQ ID NO 34
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Phe Gly Cys Pro Leu Asn Gln Asp Ala Cys His Ser Gln Cys Arg
1               5                   10                  15

Ser Ile Gly Arg Arg Gly Gly Tyr Cys Ala Gly Leu Phe Lys Gln Thr
            20                  25                  30

Cys Thr Cys Tyr Ser Arg
        35

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Phe Gly Cys Pro Ser Asn Gln Gly Ala Cys His Ser His Cys Lys
1               5                   10                  15

Ser Val Gly Arg Arg Gly Gly Tyr Cys Ala Gly Leu Phe Lys Gln Thr
            20                  25                  30

Cys Thr Cys Tyr Ser Arg
        35

<210> SEQ ID NO 36
<211> LENGTH: 44
<212> TYPE: PRT
<213> ORGANISM: Pediococcus acidilactici

<400> SEQUENCE: 36

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 37
<211> LENGTH: 117
<212> TYPE: DNA
<213> ORGANISM: Ixodes persulcatus

<400> SEQUENCE: 37
ggttttggtt gtccattcaa tcaaggtgct tgtcatagac attgcagatc cattggtaga      60
agaggcggtt attgtgctgg tttgtttaag caaacttgta cctgctactc caggtga       117

<210> SEQ ID NO 38
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```
ggttttggtt gtccagctaa tcaaggtgct tgtcatagac attgcagatc cattggtaga        60
agaggcggtt attgtgctgg tttgtttaag caaacttgta cctgctactc caggtga          117

<210> SEQ ID NO 39
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
ggttttggtt gtccattcaa tcaaggtgct tgtcatgctc attgcagatc cattggtaga        60
agaggcggtt attgtgctgg tttgtttaag caaacttgta cctgctactc caggtga          117

<210> SEQ ID NO 40
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ggttttggtt gtccattcaa tcaaggtgct tgtcatagac attgcgcttc cattggtaga        60
agaggcggtt attgtgctgg tttgtttaag caaacttgta cctgctactc caggtga          117

<210> SEQ ID NO 41
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ggttttggtt gtccattcaa tcaaggtgct tgtcatagac attgcagatc cattggtgct        60
agaggcggtt attgtgctgg tttgtttaag caaacttgta cctgctactc caggtga          117

<210> SEQ ID NO 42
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ggttttggtt gtccattcaa tcaaggtgct tgtcatagac attgcagatc cattggtaga        60
gctggcggtt attgtgctgg tttgtttaag caaacttgta cctgctactc caggtga          117

<210> SEQ ID NO 43
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
ggttttggtt gtccattcaa tcaaggtgct tgtcatagac attgcagatc cattggtaga        60
agaggcggtt attgtgctgg tgcttttaag caaacttgta cctgctactc caggtga          117

<210> SEQ ID NO 44
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
ggttttggtt gtccattcaa tcaaggtgct tgtcatagac attgcagatc cattggtaga     60
agaggcggtt attgtgctgg tttggctaag caaacttgta cctgctactc caggtga      117

<210> SEQ ID NO 45
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
ggttttggtt gtccattcaa tcaaggtgct tgtcatagac attgcagatc cattggtaga     60
agaggcggtt attgtgctgg tttgtttaag caaacttgta cctgctactc cgcttga      117

<210> SEQ ID NO 46
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ggttttggtt gtccattcaa tcaaggtgct tgtcatagtc attgcagatc cattggtaga     60
agaggcggtt attgtgctgg tttgtttaag caaacttgta cctgctactc caggtga      117

<210> SEQ ID NO 47
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
ggttttggtt gtccattcaa tcaaggtgct tgtcatagac attgcagatc cattggtaga     60
ggaggcggtt attgtgctgg tttgtttaag caaacttgta cctgctactc caggtga      117

<210> SEQ ID NO 48
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ggttttggtt gtccattcaa tcaaggtgct tgtcatagac attgcagatc cattggtaga     60
agaggcggtt attgtgatgg tttgtttaag caaacttgta cctgctactc caggtga      117

<210> SEQ ID NO 49
<211> LENGTH: 117
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 49
ggttttggtt gcccagtcaa tcaaggtgct tgtcatagtc attgtagatc cattggtaga     60
agaggcggat attgtgctgg tttgtttaag caaacttgta cctgctactc caggtga       117

<210> SEQ ID NO 50
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
ggttttggtt gtccattcga tcaaggcgct tgtcatagac attgcagttc cattggtaga     60
agaggcggtt attgtgctgg tttgtttaag caaacttgta cctgctactc caggtga       117

<210> SEQ ID NO 51
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ggttttggtt gtccattcga tcaaggtgct tgtcatagac attgcagatc cattggtaga     60
agaggcggtt attgtgctgg tttgcttaag caaacttgta cctgctactc taggtga       117

<210> SEQ ID NO 52
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ggctttggtt gtccattcaa tcaagatgct tgtcatagac aatgcagatc cattggtaga     60
agaggcggtt attgtgctgg tttgtttaag caaacatgta cctgctactc caggtga       117

<210> SEQ ID NO 53
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggttttggtt gcccattcaa tcaagatgct tgtcatagac attgcagatc cattggtagt     60
agaggcggtt attgtgctgg tttgtttaag caaacttgta cctgctactc caggtga       117

<210> SEQ ID NO 54
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
ggttttggtt gtccattcaa tcaaggtgct tgtcatagtc attgcaaatc cattggtaga     60
agaggcggtt attgtgctgg tttgtttaag caaacttgta cctgctactc caggtga      117

<210> SEQ ID NO 55
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
ggttttggtt gtccattcaa tcaaggtgct tgtcatagtc attgcagatc caatggtaga     60
agaggcggtt attgtgctgg tttgtttaag caaacttgta cctgctactc caggtga      117

<210> SEQ ID NO 56
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ggttttggtt gtccattcaa tcaaggtgct tgtcatagtc attgcagatc cattggtaca     60
agaggcggtt attgtgctgg tttgtttaag caaacttgta cctgctactc caggtga      117

<210> SEQ ID NO 57
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ggttttggtt gtccattcaa tcaaggtgct tgtcatagac attgcagatc cattggtagt     60
ggaggcggtt attgtgctgg tttgtttaaa caaacttgta cctgctactc caggtga      117

<210> SEQ ID NO 58
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ggttttggtt gtccattcaa tcaaggtgct tgtcatagtc attgcagatc cattggtaga     60
agtggcggtt attgtgctgg tttgtttaag caaacttgta cctgctactc caggtga      117

<210> SEQ ID NO 59
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
ggttttggtt gtccattcaa tcaaggtgct tgtcatagtc attgcagatc cattggtaga     60
agaggcggtt attgtgatgg tttgtttaag caaacttgta cctgctactc caggtga      117

<210> SEQ ID NO 60
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ggttttggtt gtccattcaa tcaaggtgct tgtcatagtc attgcagatc cattggtaga       60
agaggcggtt attgtgctgg tatgtttaag caaacttgta cctgctactc caggtga      117

<210> SEQ ID NO 61
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ggttttggtt gtccattcaa tcaaggagct tgtcatagac attgcagctc cattggtagc       60
agaggcggat attgtgctgg tttgtttaag caaacttgta cctgctactc caggtga      117

<210> SEQ ID NO 62
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ggttttggtt gtccattcaa tcaaggtgct tgtcatagac attgcggatc cattggtaga       60
agaggcggtt attgtgctgg tttggttaag caaacttgta cctgctactc caggtga      117

<210> SEQ ID NO 63
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ggttttggtt gtccattcaa tcaaggtgct tgtcatagac attgcagatc cattggtagt       60
ggaggcggtt attgtgctgg tttgtttaaa caaacttgta cctgctactc caggtga      117

<210> SEQ ID NO 64
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ggttttggct gtccactcga tcaaggtgct tgtcatagac aatgcagatc cattggtaga       60
agaggcggtt attgtgctgg tttgtttaag caaacttgta cctgctactc caggtga      117

<210> SEQ ID NO 65
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ggttttggtt gtccactcaa tcaagatgct tgtcatagac aatgcagatc cattggtaga      60
agaggcggtt attgtgctgg tttgtttaag caaacttgta cctgctactc caggtga       117

<210> SEQ ID NO 66
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ggttttggtt gtccactcaa tcaagatgct tgtcatagac attgcagatc cattggtaaa      60
agaggcggtt attgtgctgg tttgtttaag caaacttgta cctgctactc caggtga       117

<210> SEQ ID NO 67
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
ggttttggtt gtccagtcaa tcaaggtgct tgtcatagtc attgtagatc cattggtaga      60
agaggcggtt attgtgatgg tttgtttaag caaacttgta cctgctactc caggtga       117

<210> SEQ ID NO 68
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
ggttttggtt gtccgttcga tcaaggtgct tgtcatagat tttgcagttc cataggtaga      60
agaggcggtt attgtgctgg tttgtttaag caaacttgta cctgctactc caggtga       117

<210> SEQ ID NO 69
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
ggttttggat gcccattcaa tcaagatgct tgtcataggc attgcagatc ctttggtaga      60
agaggcggtt attgtgcagg tttgcttaag caaacttgta cctgctactc caggtga       117

<210> SEQ ID NO 70
<211> LENGTH: 117
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 70
ggttttggtt gtccactcaa tcaagatgct tgtcatagtc aatgcagatc cattggtaga      60
agaggcggtt attgtgctgg tttgtttaag caaacttgta cctgctactc caggtga       117

<210> SEQ ID NO 71
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
ggttttggtt gtccatccaa tcaaggtgct tgtcacagtc attgcaaatc cgttggtaga      60
agaggcggtt attgtgccgg tttgtttaag caaacttgta cctgctactc caggtga       117

<210> SEQ ID NO 72
<211> LENGTH: 135
<212> TYPE: DNA
<213> ORGANISM: Pediococcus acidilactici

<400> SEQUENCE: 72
aagtactacg gtaacggtgt tacctgtggt aaacattctt gttctgttga ttggggtaaa      60
gccactacct gcattattaa caatggtgct atggcttggg ctactggtgg tcatcaaggt     120
aatcataagt gttga                                                     135

<210> SEQ ID NO 73
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 74
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Thr Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40
```

```
<210> SEQ ID NO 75
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Tyr Tyr Gly Asn Gly Val Thr Cys Gly Lys His Ala Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 76
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Tyr Tyr Gly Asn Gly Val Thr Cys Gly Lys His Ser Cys Ala Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 77
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Lys Tyr Tyr Gly Asn Gly Val Thr Cys Gly Lys His Ser Cys Ser Val
1               5                   10                  15

Asp Trp Ala Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 78
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Lys Tyr Tyr Gly Asn Gly Val Thr Cys Gly Lys His Ser Cys Ser Val
1               5                   10                  15

Asp Trp Gly Ala Ala Thr Thr Cys Ile Ile Asn Asn Gly Ala Met Ala
            20                  25                  30

Trp Ala Thr Gly Gly His Gln Gly Asn His Lys Cys
        35                  40
```

<210> SEQ ID NO 79
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Lys Tyr Tyr Gly Asn Gly Val Thr Cys Gly Lys His Ser Cys Ser Val
1               5                   10                  15

Asp Trp Gly Lys Ala Ala Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 80
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Tyr Tyr Gly Asn Gly Val Thr Cys Gly Lys His Ala Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 81
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ala Tyr Tyr Gly Asn Gly Val Thr Cys Gly Lys His Ser Cys Ala Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 82
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Tyr Tyr Gly Asn Gly Val Thr Cys Gly Lys His Ser Cys Ser Val
1               5                   10                  15

Asp Trp Ala Lys Ala Thr Thr Cys Ile Ile Asn Asn Gly Ala Met Ala
            20                  25                  30

Trp Ala Thr Gly Gly His Gln Gly Asn His Lys Cys 35                  40

<210> SEQ ID NO 83
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Tyr Tyr Gly Asn Gly Val Thr Cys Gly Lys His Ser Cys Ser Val
1               5                   10                  15

Asp Trp Gly Ala Ala Thr Thr Cys Ile Ile Asn Asn Gly Ala Met Ala
            20                  25                  30

Trp Ala Thr Gly Gly His Gln Gly Asn His Lys Cys
            35                  40

<210> SEQ ID NO 84
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Tyr Tyr Gly Asn Gly Val Thr Cys Gly Lys His Ser Cys Ser Val
1               5                   10                  15

Asp Trp Gly Lys Ala Ala Thr Cys Ile Ile Asn Asn Gly Ala Met Ala
            20                  25                  30

Trp Ala Thr Gly Gly His Gln Gly Asn His Lys Cys
            35                  40

<210> SEQ ID NO 85
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Tyr Tyr Gly Asn Gly Val Thr Cys Gly Lys His Ala Cys Ser Val
1               5                   10                  15

Asp Trp Gly Lys Ala Ala Thr Cys Ile Ile Asn Asn Gly Ala Met Ala
            20                  25                  30

Trp Ala Thr Gly Gly His Gln Gly Asn His Lys Cys
            35                  40

<210> SEQ ID NO 86
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Tyr Tyr Gly Asn Gly Val Thr Cys Gly Lys His Ser Cys Ala Val
1               5                   10                  15

Asp Trp Gly Lys Ala Ala Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Tyr Tyr Gly Asn Gly Val Thr Cys Gly Lys His Ser Cys Ser Val
1               5                   10                  15

Asp Trp Ala Lys Ala Ala Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 88
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gcttactacg gtaacggtgt tacctgtggt aaacattctt gttctgttga ttggggtaaa      60
gccactacct gcattattaa caatggtgct atggcttggg ctactggtgg tcatcaaggt     120
aatcataagt gttga                                                      135

<210> SEQ ID NO 89
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
acgtactacg gtaacggtgt tacctgtggt aaacattctt gttctgttga ttggggtaaa      60
gccactacct gcattattaa caatggtgct atggcttggg ctactggtgg tcatcaaggt     120
aatcataagt gttga                                                      135

<210> SEQ ID NO 90
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
aagtactacg gtaacggtgt tacctgtggt aaacatgctt gttctgttga ttggggtaaa      60
gccactacct gcattattaa caatggtgct atggcttggg ctactggtgg tcatcaaggt     120
aatcataagt gttga                                                      135

<210> SEQ ID NO 91
<211> LENGTH: 135
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 91
aagtactacg gtaacggtgt tacctgtggt aaacattctt gtgctgttga ttggggtaaa    60
gccactacct gcattattaa caatggtgct atggcttggg ctactggtgg tcatcaaggt   120
aatcataagt gttga                                                    135

<210> SEQ ID NO 92
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
aagtactacg gtaacggtgt tacctgtggt aaacattctt gttctgttga ttgggctaaa    60
gccactacct gcattattaa caatggtgct atggcttggg ctactggtgg tcatcaaggt   120
aatcataagt gttga                                                    135

<210> SEQ ID NO 93
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
aagtactacg gtaacggtgt tacctgtggt aaacattctt gttctgttga ttggggtgct    60
gccactacct gcattattaa caatggtgct atggcttggg ctactggtgg tcatcaaggt   120
aatcataagt gttga                                                    135

<210> SEQ ID NO 94
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
aagtactacg gtaacggtgt tacctgtggt aaacattctt gttctgttga ttggggtaaa    60
gccgctacct gcattattaa caatggtgct atggcttggg ctactggtgg tcatcaaggt   120
aatcataagt gttga                                                    135

<210> SEQ ID NO 95
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gcttactacg gtaacggtgt tacctgtggt aaacatgctt gttctgttga ttggggtaaa    60
gccactacct gcattattaa caatggtgct atggcttggg ctactggtgg tcatcaaggt   120
aatcataagt gttga                                                    135
```

<210> SEQ ID NO 96
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gcttactacg gtaacggtgt tacctgtggt aaacattctt gtgctgttga ttggggtaaa    60
gccactacct gcattattaa caatggtgct atggcttggg ctactggtgg tcatcaaggt   120
aatcataagt gttga                                                    135

<210> SEQ ID NO 97
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gcttactacg gtaacggtgt tacctgtggt aaacattctt gttctgttga ttgggctaaa    60
gccactacct gcattattaa caatggtgct atggcttggg ctactggtgg tcatcaaggt   120
aatcataagt gttga                                                    135

<210> SEQ ID NO 98
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gcttactacg gtaacggtgt tacctgtggt aaacattctt gttctgttga ttggggtgct    60
gccactacct gcattattaa caatggtgct atggcttggg ctactggtgg tcatcaaggt   120
aatcataagt gttga                                                    135

<210> SEQ ID NO 99
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gcttactacg gtaacggtgt tacctgtggt aaacattctt gttctgttga ttggggtaaa    60
gccgctacct gcattattaa caatggtgct atggcttggg ctactggtgg tcatcaaggt   120
aatcataagt gttga                                                    135

<210> SEQ ID NO 100
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gcttactacg gtaacggtgt tacctgtggt aaacatgctt gttctgttga ttggggtaaa        60
gccgctacct gcattattaa caatggtgct atggcttggg ctactggtgg tcatcaaggt       120
aatcataagt gttga                                                        135

<210> SEQ ID NO 101
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gcttactacg gtaacggtgt tacctgtggt aaacattctt gtgctgttga ttggggtaaa        60
gccgctacct gcattattaa caatggtgct atggcttggg ctactggtgg tcatcaaggt       120
aatcataagt gttga                                                        135

<210> SEQ ID NO 102
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gcttactacg gtaacggtgt tacctgtggt aaacattctt gttctgttga ttgggctaaa        60
gccgctacct gcattattaa caatggtgct atggcttggg ctactggtgg tcatcaaggt       120
aatcataagt gttga                                                        135
```

US 11,788,053 B2

MICROORGANISMS AND METHODS FOR REDUCING BACTERIAL CONTAMINATION

CROSS-REFERENCE TO RELATED APPLICATIONS

This application claims the benefit of priority of U.S. Provisional Application No. 63/039,238, filed Jun. 15, 2020, the entire contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 25, 2021, is named 199734-010202US_SL.txt and is 42,384 bytes in size.

FIELD

The present invention relates generally to compositions and methods for reducing bacterial contamination during cell culture, and more specifically to an engineered peptide, recombinant cells capable of secreting such a peptide into culture medium, and methods of using the same for inhibiting bacterial growth during culturing of cells.

BACKGROUND

Commercial fermentation of yeast cells, such as fermentation to produce ethanol, occur in non-sterile environments and frequently suffer from bacterial contamination. Lactic acid bacteria, which are common contaminants, can compete with the yeast cells for nutrients and inhibit yeast cell growth by producing lactic acid and acetic acid (Skinner and Leathers, J. Ind. Microbiol. Biotechnol., 31:401-408 (2004); Beckner et al., Lett. Appl. Microbiol. 53:387-394 (2011); and Bischoff et al., Biotechnol. Bioeng. 103:117-122 (2009)). This production of lactic acid and acetic acid can lead to reduced ethanol yields, "stuck" fermentations, and economic loss. Small molecule antibiotics, such as virginiamycin, can inhibit bacterial growth and prevent ethanol yield loss. However, it is desirable to reduce antibiotic use due to rising concerns of antibiotic resistance in bacteria and demand for antibiotic-free distillers grains. Bacteriocins, antibacterial peptides/proteins produced by bacteria of one strain and active against those of a closely related strain, have been explored as alternatives to antibiotics (Klyachko et al., Prikl. Biokhim. Mikrobiol., 51:495-501 (2015); and van Reenen et al., Int. J. Food Microbial., 81:29-40 (2003)). Pediocin PA-1 is such a bacteriocin, which has antibacterial activity against many lactic acid bacteria (Schoeman et al., Yeast, 15:647-656 (1999)). However, pediocin PA-1 does not have antibacterial activity against all lactic acid bacteria, including those that are known to contaminate commercial fermentations of yeast. Thus, there exists a need to identify alternatives to antibiotics and other peptides that can broaden the spectrum of antibacterial activity against lactic acid bacteria. The compositions and methods described herein satisfy this need and provide related advantages.

SUMMARY OF INVENTION

Provided herein is an engineered persulcatusin. Such an engineered persulcatusin includes a variant of amino acid sequence of SEQ ID NO: 1 or a functional fragment thereof, wherein the engineered persulcatusin includes one or more alterations at positions selected from F6, N7, G9, R13, H14, R16, R20, R21, A26, L28, F29, and R38. In some embodiments, the engineered persulcatusin inhibits the growth of a lactic acid bacterium, such as a lactic acid bacterium selected from *Lactobacillus reuteri, Weissella confusa, Lactobacillus fermentum, Lactobacillus amylovorus*, and *Lactobacillus casei*. In some embodiments, the engineered persulcatusin inhibits the growth of the lactic acid bacterium with a minimum inhibitory concentration (MIC) of at least 2-fold lower than wild-type persulcatusin (SEQ ID NO: 1) as measured after 18 hours of growth in MRS media at 30° C. under atmospheric carbon dioxide concentration.

In some embodiments, an engineered persulcatusin provided herein can have one or more alterations. In some embodiments, the alterations are conservative substitutions. In some embodiments, the alterations are non-conservative substitutions. In some embodiments, the alterations are selected from substituting F6 for a non-aromatic amino acid, N7 for a negatively charged amino acid, G9 for a negatively charged amino acid, R13 for an uncharged amino acid, H14 for an aromatic or polar amino acid, R16 for an uncharged amino acid, R20 for an uncharged amino acid, R21 for an uncharged amino acid, A26 for a negatively charged amino acid, L28 for a smaller amino acid, F29 for a non-aromatic amino acid, and R38 for an uncharged amino acid. In some embodiments, the alterations are selected from F6A, F6L, F6S, F6V, N7D, G9D, R13A, R13S, H14F, H14Q, R16A, R16G, R16K, R16S, I18F, I18N, I18V, R20A, R20K, R20S, R20T, R21A, R21G, R21S, A26D, L28A, L28M, F29A, F29L, F29V, and R38A.

In some embodiments, an engineered persulcatusin provided herein can have multiple alterations. Accordingly, in some embodiments, the engineered persulcatusin includes at least two, at least three, or at least four alterations. In a specific embodiment, the engineered persulcatusin provided herein includes at least four alterations that include F6L, G9D, R13S and H14Q. In another specific embodiment, the engineered persulcatusin provided herein includes an amino acid sequence selected from SEQ ID NOS: 2-35.

In some embodiments, the engineered persulcatusin provided herein is fused to a secretion signal. Examples of such a secretion signal include, in some embodiments, the secretion signal selected from MFα1, α-amylase, glucoamylase, inulinase, invertase, killer protein, lysozyme, serum albumin, and Ost1.

Also provided herein is an isolated polynucleotide having a nucleotide sequence encoding an engineered persulcatusin provided herein. In some embodiments, the nucleotide sequence is operably linked to a heterologous promoter. In some embodiments, the polynucleotide described herein includes the nucleotide sequence of any one of SEQ ID NOS: 38-71. Still further provided herein is an expression vector having the isolated polynucleotide provided herein.

Still further provided herein is a recombinant yeast having the isolated polynucleotide or the expression vector provided herein. Such a recombinant yeast can, in some embodiments, have the isolated polynucleotide located in a chromosome or chromosomes of the recombinant yeast.

In some embodiments, a recombinant yeast described herein further includes a nucleotide sequence encoding pediocin PA-1 (SEQ ID NO: 36) or a variant or functional fragment thereof. Such a nucleotide sequence can, in some embodiments, include the nucleotide sequence of SEQ ID NO: 72.

In some embodiments, a recombinant yeast described herein is a species suitable for culturing to produce a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

In some embodiments, a recombinant yeast described herein is a species selected from *Saccharomyces cerevisiae*, *Pichia pastoris*, *Metschnikowia pulcherrima*, *Yarrowia hpolytica*, *Kluyveromyces lactis*, *Kluyveromyces marxianus*, *Scheffersomyces stipitis*, and *Hansenula polymorpha*.

Also provided herein is a recombinant yeast having isolated polynucleotides encoding: (a) wild-type persulcatusin (SEQ ID NO: 1) or a functional fragment thereof; and (b) wild-type pediocin PA-1 (SEQ ID NO: 36) or a variant or functional fragment thereof.

Still further provided herein is a culture medium having an engineered persulcatusin described herein. In some embodiments, such culture medium includes pediocin PA-1 (SEQ ID NO: 36) or a variant or functional fragment thereof.

Also provided herein is a culture medium having: (a) wild-type persulcatusin (SEQ ID NO: 1) or a functional fragment thereof; and (b) wild-type pediocin PA-1 (SEQ ID NO: 36) or a variant or functional fragment thereof.

In some embodiments, the culture medium described herein includes a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Provided herein is a method for inhibiting bacterial growth in a yeast culture. Such a method can include culturing a recombinant yeast described herein or culturing the yeast in the presence of an engineered persulcatusin described herein. Also provided herein is a method for culturing a yeast that includes co-culturing the yeast in the presence of a recombinant yeast described herein. Still further provided herein is a method for culturing a yeast that includes culturing the yeast in the presence of an engineered persulcatusin described herein. The methods described herein can, in some embodiments, include culturing by fermentation.

In some embodiments, a method provided herein can include culturing in the presence of a small molecule antibiotic. Such a small molecule antibiotic can, in some embodiments, be selected from ampicillin, chloramphenicol, clarithromycin, erythromycin, monensin, penicillin, streptomycin, tetracyclines, tylosin, virginiamycin, erythromycin, and streptomycin.

In some embodiments, a method provided herein can include culturing to produce a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Also provided herein is the use of an engineered persulcatusin described herein or a recombinant yeast described herein in the production of a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Further provided herein is an engineered pediocin PA-1. Such an engineered pediocin PA-1 includes a variant of amino acid sequence of SEQ ID NO: 36 or a functional fragment thereof, wherein the engineered pediocin PA-1 includes one or more alterations at positions selected from K1, S13, S15, G19, K20 and T22. In some embodiments, the engineered pediocin PA-1 inhibits the growth of a lactic acid bacterium, such as a lactic acid bacterium selected from *Pediococcus pentosaceus*, *Enterococcus faecium*, *Lactococcus lactis*, and *Lactobacillus delbrueckii*. In some embodiments, the engineered pediocin PA-1 inhibits the growth of the lactic acid bacterium with a minimum inhibitory concentration (MIC) of at least 2-fold lower than wild-type pediocin PA-1 (SEQ ID NO: 36) as measured after 18 hours of growth in MRS media at 30° C. under atmospheric carbon dioxide concentration.

In some embodiments, an engineered pediocin PA-1 provided herein can have one or more alterations. In some embodiments, the alterations are conservative substitutions. In some embodiments, the alterations are non-conservative substitutions. In some embodiments, the alterations are selected from substituting K1 for a non-polar amino acid or an uncharged polar amino acid, substituting S13 for a non-polar amino acid, substituting S15 for a non-polar amino acid, substituting G19 for a non-polar amino acid, substituting K20 for a non-polar amino acid and substituting T22 for a non-polar amino acid. In some embodiments, the alterations are selected from K1A, K1T, S13A, S15A, G19A, K20A, and T22A.

In some embodiments, an engineered pediocin PA-1 provided herein can have multiple alterations. Accordingly, in some embodiments, the engineered pediocin PA-1 includes at least two alterations. In a specific embodiment, the engineered pediocin PA-1 provided herein includes at least four alterations that include K1A and T22A. In another specific embodiment, the engineered pediocin PA-1 provided herein includes an amino acid sequence selected from SEQ ID NOS: 73-87.

In some embodiments, the engineered pediocin PA-1 provided herein is fused to a secretion signal. Examples of such a secretion signal include, in some embodiments, the secretion signal selected from MFα1, α-amylase, glucoamylase, inulinase, invertase, killer protein, lysozyme, serum albumin, and Ost1.

Also provided herein is an isolated polynucleotide having a nucleotide sequence encoding an engineered pediocin PA-1 provided herein. In some embodiments, the nucleotide sequence is operably linked to a heterologous promoter. In some embodiments, the polynucleotide described herein includes the nucleotide sequence of any one of SEQ ID NOS: 88-102. Still further provided herein is an expression vector having the isolated polynucleotide provided herein.

Still further provided herein is a recombinant yeast having the isolated polynucleotide or the expression vector provided herein. Such a recombinant yeast can, in some embodiments, have the isolated polynucleotide located in a chromosome or chromosomes of the recombinant yeast.

In some embodiments, a recombinant yeast described herein further includes a nucleotide sequence encoding persulcatusin (SEQ ID NO: 1) or a variant or functional fragment thereof. Such a nucleotide sequence can, in some embodiments, include the nucleotide sequence of any one of SEQ ID NOS: 37-71.

In some embodiments, a recombinant yeast described herein is a species suitable for culturing to produce a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

In some embodiments, a recombinant yeast described herein is a species selected from *Saccharomyces cerevisiae*, *Pichia pastoris*, *Metschnikowia pulcherrima*, *Yarrowia hpolytica*, *Kluyveromyces lactis*, *Kluyveromyces marxianus*, *Scheffersomyces stipitis*, and *Hansenula polymorpha*.

Also provided herein is a recombinant yeast having isolated polynucleotides encoding: (a) persulcatusin (SEQ ID NO: 1) or a variant or a functional fragment thereof and (b) pediocin PA-1 (SEQ ID NO: 36) or a variant or functional fragment thereof.

Still further provided herein is a culture medium having an engineered pediocin PA-1 described herein. In some embodiments, such culture medium includes persulcatusin (SEQ ID NO: 1) or a variant or functional fragment thereof.

Also provided herein is a culture medium having: (a) persulcatusin (SEQ ID NO: 1) or a variant or a functional fragment thereof and (b) pediocin PA-1 (SEQ ID NO: 36) or a variant or functional fragment thereof.

In some embodiments, the culture medium described herein includes a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Provided herein is a method for inhibiting bacterial growth in a yeast culture. Such a method can include culturing a recombinant yeast described herein or culturing the yeast in the presence of an engineered pediocin PA-1 described herein. Also provided herein is a method for culturing a yeast that includes co-culturing the yeast in the presence of a recombinant yeast described herein. Still further provided herein is a method for culturing a yeast that includes culturing the yeast in the presence of an engineered pediocin PA-1 described herein. The methods described herein can, in some embodiments, include culturing by fermentation.

In some embodiments, a method provided herein can include culturing in the presence of a small molecule antibiotic. Such a small molecule antibiotic can, in some embodiments, be selected from ampicillin, chloramphenicol, clarithromycin, erythromycin, monensin, penicillin, streptomycin, tetracyclines, tylosin, virginiamycin, erythromycin, and streptomycin.

In some embodiments, a method provided herein can include culturing to produce a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Also provided herein is the use of an engineered pediocin PA-1 described herein or a recombinant yeast described herein in the production of a bioderived compound. Such a bioderived compound can, in some embodiments, be selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

BRIEF DESCRIPTION OF THE DRAWINGS

FIGS. 4A-4D show exemplary results for fermentations with M2 wild-type and M2-pIPm4 expressing engineered persulcatusin having alterations F6L, G9D, R13S and H14Q from plasmids with varying levels of *L. fermentum* contamination. Filtered corn mash supplemented with 1.2 g/L ammonium sulfate was inoculated with M2 and M2-pIPm4 to an $OD_{600}$=1. M2 and M2-pIPm4 were not supplemented with virginiamycin and M2+V and M2-pIPm4+V were supplemented with 2 mg/L virginiamycin. Fermentations were not contaminated (black bars) or artificially contaminated with *L. fermentum* to $OD_{600}$ levels of 0.05 (dark grey bars), 0.1 (light grey bars), or 0.15 (white bars). After 72 hours, levels of ethanol (FIG. 4A), glucose (FIG. 4B), lactic acid (FIG. 4C), and acetic acid (FIG. 4D) were determined by HPLC. Fermentations were performed in triplicate and the error bars represent standard deviation.

DETAILED DESCRIPTION OF THE INVENTION

Figure 1:
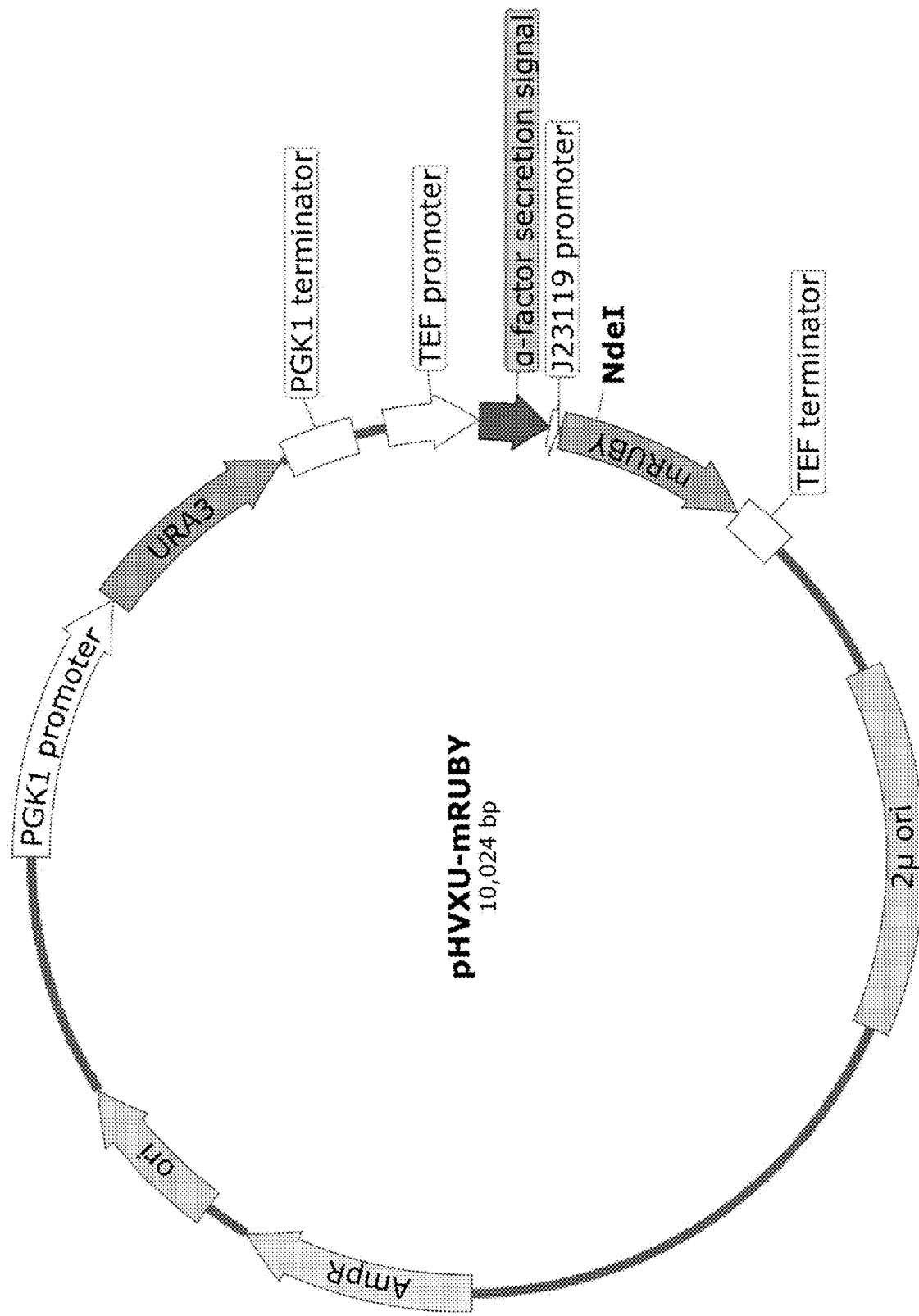
FIG. 1 shows a plasmid map of pHVXU-mRUBY. pHVXU-mRUBY was used as a vector for yeast gene expression. mRUBY expression is driven by the bacterial J23119 promoter which allows detection by fluorescence in *Escherichia coli*. The vector can be linearized by restriction enzyme digestion at the NdeI cut site located in mRUBY. The α-factor secretion signal was replaced with a hybrid secretion signal in pHVXU-mRUBY2. The J23119 promoter and mRUBY were replaced by persulcatusin immediately after the α-factor secretion signal in pHVXU-IP. This resulted in expression of secreted persulcatusin controlled by the *Ashbya gossypii* TEF promoter and terminator.

The compositions and methods provided herein are based, in part, on the engineering, isolation and characterization of novel variants of antibacterial peptides (e.g., persulcatusin and pediocin PA-1). Engineering, isolation and characterization of such variants (e.g., an engineered peptide) has revealed peptides having improved antibacterial activity against lactic acid bacteria that are known contaminants of cell cultures (e.g., yeast cell cultures). Uses for these engineered peptides include, for example, the introduction of a polynucleotide having a nucleotide sequence encoding an engineered peptide described herein (e.g., an engineered persulcatusin or an engineered pediocin PA-1) into a cell (e.g., yeast cell), which results in secretion of the engineered peptide into the culture medium, whereby the engineered peptide, when the cell is cultured, inhibits the growth of a lactic acid bacterium. Additionally, the engineered peptides described herein (e.g., an engineered persulcatusin or an engineered pediocin PA-1) can be combined with other antibacterial agents (e.g., a small molecule antibiotic (e.g., virginiamycin) and/or a bacteriocin (e.g., pediocin PA-1)) to generate antibacterial activity against a broad spectrum of bacteria, including lactic acid bacteria that are known to contaminate commercial yeast cultures. Accordingly, the engineered peptides described herein (e.g., an engineered persulcatusin or an engineered pediocin PA-1) can be used in a method for inhibiting bacterial growth in a cell culture (e.g., yeast cell culture). Such methods can include culturing of cells (e.g., yeast) in the presence of the engineered peptide described herein (e.g., an engineered persulcatusin or an engineered pediocin PA-1). Additionally, such methods can include culturing of cells (e.g., yeast) in the presence of an engineered peptide described herein for the production of a bioderived compound (e.g., ethanol). Still further provided herein are isolated polynucleotides and expression vectors having nucleotide sequences that encode an engineered peptide described herein (e.g., an engineered persulcatusin or an engineered pediocin PA-1).

Conventions and Abbreviations

| Abbreviation | Convention |
| --- | --- |
| Ala; A | Alanine |
| Arg; R | Arginine |
| Asn; N | Asparagine |
| Asp; D | Aspartic acid |
| Cys; C | Cysteine |
| Glu; E | Glutamic acid |
| Gln; Q | Glutamine |
| Gly; G | Glycine |
| His; H | Histidine |
| Ile; I | Isoleucine |
| Leu; L | Leucine |
| Lys; K | Lysine |
| Met; M | Methionine |
| Phe; F | Phenylalanine |
| Pro; P | Proline |
| Ser; S | Serine |
| Thr; T | Threonine |
| Trp; W | Tryptophan |
| Tyr; Y | Tyrosine |
| Val; V | Valine |
| MRS media | De Man, Rogosa and Sharpe media (de Man, et al., J. Appl. Bact. 23: 130-135 (1960)) |

As used herein, the term "alteration" or grammatical equivalents thereof when used in reference to any peptide, polypeptide, protein, nucleic acid or polynucleotide described herein refers to a change in structure of an amino acid residue or nucleic acid base relative to the starting or reference residue or base. An alteration of an amino acid residue includes, for example, substituting one amino acid residue for a structurally different amino acid residue. Such substitutions can be a conservative substitution, a non-conservative substitution or a substitution to a specific sub-class of amino acids, such as substitution of a residue for an aromatic amino acid, negatively charged amino acid, non-aromatic amino acid, polar amino acid, uncharged amino acid, or a combination thereof as described herein. An alteration of a nucleic acid base includes, for example, changing one naturally occurring base for a different naturally occurring base, such as changing an adenine to a thymine or a guanine to a cytosine or an adenine to a cytosine or a guanine to a thymine. An alteration of a nucleic acid base may result in an alteration of the encoding peptide, polypeptide or protein by changing the encoded amino acid residue or function of the peptide, polypeptide or protein. An alteration of a nucleic acid base may not result in an alteration of the amino acid sequence or function of encoded peptide, polypeptide or protein, also known as a silent mutation.

As used herein, the term "aromatic amino acid" refers to an amino acid residue with a side-chain that includes an aromatic ring. Examples of such amino acids include Phe (F), Trp (W), and Tyr (Y). In some aspects, an aromatic amino acid can also include His (H), although its basic properties would result in it being classified as a polar amino acid.

As used herein, the term "bioderived" means derived from or synthesized by a biological organism and can be considered a renewable resource since it can be generated by a biological organism. Such a biological organism, in particular the species of yeast disclosed herein, can utilize feedstock or biomass, such as, sugars (e.g., xylose, cellobiose, glucose, fructose, galactose (e.g., galactose from marine plant biomass), and sucrose), carbohydrates obtained from an agricultural, plant, bacterial, or animal source, and glycerol (e.g., crude glycerol byproduct from biodiesel manufacturing) for synthesis of a desired bioderived compound.

As used herein, the term "conservative substitution" refers to the replacement of one amino acid for another such that the replacement takes place within a family of amino acids that are related in their side chains. Alternatively, the term "non-conservative substitution" refers to the replacement of one amino acid residue for another such that the replaced residue is going from one family of amino acids to a different family of residues. Genetically encoded amino acids can be divided into four families: (1) acidic (negatively charged)=Asp (D), Glu (G); (2) basic (positively charged)= Lys (K), Arg (R), His (H); (3) non-polar (hydrophobic)=Cys (C), Ala (A), Val (V), Leu (L), Ile (I), Pro (P), Phe (F), Met (M), Trp (W), Gly (G), Tyr (Y), with non-polar also being subdivided into: (i) strongly hydrophobic=Ala (A), Val (V), Leu (L), Ile (I), Met (M), Phe (F); and (ii) moderately hydrophobic=Gly (G), Pro (P), Cys (C), Tyr (Y), Trp (W); and (4) uncharged polar=Asn (N), Gln (Q), Ser (S), Thr (T). In alternative fashion, the amino acid repertoire can be grouped as (1) acidic (negatively charged)=Asp (D), Glu (G); (2) basic (positively charged)=Lys (K), Arg (R), His (H), and (3) aliphatic=Gly (G), Ala (A), Val (V), Leu (L), Ile (I), Ser (S), Thr (T), with Ser (S) and Thr (T) optionally being grouped separately as aliphatic-hydroxyl; (4) aromatic=Phe (F), Tyr (Y), Trp (W); (5) amide=Asn (N), Glu (Q); and (6) sulfur-containing=Cys (C) and Met (M) (See, for example, Biochemistry, 4th ed., Ed. by L. Stryer, WH Freeman and Co., 1995, which is incorporated by reference herein in its entirety).

As used herein, the term "culture medium," "medium," "growth medium" or grammatical equivalents thereof refers to a liquid or solid (e.g., gelatinous) substance containing nutrients that supports the growth of a cell, including a microbial organism, such as the species of yeast described herein. Nutrients that support growth include: a substrate that supplies carbon, such as, but are not limited to, xylose, cellobiose, galactose, glucose, ethanol, acetate, arabinose, arabitol, sorbitol and glycerol; salts that provide essential elements including magnesium, nitrogen, phosphorus, and sulfur; a source for amino acids, such as peptone or tryptone; and a source for vitamin content, such as yeast extract. Culture medium can also include substances other than nutrients needed for growth, such as a substance that only allows select cells to grow (e.g., antibiotic or antifungal), which are generally found in selective medium, or a substance that allows for differentiation of one microbial organism over another when grown on the same medium, which are generally found in differential or indicator medium. Such substances are well known to a person skilled in the art.

As used herein, the term "engineered" or "variant" when used in reference to any peptide, polypeptide, protein, nucleic acid or polynucleotide described herein refers to a sequence of amino acids or nucleic acids having at least one alteration at an amino acid residue or nucleic acid base as compared to a parent sequence. The parent sequence of amino acids or nucleic acids can be, for example, a wild-type sequence or a homolog thereof, or a modified variant of a wild-type sequence or homolog thereof.

As used herein, the term "functional fragment" when used in reference to a peptide, polypeptide or protein is intended to refer to a portion of the peptide, polypeptide or protein that retains some or all of the activity (e.g., inhibitory activity) of the original peptide, polypeptide or protein from which the fragment was derived. Such functional fragments include amino acid sequences that are about 5 to about 10, about 5 to about 15, about 5 to about 20, about 5 to about 25, about 5 to about 30, about 5 to about 35, about 5 to about 40, about 10 to about 15, about 10 to about 20, about 10 to about 25, about 10 to about 30, about 10 to about 35, about 10 to about 40, about 15 to about 20, about 15 to about 25, about 15 to about 30, about 15 to about 35, about 15 to about 40, about 20 to about 25, about 20 to about 30, about 20 to about 35, about 20 to about 40, about 25 to about 30, about 25 to about 35, about 25 to about 40, about 30 to about 35, about 30 to about 40, or about 35 to about 40 amino acids in length. Functional fragments can also include one or more amino acid alteration described herein, such as an amino acid alteration of an engineered peptide described herein.

As used herein, the term "inhibit" or grammatical equivalents thereof when used in reference to bacterial growth refers to the bacterial growth being hindered, restrained or prevented. Such inhibition of bacterial growth can be due to either bacteriostatic or bacteriocidal activity of the inhibiting agent, or a combination of both bacteriostatic and bacteriocidal activity. A bacteriostatic agent refers to an agent that stops bacteria from reproducing, while not necessarily killing the bacteria. Such bacteriostatic activity can be measured by determining the minimum inhibitory concentration (MIC), which is the concentration of an agent that inhibits visible bacterial growth after a specific period of time of growth in specific media, at a specific temperature, and at a specific carbon dioxide concentration. A bacteriocidal agent refers to an agent that kills the bacteria, such as by lysis of the bacteria. Such bacteriostatic activity can be measured by determining the minimum bactericidal concentration (MBC), which is the concentration of an agent that results in a specific fold reduction in bacterial density at a specific period of time of growth in specific media, at a specific temperature, and at a specific carbon dioxide concentration.

As used herein, the term "isolated" when used in reference to a molecule (e.g., peptide, polypeptide, protein, nucleic acid, polynucleotide, vector) or a cell (e.g., a yeast cell) refers to a molecule or cell that is substantially free of at least one component as the referenced molecule or cell is found in nature. The term includes a molecule or cell that is removed from some or all components as it is found in its natural environment. Therefore, an isolated molecule or cell can be partly or completely separated from other substances as it is found in nature or as it is grown, stored or subsisted in non-naturally occurring environments.

As used herein, the term "lactic acid bacteria," "lactic acid bacterium" or "LAB" refers to an order of Gram-positive, low-GC, acid-tolerant, generally nonsporulating, nonrespiring, either rod-shaped (bacilli) or spherical (cocci) bacteria that share common metabolic and physiological characteristics, such as the production of lactic acid as the major metabolic end product of carbohydrate fermentation. The genera that comprise the core lactic acid bacteria are *Lactobacillus, Leuconostoc, Pediococcus, Lactococcus*, and *Streptococcus*, and lactic acid bacteria also include other genera within the order of Lactobacillales, which includes *Aerococcus, Carnobacterium, Enterococcus, Oenococcus, Sporolactobacillus, Tetragenococcus, Vagococcus, and Weissella*. Specific exemplary lactic acid bacteria species are described herein.

As used herein, the term "negatively charged amino acid" refers to an amino acid residue with a side chain that has a negative charge a pH 7.0. Examples of such amino acids include Asp (D) and Glu (G).

As used herein, the term "non-aromatic amino acid" refers to an amino acid residue that is not categorized as an aromatic amino acid. As defined herein, an aromatic amino acid has a side-chain that includes an aromatic ring, which includes Phe (F), Trp (W), Tyr (Y), and in some aspects His (H). Thus, a non-aromatic amino acid includes any naturally occurring amino acid other than Phe (F), Trp (W), Tyr (Y), and in some aspects His (H).

As used herein, the term "polar amino acid" refers to an amino acid residue with a side chain that prefer to reside in an aqueous (e.g., water) environment. Examples of such amino acids include Asp (D), Glu (E), Arg (R), Lys (K), His (H), Asn (N), Gln (Q), Ser (S), Thr (T) and Tyr (Y).

As used herein, the term "recombinant" when used in reference to a microbial organism (e.g., yeast cell) means a microbial organism that has at least one genetic alteration not normally found in the naturally occurring microbial organism, including wild-type strains of the referenced species. Genetic alterations include, for example, modifications introducing expressible polynucleotide sequences encoding peptides, polypeptides, proteins that can be secreted (e.g., an engineered peptide described herein), metabolic polypeptides, and other nucleic acid additions, nucleic acid deletions and/or other gene disruptions of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a metabolic pathway for production of a bioderived compound described herein.

As used herein, the term "secretion signal," "signal peptide," or "secretory signal peptide" refers to a sequence motif that targets a peptide, polypeptide or protein for translocation across the endoplasmic reticulum membrane and through to the environment of the host eukaryotic cell (e.g., yeast). A secretion signal is usually a short peptide (about 16 to about 30 amino acids in length) present at the N-terminus of the peptide, polypeptide or protein. The secretion signal is typically removed in the mature peptide, polypeptide or protein.

As used herein, the term "small molecule antibiotic" refers to a compound having a molecular weight below about 900 Daltons that has antibacterial activity. Non-limiting examples of small molecule antibiotics include compounds within the classes of penicillins (e.g., ampicillin), macrolides (e.g., clarithromycin, erythromycin and tylosin), tetracyclines (e.g., tetracycline and doxycycline), aminoglycosides (e.g., streptomycin), amphenicols (e.g., chloramphenicol), ionophores (e.g., monensin) and streptogramins (e.g., virginiamycin).

As used herein, the term "smaller amino acid" when used in reference to a specified amino acid residue, (e.g., Leu (L)) means an amino acid residue that has a molecular weight that is lower than the reference amino acid residue. For example, an amino acid residues that are smaller than Leu (L) includes Ala (A), Cys (C), Gly (G), Pro (P), Ser (S), Thr (T) and Val (V).

As used herein, the term "uncharged amino acid" refers to an amino acid residue with a side chain that is not charged (negatively or positively) a pH 7.0. Examples of charged amino acids include Asp (D), Glu (G), Lys (K), Arg (R), and His (H). Thus, an uncharged amino acid includes any naturally occurring amino acid other than Asp (D), Glu (G), Lys (K), Arg (R), and His (H).

Sequence identity or sequence homology, when used in reference to a nucleic acid sequence or an amino acid sequence, refers to the similarity between two or more nucleic acid molecules or between two or more polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., Current Protocols in Molecular Biology, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Engineered Peptides

Provided herein are novel engineered peptides having improved inhibition activity against select lactic acid bacteria. Such novel engineered peptides have an amino acid sequence that is a variant of a wild-type amino acid sequence, wherein the engineered peptide includes one or more alterations at identified positions of the wild-type amino acid sequence. Accordingly, in some embodiments, provided herein is an engineered persulcatusin having a variant of wild-type persulcatusin amino acid sequence of SEQ ID NO: 1 or a functional fragment thereof. Such an engineered persulcatusin includes, in some embodiments, one or more alterations at positions selected from F6, N7, G9, R13, H14, R16, R20, R21, A26, L28, F29, and R38 of SEQ ID NO. 1. In some embodiments, provided herein is an engineered pediocin PA-1 having a variant of amino acid sequence of SEQ ID NO: 36 or a functional fragment thereof. Such an engineered pediocin PA-1 includes, in some embodiments, one or more alterations at positions selected from K1, S13, S15, G19, K20 and T22 of SEQ ID NO: 36.

The engineered peptides provided herein demonstrate desirable inhibitory activity against select lactic acid bacteria. In some embodiments, the engineered peptide described herein inhibits the growth of a lactic acid bacterium that is not inhibited by the wild-type peptide or improves the activity of the peptide against a lactic acid bacterium wherein the wild-type peptide shows some inhibitory activity. In some aspects, exemplary lactic acid bacteria that are susceptible to being inhibited by the engineered persulcatusin described herein include *Lactobacillus reuteri, Weissella confusa, Lactobacillus fermentum, Lactobacillus amylovorus*, and *Lactobacillus casei*. Accordingly, in some embodiments, the engineered persulcatusin described herein inhibits the growth of *Lactobacillus reuteri*. In some embodiments, the engineered persulcatusin described herein inhibits the growth of Weissella *confusa*. In some embodiments, the engineered persulcatusin described herein inhibits the growth of *Lactobacillus fermentum*. In some embodiments, the engineered persulcatusin described herein inhibits the growth of *Lactobacillus* amylovorus. In some embodiments, the engineered persulcatusin described herein inhibits the growth of *Lactobacillus casei*. In some aspects, exemplary lactic acid bacteria that are susceptible to being inhibited by the engineered pediocin PA-1 described herein include *Pediococcus pentosaceus, Enterococcus faecium, Lactococcus lactis*, and *Lactobacillus delbrueckii*. Accordingly, in some embodiments, the engineered pediocin PA-1 described herein inhibits the growth of *Pediococcus pentosaceus*. In some embodiments, the engineered pediocin PA-1 described herein inhibits the growth of *Enterococcus faecium*. In some embodiments, the engineered pediocin PA-1 described herein inhibits the growth of *Lactococcus lactis*. In some embodiments, the engineered pediocin PA-1 described herein inhibits the growth of *Lactobacillus delbrueckii*.

The ability of the engineered peptides described herein to inhibit the growth of a lactic acid bacterium described herein can be measured using any one of the numerous well-known techniques in the art to assess such activity, including the methods exemplified herein. For example, inhibition of lactic acid bacteria can be measured by determining the minimum inhibitory concentration (MIC) or the minimum bactericidal concentration (MBC) of the engineered peptide. Accordingly, in some embodiments, an engineered peptide described herein inhibits the growth of the lactic acid bacterium with a MIC of at least 2-fold lower than the wild-type peptide. In some aspects, such a MIC is measured after 18 hours of growth in MRS media at 30° C. under atmospheric carbon dioxide concentration. Under such conditions, an engineered peptide described herein can have a MIC of at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, or at least 100-fold lower than the wild-type peptide. Alternatively, MIC can be measured under different culturing conditions, such as after 24 or 48 hours of growth, or using different media, temperatures or carbon dioxide conditions, all of which can depend upon the bacterial species or strain that is being assayed. Under such conditions, the inhibitory activity of the engineered peptide described herein is compared to the inhibitory activity of the wild-type peptide under the same conditions.

In some embodiments, provided herein is an engineered peptide having one or more alterations at identified residues of the wild-type sequence, wherein such residues have been identified as impacting the inhibition activity of the peptide against lactic acid bacteria. Such alterations, in some embodiments, can be a conservative substitution, as described herein, at the identified residue. In some embodiments, such alterations can be a non-conservative substitution, as described herein, at the identified residue. In some embodiments, the alteration at the identified residue substitutes a residue of the wild-type sequence for a residue within a specific sub-class of amino acid residues. For example, in some embodiments, an engineered persulcatusin provided herein has one or more of the following alternations: substitute F6 for a non-aromatic amino acid; substitute N7 for a negatively charged amino acid; substitute G9 for a negatively charged amino acid; substitute R13 for an uncharged amino acid; substitute H14 for an aromatic or polar amino acid; substitute substitute R16 for an uncharged amino acid; substitute R20 for an uncharged amino acid; substitute R21 for an uncharged amino acid; substitute A26 for a negatively charged amino acid; substitute L28 for a smaller amino acid; substitute F29 for a non-aromatic amino acid; and substitute R38 for an uncharged amino acid. Accordingly, in some embodiments, an engineered persulcatusin provided herein has the amino acid sequence of wild-type persulcatusin (SEQ ID NO: 1) or a functional fragment thereof, except substituting F6 for a non-aromatic amino acid. In some embodiments, an engineered persulcatusin provided herein has the amino acid sequence of wild-type persulcatusin (SEQ ID NO: 1) or a functional fragment thereof, except substituting N7 for a negatively charged amino acid. In some embodiments, an engineered persulcatusin provided herein has the amino acid sequence of wild-type persulcatusin (SEQ ID NO: 1) or a functional fragment thereof, except substituting G9 for a negatively charged amino acid. In some embodiments, an engineered persulcatusin provided herein has the amino acid sequence of wild-type persulcatusin (SEQ ID NO: 1) or a functional fragment thereof, except substituting R13 for an uncharged amino acid. In some embodiments, an engineered persulcatusin provided herein has the amino acid sequence of wild-type persulcatusin (SEQ ID NO: 1) or a functional fragment thereof, except substituting H14 for an aromatic or polar amino acid. In some embodiments, an engineered persulcatusin provided herein has the amino acid sequence of wild-type persulcatusin (SEQ ID NO: 1) or a functional fragment thereof, except substituting R16 for an uncharged amino acid. In some embodiments, an engineered persulcatusin provided herein has the amino acid sequence of wild-type persulcatusin (SEQ ID NO: 1) or a functional fragment thereof, except substituting R20 for an uncharged amino acid. In some embodiments, an engineered persulcatusin provided herein has the amino acid sequence of wild-type persulcatusin (SEQ ID NO: 1) or a functional fragment thereof, except substituting R21 for an uncharged amino acid. In some embodiments, an engineered persulcatusin provided herein has the amino acid sequence of wild-type persulcatusin (SEQ ID NO: 1) or a functional fragment thereof, except substituting A26 for a negatively charged amino acid. In some embodiments, an engineered persulcatusin provided herein has the amino acid sequence of wild-type persulcatusin (SEQ ID NO: 1) or a functional fragment thereof, except substituting L28 for a smaller amino acid. In some embodiments, an engineered persulcatusin provided herein has the amino acid sequence of wild-type persulcatusin (SEQ ID NO: 1) or a functional fragment thereof, except substituting F29 for a non-aromatic amino acid. In some embodiments, an engineered persulcatusin provided herein has the amino acid sequence of wild-type persulcatusin (SEQ ID NO: 1) or a functional fragment thereof, except substituting R38 for an uncharged amino acid.

In another example, in some embodiments, an engineered pediocin PA-1 provided herein has one or more of the following alternations: substituting K1 for a non-polar amino acid or an uncharged polar amino acid; substituting S13 for a non-polar amino acid; substituting S15 for a non-polar amino acid; substituting G19 for a non-polar amino acid; substituting K20 for a non-polar amino acid; and substituting T22 for a non-polar amino acid. Accordingly, in some embodiments, an engineered pediocin PA-1 provided herein has the amino acid sequence of wild-type pediocin PA-1 (SEQ ID NO: 36) or a functional fragment thereof, except substituting K1 for a non-polar amino acid or an uncharged polar amino acid. In some embodiments, an engineered pediocin PA-1 provided herein has the amino acid sequence of wild-type pediocin PA-1 (SEQ ID NO: 36) or a functional fragment thereof, except substituting S13 for a non-polar amino acid. In some embodiments, an engineered pediocin PA-1 provided herein has the amino acid sequence of wild-type pediocin PA-1 (SEQ ID NO: 36) or a functional fragment thereof, except substituting S15 for a non-polar amino acid. In some embodiments, an engineered pediocin PA-1 provided herein has the amino acid sequence of wild-type pediocin PA-1 (SEQ ID NO: 36) or a functional fragment thereof, except substituting G19 for a non-polar amino acid. In some embodiments, an engineered pediocin PA-1 provided herein has the amino acid sequence of wild-type pediocin PA-1 (SEQ ID NO: 36) or a functional fragment thereof, except substituting K20 for a non-polar amino acid. In some embodiments, an engineered pediocin PA-1 provided herein has the amino acid sequence of wild-type pediocin PA-1 (SEQ ID NO: 36) or a functional fragment thereof, except substituting T22 for a non-polar amino acid.

In some embodiments, provided herein is an engineered persulcatusin having one or more specific alterations. For example, an engineered persulcatusin provided herein has the amino acid sequence of wild-type persulcatusin (SEQ ID NO: 1) or a functional fragment thereof except the amino acid sequence has one or more of the following alterations: F6A, F6L, F6S, F6V, N7D, G9D, R13A, R13S, H14F, H14Q, R16A, R16G, R16K, R16S, I18F, I18N, I18V, R20A, R20K, R20S, R20T, R21A, R21G, R21S, A26D, L28A, L28M, F29A, F29L, F29V, and R38A. Accordingly, in some embodiments, an engineered persulcatusin provided herein has the amino acid sequence of wild-type persulcatusin (SEQ ID NO: 1) or a functional fragment thereof, except the alteration F6A. In some embodiments, an engineered persulcatusin provided herein has the amino acid sequence of wild-type persulcatusin (SEQ ID NO: 1) or a functional fragment thereof, except the alteration F6L. In some embodiments, an engineered persulcatusin provided herein has the amino acid sequence of wild-type persulcatusin (SEQ ID NO: 1) or a functional fragment thereof, except the alteration F6S. In some embodiments, an engineered persulcatusin provided herein has the amino acid sequence of wild-type persulcatusin (SEQ ID NO: 1) or a functional fragment thereof, except the alteration F6V. In some embodiments, an engineered persulcatusin provided herein has the amino acid sequence of wild-type persulcatusin (SEQ ID NO: 1) or a functional fragment thereof, except the alteration N7D. In some embodiments, an engineered persulcatusin provided herein has the amino acid sequence of wild-type persulcatusin (SEQ ID NO: 1) or a functional fragment thereof, except the alteration G9D. In some embodiments, an engineered persulcatusin provided herein has the amino acid sequence of wild-type persulcatusin (SEQ ID NO: 1) or a functional fragment thereof, except the alteration R13A. In some embodiments, an engineered persulcatusin provided herein has the amino acid sequence of wild-type persulcatusin (SEQ ID NO: 1) or a functional fragment thereof, except the alteration R13S. In some embodiments, an engineered persulcatusin provided herein has the amino acid sequence of wild-type persulcatusin (SEQ ID NO: 1) or a functional fragment thereof, except the alteration H14F. In some embodiments, an engineered persulcatusin provided herein has the amino acid sequence of wild-type persulcatusin (SEQ ID NO: 1) or a functional fragment thereof, except the alteration H14Q. In some embodiments, an engineered persulcatusin provided herein has the amino acid sequence of wild-type persulcatusin (SEQ ID NO: 1) or a functional fragment thereof, except the alteration R16A. In some embodiments, an engineered persulcatusin provided herein has the amino acid sequence of wild-type persulcatusin (SEQ ID NO: 1) or a functional fragment thereof, except the alteration R16G. In some embodiments, an engineered persulcatusin provided herein has the amino acid sequence of wild-type persulcatusin (SEQ ID NO: 1) or a functional fragment thereof, except the alteration R16K. In some embodiments, an engineered persulcatusin provided herein has the amino acid sequence of wild-type persulcatusin (SEQ ID NO: 1) or a functional fragment thereof, except the alteration R16S. In some embodiments, an engineered persulcatusin provided herein has the amino acid sequence of wild-type persulcatusin (SEQ ID NO: 1) or a functional fragment thereof, except the alteration I18F. In some embodiments, an engineered persulcatusin provided herein has the amino acid sequence of wild-type persulcatusin (SEQ ID NO: 1) or a functional fragment thereof, except the alteration I18N. In some embodiments, an engineered persulcatusin provided herein has the amino acid sequence of wild-type persulcatusin (SEQ ID NO: 1) or a functional fragment thereof, except the alteration I18V. In some embodiments, an engineered persulcatusin provided herein has the amino acid sequence of wild-type persulcatusin (SEQ ID NO: 1) or a functional fragment thereof, except the alteration R20A. In some embodiments, an engineered persulcatusin provided herein has the amino acid sequence of wild-type persulcatusin (SEQ ID NO: 1) or a functional fragment thereof, except the alteration R20K. In some embodiments, an engineered persulcatusin provided herein has the amino acid sequence of wild-type persulcatusin (SEQ ID NO: 1) or a functional fragment thereof, except the alteration R20S. In some embodiments, an engineered persulcatusin provided herein has the amino acid sequence of wild-type persulcatusin (SEQ ID NO: 1) or a functional fragment thereof, except the alteration R20T. In some embodiments, an engineered persulcatusin provided herein has the amino acid sequence of wild-type persulcatusin (SEQ ID NO: 1) or a functional fragment thereof, except the alteration R21A. In some embodiments, an engineered persulcatusin provided herein has the amino acid sequence of wild-type persulcatusin (SEQ ID NO: 1) or a functional fragment thereof, except the alteration R21G. In some embodiments, an engineered persulcatusin provided herein has the amino acid sequence of wild-type persulcatusin (SEQ ID NO: 1) or a functional fragment thereof, except the alteration R21S. In some embodiments, an engineered persulcatusin provided herein has the amino acid sequence of wild-type persulcatusin (SEQ ID NO: 1) or a functional fragment thereof, except the alteration A26D. In some embodiments, an engineered persulcatusin provided herein has the amino acid sequence of wild-type persulcatusin (SEQ ID NO: 1) or a functional fragment thereof, except the alteration L28A. In some embodiments, an engineered persulcatusin provided herein has the amino acid sequence of wild-type persulcatusin (SEQ ID NO: 1) or a functional fragment thereof, except the alteration L28M. In some embodiments, an engineered persulcatusin provided herein has the amino acid sequence of wild-type persulcatusin (SEQ ID NO: 1) or a functional fragment thereof, except the alteration F29A. In some embodiments, an engineered persulcatusin provided herein has the amino acid sequence of wild-type persulcatusin (SEQ ID NO: 1) or a functional fragment thereof, except the alteration F29L. In some embodiments, an engineered persulcatusin provided herein has the amino acid sequence of wild-type persulcatusin (SEQ ID NO: 1) or a functional fragment thereof, except the alteration F29V. In some embodiments, an engineered persulcatusin provided herein has the amino acid sequence of wild-type persulcatusin (SEQ ID NO: 1) or a functional fragment thereof, except the alteration R38A.

In some embodiments, provided herein is an engineered pediocin PA-1 having one or more specific alterations. For example, an engineered pediocin PA-1 provided herein has the amino acid sequence of wild-type pediocin PA-1 (SEQ ID NO: 36) or a functional fragment thereof except the amino acid sequence has one or more of the following alterations: K1A, K1T, S13A, S15A, G19A, K20A, and T22A. Accordingly, in some embodiments, an engineered pediocin PA-1 provided herein has the amino acid sequence of wild-type pediocin PA-1 (SEQ ID NO: 36) or a functional fragment thereof, except the alteration K1A. In some embodiments, an engineered pediocin PA-1 provided herein has the amino acid sequence of wild-type pediocin PA-1 (SEQ ID NO: 36) or a functional fragment thereof, except the alteration K1T. In some embodiments, an engineered pediocin PA-1 provided herein has the amino acid sequence of wild-type pediocin PA-1 (SEQ ID NO: 36) or a functional fragment thereof, except the alteration S13A. In some embodiments, an engineered pediocin PA-1 provided herein has the amino acid sequence of wild-type pediocin PA-1 (SEQ ID NO: 36) or a functional fragment thereof, except the alteration S15A. In some embodiments, an engineered pediocin PA-1 provided herein has the amino acid sequence of wild-type pediocin PA-1 (SEQ ID NO: 36) or a functional fragment thereof, except the alteration G19A. In some embodiments, an engineered pediocin PA-1 provided herein has the amino acid sequence of wild-type pediocin PA-1 (SEQ ID NO: 36) or a functional fragment thereof, except the alteration K20A. In some embodiments, an engineered pediocin PA-1 provided herein has the amino acid sequence of wild-type pediocin PA-1 (SEQ ID NO: 36) or a functional fragment thereof, except the alteration T22A.

In some embodiments, provided herein is an engineered peptide having more than one alteration. For example, an engineered persulcatusin provided herein has the amino acid sequence of wild-type persulcatusin or a functional fragment thereof with at least two, three, four, five, six, seven, eight, nine, ten, eleven, twelve or thirteen alterations described herein. Accordingly, in some embodiments, an engineered persulcatusin provided herein has the amino acid sequence of wild-type persulcatusin (SEQ ID NO: 1) or a functional fragment thereof, except two alterations described therein. In some embodiments, an engineered persulcatusin provided herein has the amino acid sequence of wild-type persulcatusin (SEQ ID NO: 1) or a functional fragment thereof, except three alterations described therein. In some embodiments, an engineered persulcatusin provided herein has the amino acid sequence of wild-type persulcatusin (SEQ ID NO: 1) or a functional fragment thereof, except four alterations described therein. In some embodiments, an engineered persulcatusin provided herein has the amino acid sequence of wild-type persulcatusin (SEQ ID NO: 1) or a functional fragment thereof, except five alterations described therein. In some embodiments, an engineered persulcatusin provided herein has the amino acid sequence of wild-type persulcatusin (SEQ ID NO: 1) or a functional fragment thereof, except six alterations described therein. In some embodiments, an engineered persulcatusin provided herein has the amino acid sequence of wild-type persulcatusin (SEQ ID NO: 1) or a functional fragment thereof, except seven alterations described therein. In some embodiments, an engineered persulcatusin provided herein has the amino acid sequence of wild-type persulcatusin (SEQ ID NO: 1) or a functional fragment thereof, except eight alterations described therein. In some embodiments, an engineered persulcatusin provided herein has the amino acid sequence of wild-type persulcatusin (SEQ ID NO: 1) or a functional fragment thereof, except nine alterations described therein. In some embodiments, an engineered persulcatusin provided herein has the amino acid sequence of wild-type persulcatusin (SEQ ID NO: 1) or a functional fragment thereof, except ten alterations described therein. In some embodiments, an engineered persulcatusin provided herein has the amino acid sequence of wild-type persulcatusin (SEQ ID NO: 1) or a functional fragment thereof, except eleven alterations described therein. In some embodiments, an engineered persulcatusin provided herein has the amino acid sequence of wild-type persulcatusin (SEQ ID NO: 1) or a functional fragment thereof, except twelve alterations described therein. In some embodiments, an engineered persulcatusin provided herein has the amino acid sequence of wild-type persulcatusin (SEQ ID NO: 1) or a functional fragment thereof, except thirteen alterations described therein. Such alterations can be a combination of conservative substitutions, non-conservative substitutions, and substitutions within a specific sub-class of amino acid residues, including substituting F6 for a non-aromatic amino acid, N7 for a negatively charged amino acid, G9 for a negatively charged amino acid, R13 for an uncharged amino acid, H14 for an aromatic or polar amino acid, R16 for an uncharged amino acid, R20 for an uncharged amino acid, R21 for an uncharged amino acid, A26 for a negatively charged amino acid, L28 for a smaller amino acid, F29 for a non-aromatic amino acid, and R38 for an uncharged amino acid. Such alterations can also include one or more specific alterations, including F6A, F6L, F6S, F6V, N7D, G9D, R13A, R13S, H14F, H14Q, R16A, R16G, R16K, R16S, I18F, I18N, I18V, R20A, R20K, R20S, R20T, R21A, R21G, R21S, A26D, L28A, L28M, F29A, F29L, F29V, and R38A.

As another example, an engineered pediocin PA-1 provided herein has the amino acid sequence of wild-type pediocin PA-1 or a functional fragment thereof with at least two, three, four, five, or six, or seven alterations described herein. Accordingly, in some embodiments, an engineered pediocin PA-1 provided herein has the amino acid sequence of wild-type pediocin PA-1 (SEQ ID NO: 36) or a functional fragment thereof, except two alterations described therein. In some embodiments, an engineered pediocin PA-1 provided herein has the amino acid sequence of wild-type pediocin PA-1 (SEQ ID NO: 36) or a functional fragment thereof, except three alterations described therein. In some embodiments, an engineered pediocin PA-1 provided herein has the amino acid sequence of wild-type pediocin PA-1 (SEQ ID NO: 36) or a functional fragment thereof, except four alterations described therein. In some embodiments, an engineered pediocin PA-1 provided herein has the amino acid sequence of wild-type pediocin PA-1 (SEQ ID NO: 36) or a functional fragment thereof, except five alterations described therein. In some embodiments, an engineered pediocin PA-1 provided herein has the amino acid sequence of wild-type pediocin PA-1 (SEQ ID NO: 36) or a functional fragment thereof, except six alterations described therein. In some embodiments, an engineered pediocin PA-1 provided herein has the amino acid sequence of wild-type pediocin PA-1 (SEQ ID NO: 36) or a functional fragment thereof, except seven alterations described therein. Such alterations can be a combination of conservative substitutions, non-conservative substitutions, and substitutions within a specific sub-class of amino acid residues, including substituting K1 for a non-polar amino acid or an uncharged polar amino acid, substituting S13 for a non-polar amino acid, substituting S15 for a non-polar amino acid, substituting G19 for a non-polar amino acid, substituting K20 for a non-polar amino acid or substituting T22 for a non-polar amino acid. Such alterations can also include one or more specific alterations, including K1A, K1T, S13A, S15A, G19A, K20A, and T22A.

In a specific embodiment, the engineered persulcatusin provided herein has at least four alterations from the wild-type persulcatusin (SEQ ID NO: 1) or functional fragment thereof that include F6L, G9D, R13S and H14Q. Other specific combinations of alterations an engineered persulcatusin provided herein can have are described in Table 1 and Examples II and III. Accordingly, in some embodiments, an engineered persulcatusin provided herein comprises a combination of alterations described in Table 1.

In a specific embodiment, the engineered pediocin PA-1 provided herein has at least two alterations from the wild-type pediocin PA-1 (SEQ ID NO: 36) or functional fragment thereof that include K1A and T22A. Other specific combinations of alterations an engineered pediocin PA-1 provided herein can have are described in Table 1 and Examples VI and VII. Accordingly, in some embodiments, an engineered persulcatusin provided herein comprises a combination of alterations described in Table 1.

In yet a more specific embodiment, the engineered persulcatusin provided herein includes an amino acid sequence described in Table 1, including an amino acid sequence selected from SEQ ID NOS: 2-35. Accordingly, in some embodiments, the engineered persulcatusin includes the amino acid sequence of SEQ ID NO: 2. In some embodiments, the engineered persulcatusin includes the amino acid sequence of SEQ ID NO: 3. In some embodiments, the engineered persulcatusin includes the amino acid sequence of SEQ ID NO: 4. In some embodiments, the engineered persulcatusin includes the amino acid sequence of SEQ ID NO: 5. In some embodiments, the engineered persulcatusin includes the amino acid sequence of SEQ ID NO: 6. In some embodiments, the engineered persulcatusin includes the amino acid sequence of SEQ ID NO: 7. In some embodiments, the engineered persulcatusin includes the amino acid sequence of SEQ ID NO: 8. In some embodiments, the engineered persulcatusin includes the amino acid sequence of SEQ ID NO: 9. In some embodiments, the engineered persulcatusin includes the amino acid sequence of SEQ ID NO: 10. In some embodiments, the engineered persulcatusin includes the amino acid sequence of SEQ ID NO: 11. In some embodiments, the engineered persulcatusin includes the amino acid sequence of SEQ ID NO: 12. In some embodiments, the engineered persulcatusin includes the amino acid sequence of SEQ ID NO: 13. In some embodiments, the engineered persulcatusin includes the amino acid sequence of SEQ ID NO: 14. In some embodiments, the engineered persulcatusin includes the amino acid sequence of SEQ ID NO: 15. In some embodiments, the engineered persulcatusin includes the amino acid sequence of SEQ ID NO: 16. In some embodiments, the engineered persulcatusin includes the amino acid sequence of SEQ ID NO: 17. In some embodiments, the engineered persulcatusin includes the amino acid sequence of SEQ ID NO: 18. In some embodiments, the engineered persulcatusin includes the amino acid sequence of SEQ ID NO: 19. In some embodiments, the engineered persulcatusin includes the amino acid sequence of SEQ ID NO: 20. In some embodiments, the engineered persulcatusin includes the amino acid sequence of SEQ ID NO: 21. In some embodiments, the engineered persulcatusin includes the amino acid sequence of SEQ ID NO: 22. In some embodiments, the engineered persulcatusin includes the amino acid sequence of SEQ ID NO: 23. In some embodiments, the engineered persulcatusin includes the amino acid sequence of SEQ ID NO: 24. In some embodiments, the engineered persulcatusin includes the amino acid sequence of SEQ ID NO: 25. In some embodiments, the engineered persulcatusin includes the amino acid sequence of SEQ ID NO: 26. In some embodiments, the engineered persulcatusin includes the amino acid sequence of SEQ ID NO: 27. In some embodiments, the engineered persulcatusin includes the amino acid sequence of SEQ ID NO: 28. In some embodiments, the engineered persulcatusin includes the amino acid sequence of SEQ ID NO: 29. In some embodiments, the engineered persulcatusin includes the amino acid sequence of SEQ ID NO: 30. In some embodiments, the engineered persulcatusin includes the amino acid sequence of SEQ ID NO: 31. In some embodiments, the engineered persulcatusin includes the amino acid sequence of SEQ ID NO: 32. In some embodiments, the engineered persulcatusin includes the amino acid sequence of SEQ ID NO: 33. In some embodiments, the engineered persulcatusin includes the amino acid sequence of SEQ ID NO: 34. In some embodiments, the engineered persulcatusin includes the amino acid sequence of SEQ ID NO: 35.

In yet a more specific embodiment, the engineered pediocin PA-1 provided herein includes an amino acid sequence described in Table 1, including an amino acid sequence selected from SEQ ID NOS: 73-87. Accordingly, in some embodiments, the engineered pediocin PA-1 includes the amino acid sequence of SEQ ID NO: 73. In some embodiments, the engineered pediocin PA-1 includes the amino acid sequence of SEQ ID NO: 74. In some embodiments, the engineered pediocin PA-1 includes the amino acid sequence of SEQ ID NO: 75. In some embodiments, the engineered pediocin PA-1 includes the amino acid sequence of SEQ ID NO: 76. In some embodiments, the engineered pediocin PA-1 includes the amino acid sequence of SEQ ID NO: 77. In some embodiments, the engineered pediocin PA-1 includes the amino acid sequence of SEQ ID NO: 78. In some embodiments, the engineered pediocin PA-1 includes the amino acid sequence of SEQ ID NO: 79. In some embodiments, the engineered pediocin PA-1 includes the amino acid sequence of SEQ ID NO: 80. In some embodiments, the engineered pediocin PA-1 includes the amino acid sequence of SEQ ID NO: 81. In some embodiments, the engineered pediocin PA-1 includes the amino acid sequence of SEQ ID NO: 82. In some embodiments, the engineered pediocin PA-1 includes the amino acid sequence of SEQ ID NO: 83. In some embodiments, the engineered pediocin PA-1 includes the amino acid sequence of SEQ ID NO: 84. In some embodiments, the engineered pediocin PA-1 includes the amino acid sequence of SEQ ID NO: 84. In some embodiments, the engineered pediocin PA-1 includes the amino acid sequence of SEQ ID NO: 86. In some embodiments, the engineered pediocin PA-1 includes the amino acid sequence of SEQ ID NO: 87.

An engineered peptide provided herein can also include, for example, amino acid deletions, insertions, fusions, or truncations when compared to the reference peptide (e.g., wild-type peptide) in addition to an alteration described herein. In addition, an engineered peptide provided herein includes those having amino acid substitutions, deletions, or insertions to the amino acid sequence outside functional residues of the peptide so long as the substitution, deletion, or insertion does not affect the inhibitory activity of the resulting peptide.

In some embodiments, an engineered peptide provided herein has 1 to 10 amino acid alterations, deletions or insertions and retains the inhibitory activity of lactic acid bacteria. In some embodiments, an engineered peptide provided herein has 1 to 5 amino acid alterations, deletions or insertions and retains the inhibitory activity of lactic acid bacteria. In some embodiments, an engineered peptide provided herein has 1 to 4 amino acid alterations, deletions or insertions and retains the inhibitory activity of lactic acid bacteria. In some embodiments, an engineered peptide provided herein has 2 to 4 amino acid alterations, deletions or insertions and retains the inhibitory activity of lactic acid bacteria. In some embodiments, an engineered peptide provided herein has 3 to 4 amino acid alterations, deletions or insertions and retains the inhibitory activity of lactic acid bacteria. In some embodiments, an engineered peptide provided herein has 4 to 5 amino acid alterations, deletions or insertions and retains the inhibitory activity of lactic acid bacteria. In some embodiments, an engineered peptide provided herein has 4 to 6 amino acid alterations, deletions or insertions and retains the inhibitory activity of lactic acid bacteria.

An engineered peptide provided herein also includes a functional fragment of a wild-type sequence or a variant sequence having one or more alteration described herein that retain its inhibitory activity of lactic acid bacteria. In some embodiments, provided herein is an engineered peptide that is a functional fragment of wild-type persulcatusin (SEQ ID NO: 1). In some embodiments, provided herein is an engineered peptide that is a functional fragment of wild-type persulcatusin (SEQ ID NO: 1) having one or more alteration described herein. In some embodiments, provided herein is an engineered peptide that is a functional fragment of wild-type persulcatusin (SEQ ID NO: 1) having one or more alterations described herein and a deletion or insertion. In some embodiments, provided herein is an engineered peptide that is a functional fragment of wild-type pediocin PA-1 (SEQ ID NO: 36). In some embodiments, provided herein is an engineered peptide that is a functional fragment of wild-type pediocin PA-1 (SEQ ID NO: 36) having one or more alteration described herein. In some embodiments, provided herein is an engineered peptide that is a functional fragment of wild-type pediocin PA-1 (SEQ ID NO: 36) having one or more alterations described herein and a deletion or insertion.

In some embodiments, provided herein is an engineered peptide that has an amino acid sequence that is at least 50% identical to a wild-type peptide, but no more than 55%, no more than 60%, no more than 65%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, or no more than 99% identical to the wild-type peptide, including, for example, wild-type persulcatusin (SEQ ID NO: 1) or wild-type pediocin PA-1 (SEQ ID NO: 36). In some embodiments, provided herein is an engineered peptide that has an amino acid sequence that is at least 80% identical to a wild-type peptide, but no more than 90%, no more than 91%, no more than 92%, no more than 93%, no more than 94%, no more than 95%, no more than 96%, no more than 97%, no more than 98%, or no more than 99% identical to the wild-type peptide, including, for example, wild-type persulcatusin (SEQ ID NO: 1) or wild-type pediocin PA-1 (SEQ ID NO: 36). In some embodiments, provided herein is an engineered peptide that has an amino acid sequence that is at least 89% identical to a wild-type peptide, but no more than 93%, no more than 95%, or no more than 98% identical to the wild-type peptide, including, for example, wild-type persulcatusin (SEQ ID NO: 1) or wild-type pediocin PA-1 (SEQ ID NO: 36).

In some embodiments, an engineered peptide described herein is fused to a secretion signal. Such a secretion signal allows for the engineered peptide to be secreted by the cell into the environment of the cell (e.g., culture medium). Once present in the environment of the cell, the engineered peptide can inhibit growth of lactic acid bacteria that is also present in the environment. Accordingly, in some embodiments, provided herein is an engineered persulcatusin or engineered pediocin PA-1 fused to a secretion signal. Such a secretion signal can be the secretion signal from MFα1, α-amylase, glucoamylase, inulinase, invertase, killer protein, lysozyme, serum albumin, or Ost1. Thus, in some embodiments, an engineered persulcatusin or engineered pediocin PA-1 provided herein is fused to the secretion signal of MFα1. In some embodiments, an engineered persulcatusin or engineered pediocin PA-1 provided herein is fused to the secretion signal of α-amylase. In some embodiments, an engineered persulcatusin or engineered pediocin PA-1 provided herein is fused to the secretion signal of glucoamylase. In some embodiments, an engineered persulcatusin or engineered pediocin PA-1 provided herein is fused to the secretion signal of inulinase. In some embodiments, an engineered persulcatusin or engineered pediocin PA-1 provided herein is fused to the secretion signal of invertase. In some embodiments, an engineered persulcatusin or engineered pediocin PA-1 provided herein is fused to the secretion signal of killer protein. In some embodiments, an engineered persulcatusin or engineered pediocin PA-1 provided herein is fused to the secretion signal of lysozyme. In some embodiments, an engineered persulcatusin or engineered pediocin PA-1 provided herein is fused to the secretion signal of serum albumin. In some embodiments, an engineered persulcatusin or engineered pediocin PA-1 provided herein is fused to the secretion signal of Ost1.

Methods for generating an engineered peptide described herein are well known in the art, including the methods exemplified herein. Any one of such methods can be used to generate an engineered peptide described herein. For example, methods for making the alterations, deletions, additions, truncations and fusions described herein are well known in the art and include, for example, site directed mutagenesis. Site-directed-mutagenesis is considered an informational approach to protein engineering and can rely on high-resolution crystallographic structures of target proteins for specific amino acid changes (Van Den Burg et al., *PNAS* 95:2056-60 (1998)). Computational methods for identifying site-specific changes for a variety of protein engineering objectives are also known in the art (Hellinga, *Nature Structural Biology* 5:525-27 (1998)). Exemplary methods for generating an engineered peptide include construction and integration of a gene expression cassette encoding the engineered peptide into the genome of a host cell (see, e.g., Dahabieh et al., *J. Enol. Vitic.,* 60:537-541 (2009)).

Other techniques known in the art include, but are not limited to, non-informational mutagenesis techniques (referred to generically as "directed evolution"). Directed evolution, in conjunction with high-throughput screening, allows for optimizing industrial enzymes (Arnold et al., *Adv.*

Biochem. Eng. Biotechnol. 58:1-14 (1997)). Directed evolution technology can include diversification methods similar to that described by Crameri et al., *Nature* 391:288-91 (1998), site-saturation mutagenesis, staggered extension process (StEP) (Zhao et al., *Nature Biotechnology* 16:258-61 (1998)), and DNA synthesis/reassembly (U.S. Pat. No. 5,965,408).

An engineered peptide described herein can be provided in an isolated form, or in a substantially purified form. The engineered peptide can be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. In some embodiments, protein chromatography is employed for purification. An engineered peptide provided herein can also be isolated by a variety of recombinant methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182 (Academic Press, (1990)). Alternatively, the engineered peptide provided herein can be obtained using well-known recombinant methods (see, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999)). The methods and conditions for biochemical purification of the isolated engineered peptide provided herein can be chosen by those skilled in the art, and purification monitored, for example, by a functional assay.

The engineered peptides described herein can be recombinantly expressed by suitable hosts. When heterologous expression of the engineered peptide is desired, the coding sequences of specific engineered peptide transporters can be modified in accordance with the codon usage of the host. The standard genetic code is well known in the art, as reviewed in, for example, Osawa et al., *Microbiol Rev.* 56(1):229-64 (1992). Yeast species, including but not limited to *Saccharomyces cerevisiae, Candida azyma, Candida diversa, Candida magnoliae, Candida rugopelliculosa, Yarrowia lipolytica*, and *Zygoascus hellenicus*, use the standard code. Certain yeast species use alternative codes. For example, "CUG," standard codon for "Leu," encodes "Ser" in species such as *Candida albicans, Candida cylindracea, Candida melibiosica, Candida parapsilosis, Candida rugose, Pichia stipitis*, and Metschnikowia species. Codon optimization can result in increased protein expression of a foreign gene in the host. Methods of Codon optimization are well known in the art (e.g., Chung et al., *BMC Syst Biol.* 6:134 (2012); Chin et al., *Bioinformatics* 30(15):2210-12 (2014)), and various tools are available (e.g., DNA2.0 at dna20.com/services/genegps; and OPTIMIZER at genomes.urv.es/OPTIMIZER).

Polynucleotides, Expression Vectors and Recombinant Yeast

Provided herein is a polynucleotide having a nucleotide sequence that encodes an engineered peptide described herein. Accordingly, in some embodiments, provided herein is an isolated polynucleotide having a nucleotide sequence that encodes an engineered persulcatusin described herein. In some embodiments, provided herein is an isolated polynucleotide having a nucleotide sequence that encodes an engineered pediocin PA-1 described herein. Exemplary nucleotide sequences of such engineered persulcatusin or engineered pediocin PA-1 can be found in Table 1. Accordingly, in some embodiments, provided herein is a polynucleotide having the nucleotide sequence of any one of SEQ ID NO: 38-71 and 88-102. In some embodiments, the polynucleotide provided herein includes the nucleotide sequence of SEQ ID NO: 38. In some embodiments, the polynucleotide provided herein includes the nucleotide sequence of SEQ ID NO: 39. In some embodiments, the polynucleotide provided herein includes the nucleotide sequence of SEQ ID NO: 40. In some embodiments, the polynucleotide provided herein includes the nucleotide sequence of SEQ ID NO: 41. In some embodiments, the polynucleotide provided herein includes the nucleotide sequence of SEQ ID NO: 42. In some embodiments, the polynucleotide provided herein includes the nucleotide sequence of SEQ ID NO: 43. In some embodiments, the polynucleotide provided herein includes the nucleotide sequence of SEQ ID NO: 44. In some embodiments, the polynucleotide provided herein includes the nucleotide sequence of SEQ ID NO: 45. In some embodiments, the polynucleotide provided herein includes the nucleotide sequence of SEQ ID NO: 46. In some embodiments, the polynucleotide provided herein includes the nucleotide sequence of SEQ ID NO: 47. In some embodiments, the polynucleotide provided herein includes the nucleotide sequence of SEQ ID NO: 48. In some embodiments, the polynucleotide provided herein includes the nucleotide sequence of SEQ ID NO: 49. In some embodiments, the polynucleotide provided herein includes the nucleotide sequence of SEQ ID NO: 50. In some embodiments, the polynucleotide provided herein includes the nucleotide sequence of SEQ ID NO: 51. In some embodiments, the polynucleotide provided herein includes the nucleotide sequence of SEQ ID NO: 52. In some embodiments, the polynucleotide provided herein includes the nucleotide sequence of SEQ ID NO: 53. In some embodiments, the polynucleotide provided herein includes the nucleotide sequence of SEQ ID NO: 54. In some embodiments, the polynucleotide provided herein includes the nucleotide sequence of SEQ ID NO: 55. In some embodiments, the polynucleotide provided herein includes the nucleotide sequence of SEQ ID NO: 56. In some embodiments, the polynucleotide provided herein includes the nucleotide sequence of SEQ ID NO: 57. In some embodiments, the polynucleotide provided herein includes the nucleotide sequence of SEQ ID NO: 58. In some embodiments, the polynucleotide provided herein includes the nucleotide sequence of SEQ ID NO: 59. In some embodiments, the polynucleotide provided herein includes the nucleotide sequence of SEQ ID NO: 60. In some embodiments, the polynucleotide provided herein includes the nucleotide sequence of SEQ ID NO: 61. In some embodiments, the polynucleotide provided herein includes the nucleotide sequence of SEQ ID NO: 62. In some embodiments, the polynucleotide provided herein includes the nucleotide sequence of SEQ ID NO: 63. In some embodiments, the polynucleotide provided herein includes the nucleotide sequence of SEQ ID NO: 64. In some embodiments, the polynucleotide provided herein includes the nucleotide sequence of SEQ ID NO: 65. In some embodiments, the polynucleotide provided herein includes the nucleotide sequence of SEQ ID NO: 66. In some embodiments, the polynucleotide provided herein includes the nucleotide sequence of SEQ ID NO: 67. In some embodiments, the polynucleotide provided herein includes the nucleotide sequence of SEQ ID NO: 68. In some embodiments, the polynucleotide provided herein includes the nucleotide sequence of SEQ ID NO: 69. In some embodiments, the polynucleotide provided herein includes the nucleotide sequence of SEQ ID NO: 70. In some embodiments, the polynucleotide provided herein includes the nucleotide sequence of SEQ ID NO: 71. In some embodiments, the polynucleotide provided herein includes the nucleotide sequence of SEQ ID NO: 88. In some embodiments, the polynucleotide provided herein includes the nucleotide sequence of SEQ ID NO: 89. In some embodiments, the polynucleotide provided herein includes the nucleotide sequence of SEQ ID NO: 90. In some embodiments, the polynucleotide provided herein includes the nucleotide sequence of SEQ ID NO: 91. In some embodiments, the polynucleotide provided herein includes the nucleotide sequence of SEQ ID NO: 92. In some embodiments, the polynucleotide provided herein includes the nucleotide sequence of SEQ ID NO: 93. In some embodiments, the polynucleotide provided herein includes the nucleotide sequence of SEQ ID NO: 94. In some embodiments, the polynucleotide provided herein includes the nucleotide sequence of SEQ ID NO: 95. In some embodiments, the polynucleotide provided herein includes the nucleotide sequence of SEQ ID NO: 96. In some embodiments, the polynucleotide provided herein includes the nucleotide sequence of SEQ ID NO: 97. In some embodiments, the polynucleotide provided herein includes the nucleotide sequence of SEQ ID NO: 98. In some embodiments, the polynucleotide provided herein includes the nucleotide sequence of SEQ ID NO: 99. In some embodiments, the polynucleotide provided herein includes the nucleotide sequence of SEQ ID NO: 100. In some embodiments, the polynucleotide provided herein includes the nucleotide sequence of SEQ ID NO: 101. In some embodiments, the polynucleotide provided herein includes the nucleotide sequence of SEQ ID NO: 102.

In some embodiments, provided herein is a polynucleotide that is at least 50% identical to a wild-type nucleotide sequence, but no more than 55%, no more than 60%, no more than 65%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, or no more than 99% identical to the wild-type nucleotide sequence, including, for example, wild-type persulcatusin (SEQ ID NO: 37) or wild-type pediocin PA-1 (SEQ ID NO: 72). In some embodiments, provided herein is a polynucleotide that has a nucleotide sequence that is at least 80% identical to a wild-type polynucleotide, but no more than 90%, no more than 91%, no more than 92%, no more than 93%, no more than 94%, no more than 95%, no more than 96%, no more than 97%, no more than 98%, or no more than 99% identical to the wild-type nucleotide sequence, including, for example, wild-type persulcatusin (SEQ ID NO: 37) or wild-type pediocin PA-1 (SEQ ID NO: 72). In some embodiments, provided herein is polynucleotide that has a nucleotide sequence that is at least 90% identical to a wild-type peptide, but no more than 95%, no more than 98%, or no more than 99% identical to the wild-type peptide, including, for example, wild-type persulcatusin (SEQ ID NO: 37) or wild-type pediocin PA-1 (SEQ ID NO: 72).

Such nucleotide sequences encoding an engineered peptide described herein can be, in some embodiments, operably linked to a heterologous promoter. Such a heterologous promoter can be used to drive expression of the engineered peptide in the host cell, which can be subsequently secreted to the extracellular environment of the host cell. Examples of such promoters are described herein, including the TDH3 promoter and a TEF promoter. Other exemplary promoters that can be used for expression of an engineered peptide described herein include glycolytic promoters (PGK1, TDH3, ENO2, ADH1, or TPI1), translational elongation factor promoters (TEF: TEF1, TEF2 or YEF3), galactose metabolic promoters (GAL10/GAL1), ribosomal protein promoters (RPL3, RPL15A, RPL4 or RPL8B), chaperone promoters (SSA1 or SSB1), the copper-inducible CUP1 promoter, low-glucose-inducible promoters (TPS1, HXT7, ADH2 and CYC1), and the PDA1 promoter (see, e.g., Peng et al., *Microb. Cell Fact.*, 14:91 (2015))

In some embodiments, provided herein is an expression vector that includes a polynucleotide having a nucleotide sequence that encodes an engineered peptide described herein. Such an expression vector can include a heterologous promoter driving the expression of an engineered peptide described herein. An expression vector provided herein can be used to introduce an engineered peptide into a host cell, for expression and secretion into the host cell's environment (e.g., culture medium). Expression vectors can be a plasmid, which may remain episomal and replicating outside of the host cell genome or be integrated into a host cell genome. Expression vectors that can be used to express the engineered peptide are well known in the art, any one of which can be used in a host cell (e.g., yeast) (see, e.g., Gnügge and Rudolf, *Yeast*, 34:205-221 (2017) and Nora et al., *Microbial Biotechnology*, 12:125-147 (2019)).

In some embodiments, provided herein is a recombinant yeast having the isolated polynucleotide described herein or the expression vector described herein. The form in which the recombinant yeast has the polynucleotide can be any one of the forms that are well known in the art, including episomally or integrated into a yeast chromosome. Thus, in some embodiments, the isolated polynucleotide is located in a chromosome of the recombinant yeast. In some embodiments, the isolated polynucleotide is part of an expression vector, such as a plasmid.

In some embodiments, provided herein is a recombinant yeast having a polynucleotide described herein as well as a nucleotide sequence encoding a different peptide having antibacterial activity, such as activity against one or more lactic acid bacteria. Such a different peptide can have complementary activity against the engineered persulcatusin and/or engineered pediocin PA-1 described herein. In other words, the recombinant yeast can have a polynucleotide encoding a peptide that has antibacterial activity against different bacteria as compared to the engineered persulcatusin and/or engineered pediocin PA-1 described herein. Exemplary peptides are described herein, including those peptides described in Example V. Accordingly, in some embodiments, provided herein is a recombinant yeast having a polynucleotide encoding an engineered persulcatusin described herein as well as a nucleotide sequence encoding pediocin PA-1 (SEQ ID NO: 36) or a variant or functional fragment thereof. In some embodiments, provided herein is a recombinant yeast having a polynucleotide encoding an engineered persulcatusin described herein or a functional fragment thereof as well as an engineered pediocin PA-1 described herein or a functional fragment thereof. Such a nucleotide sequence encoding pediocin PA-1 can have the nucleotide sequence of SEQ ID NO: 72. Such a nucleotide sequence encoding an engineered pediocin PA-1 can have the nucleotide sequence of any one of SEQ ID NOS: 88-102. Additionally, in some embodiments, provided herein is a recombinant yeast having at least two, at least three, at least four or at least five different polynucleotides each having a nucleotide sequence encoding a different peptide that has antibacterial activity, including for example the engineered persulcatusin described herein and/or an engineered pediocin PA-1 described herein, and one or more peptides described in Example V. Accordingly, in some embodiments, provided herein is a recombinant yeast having isolated polynucleotides encoding: (a) wild-type persulcatusin (SEQ ID NO: 1) or a variant or a functional fragment thereof; and (b) wild-type pediocin PA-1 (SEQ ID NO: 36) or a variant or functional fragment thereof.

The recombinant yeast provided herein includes any yeast species that is suitable for culturing to produce a bioderived compound. Such yeast are well known in the art, including yeast that are suitable for fermentation to produce a bio-derived compound and/or use in the production of a food or a beverage, such as wine, beer, or whiskey. Exemplary species of yeast include the species is selected from *Saccharomyces cerevisiae*, *Pichia pastoris*, *Metschnikowia pulcherrima*, *Yarrowia lipolytica*, *Kluyveromyces lactis*, *Kluyveromyces marxianus*, *Scheffersomyces stipitis*, and *Hansenula polymorpha*. Accordingly, in some embodiments, the recombinant yeast provided herein is a strain of *Saccharomyces cerevisiae*. In some embodiments, the recombinant yeast provided herein is a strain of *Pichia pastoris*. In some embodiments, the recombinant yeast provided herein is a strain of *Metschnikowia pulcherrima*. In some embodiments, the recombinant yeast provided herein is a strain of *Yarrowia* hpolytica. In some embodiments, the recombinant yeast provided herein is a strain of *Kluyveromyces lactis*. In some embodiments, the recombinant yeast provided herein is a strain of *Kluyveromyces marxianus*. In some embodiments, the recombinant yeast provided herein is a strain of *Scheffersomyces stipitis*. In some embodiments, the recombinant yeast provided herein is a strain of *Hansenula* polymor.

In some embodiments, provided herein is a recombinant yeast for the production of a bioderived compound, wherein the recombinant yeast has a polynucleotide described herein, such as a polynucleotide having a nucleotide sequence encoding an engineered persulcatusin or engineered pediocin PA-1 described herein. Such a recombinant yeast includes any recombinant yeast that can be used to produce one or more of the numerous bioderived compounds that are well known in the art. In some embodiments, the recombinant yeast has one or more biosynthetic pathways to produce a bioderived compound. Exemplary bioderived compounds that can be produced by a recombinant yeast provided herein include a bioderived compound selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey. Accordingly, in some embodiments, a recombinant yeast having an engineered peptide described herein is a recombinant yeast that can produce ethanol. In some embodiments, a recombinant yeast having an engineered peptide described herein is a recombinant yeast that can produce xylitol. In some embodiments, a recombinant yeast having an engineered peptide described herein is a recombinant yeast that can produce n-butanol. In some embodiments, a recombinant yeast having an engineered peptide described herein is a recombinant yeast that can produce isobutanol. In some embodiments, a recombinant yeast having an engineered peptide described herein is a recombinant yeast that can produce isopropanol. In some embodiments, a recombinant yeast having an engineered peptide described herein is a recombinant yeast that can produce arabitol. In some embodiments, a recombinant yeast having an engineered peptide described herein is a recombinant yeast that can produce ethyl acetate. In some embodiments, a recombinant yeast having an engineered peptide described herein is a recombinant yeast that can produce phenyl-ethyl alcohol. In some embodiments, a recombinant yeast having an engineered peptide described herein is a recombinant yeast that can produce 2-methyl-butanol. In some embodiments, a recombinant yeast having an engineered peptide described herein is a recombinant yeast that can produce 3-methyl-butanol. In some embodiments, a recombinant yeast having an engineered peptide described herein is a recombinant yeast that can produce a combination of carbonyl compounds, alcohols, acetals, acids, esters and nitrogen compounds found in wine, beer, or whiskey.

The biosynthetic pathway contained in the recombinant yeast to produce a bioderived compound can be an endogenous pathway or an exogenous pathway. The recombinant yeast provided herein can further have expressible nucleic acids encoding one or more of the enzymes or proteins participating in one or more biosynthetic pathways for products such as ethanol, xylitol, n-butanol, isobutanol, isopropanol, arabitol, ethyl acetate, phenyl-ethyl alcohol, 2-methyl-butanol, 3-methyl-butanol or a combination of carbonyl compounds, alcohols, acetals, acids, esters and nitrogen compounds found in wine, beer, or whiskey. Depending on the recombinant yeast chosen for biosynthesis, nucleic acids for some or all of a particular biosynthetic pathway can be expressed. In some embodiments, the recombinant yeast can be deficient in one or more enzymes or proteins for a desired biosynthetic pathway, then expressible nucleic acids for the deficient enzyme(s) or protein(s) are introduced into the yeast for subsequent exogenous expression. Alternatively, if the chosen yeast exhibits endogenous expression of some pathway genes, but is deficient in others, then an encoding nucleic acid is needed for the deficient enzyme(s) or protein(s) to achieve biosynthesis of the desired compound. Thus, a recombinant yeast can further include exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired bioderived compound, such as ethanol, xylitol, n-butanol, isobutanol, isopropanol, arabitol, ethyl acetate, phenyl-ethyl alcohol, 2-methyl-butanol, 3-methyl-butanol or a combination of carbonyl compounds, alcohols, acetals, acids, esters and nitrogen compounds found in wine, beer, or whiskey from xylose.

Microbial organisms having a biosynthesis pathway to produce ethanol are known in the art, as discussed below. In some embodiments, provided herein are recombinant yeast having at least one polynucleotide encoding an engineered peptide as described herein, as well as a biosynthesis pathway for producing ethanol. With protection from bacterial contaminants, such as lactic acid bacteria contamination, improved production of ethanol can be achieved. Provided herein are also methods of producing a bioderived ethanol by culturing the recombinant yeast provided herein having an ethanol biosynthesis pathway under conditions and for a sufficient period of time to produce ethanol.

Yeasts are considered promising microorganisms for alcoholic fermentation. They have larger cells than bacteria, are resistant to viral infection, and tend to be more resistant to negative feedback from ethanol. Furthermore, yeast growth and metabolism have been extensively studied for a number of species. For example, a number of yeasts are known to naturally ferment D-xylose. These include, for example, *P. stipitis*, *C. shehatae*, and *P. tannophilus*. The common brewer's yeast *S. cerevisiae* is not known to ferment D-xylose naturally, but a number of strains of metabolically engineered *S. cerevisiae* that do ferment D-xylose have been reported. Additionally, numerous studies have described the metabolism of D-xylose by recombinant *S. cerevisiae* (see, e.g., Matsushika et al., *Applied Microbiology and Biotechnology* 84, no. 1 (2009): 37-53; U.S. Pat. Pub. No. 2005/0153411A1 (Jul. 14, 2005); U.S. Pat. Pub. No. 2004/0231661A1 (Nov. 25, 2004); U.S. Pat. No. 4,368,268 (Jan. 11, 1983); U.S. Pat. No. 6,582,944 (Jun. 24, 2003); U.S. Pat. No. 7,226,735 (Jun. 5, 2007); U.S. Pat. Pub. No. 2004/0142456A1 (Jul. 22, 2004); Jeffries, T. W. & Jin, Y-S., *Appl. Microbiol. Biotechnol.* 63: 495-509 (2004); *Jin, Y-S., Met. Eng.* 6: 229-238 (2004); Pitkanen, J-Y., Helsinki Univ. of Tech., Dept. of Chem. Tech., Technical Biochemistry Report (January 2005); Porro, D. et al., *App. & Env. Microbiol.* 65(9): 4211-4215 (1999); Jin, Y-S., et al., *App. & Env. Microbiol.* 70(11): 6816-6825 (2004); Sybirna, K, et al., *Curr. Genetics* 47(3): 172-181 (2005); Toivari, M. H., et al., *Metabolic Eng.* 3:236-249 (2001).

D-Xylose metabolism in yeast proceeds along a pathway similar to that of glucose via pentose phosphate pathway. Carbon from D-xylose is processed to ethanol via the glycolytic cycle or to $CO_2$ via respiratory TCA cycle. Fermentation to ethanol relies in part on the metabolism of pyruvate, which is a metabolite that may be used in either respiration or fermentation (see, e.g., van Hoek, P., et al., *Appl. & Enviro. Microbiol.* 64(6); 2133-2140 (1998)). Other microbial organisms capable of ethanol production include the thermotolerant methylotrophic yeast *Hansenula polymorpha* (also known as *P. angusta*), which was reported to have optimum and maximum growth temperatures of 37° C. and 48° C., respectively, and can naturally ferment D-xylose under certain conditions (see, e.g., U.S. Pat. No. 8,071,298; Voronovsky et al., *FEMS Yeast Res.* 5(11): 1055-62 (2005)). Additionally, three strains of *P. stipitis* and three of *C. shehatae* were reported to ferment xylose when subjected to both aerobic and microaerophilic conditions. Of the strains considered, *P. stipitis* NRRL Y-7124 was able to utilize all but 7 g/L of 150 g/L xylose supplied aerobically to produce 52 g/L ethanol at a yield of 0.39 g per gram xylose (76% of theoretical yield) and at a rate comparable to the fastest shown by *C. shehatae* NRRL Y-12878. For all strains tested, fermentation results from aerobic cultures were more favorable than those from microaerophilic cultures (see, e.g., Slininger, P. J. et al., *Biotechnol Lett* (1985) 7: 431).

It is understood that recombinant yeast provided herein or otherwise known in the art with either natural or engineered biosynthesis pathways to produce ethanol can be used as the host strain, which can improve production of ethanol when expressing a polynucleotide encoding an engineered peptide as described herein. Further metabolic engineering can be adopted to stull further increase ethanol production in these host strains.

Microbial organisms having a biosynthesis pathway to produce xylitol are known in the art, as discussed in more detail below. In some embodiments, provided herein are recombinant yeast having at least one polynucleotide encoding an engineered peptide as described herein, as well as a biosynthesis pathway for producing xylitol. With protection from bacterial contaminants, such as lactic acid bacteria contamination, improved production of xylitol can be achieved. Provided herein are also methods of producing a bioderived xylitol by culturing the recombinant yeast provided herein having an xylitol biosynthesis pathway under conditions and for a sufficient period of time to produce xylitol.

Many yeast species (*Candida* spp., Debaryomyces *hansenii*, *Pichia anomala*, *Kluyveromvces* spp, *Pachysolen tannophilus*, *Saccharomyces* spp. and *Schizosaccharomyces pombe*) have been identified with the ability to convert xylose to xylitol (see, e.g., Sirisansaneeyakul et al., *J. Ferment. Bioeng.* 80:565-570 (1995); Onishi et al., *Agric. Biol. Chem.* 30:1139-1144 (1966); Barbosa et al., *J. Ind. Microbiol.* 3:241-251 (1988); Gong et al., *Biotechnol. Lett.* 3:125-130 (1981); Vandeska et al., *World J. Microbiol. Biotechnol.* 11:213-218 (1995); Dahiya et al., *Cabdirect.org* 292-303 (1990); Gong et al., *Biotechnol. Bioeng.* 25:85-102 (1983)). The ability to produce xylitol from xylulose has also been discovered in various yeast (*Saccharomyces* spp., *D. hansenii*, *P. farinose*, *Hansenula* spp., *Endomycopsis chodatii*, *Candida* spp. and *Cryptococcus neoformans*) (see, e.g., Onishi et al., *Appl. Microbiol.* 18:1031-1035 (1969)). The majority of research into the biological production of xylitol is with yeast, and novel yeast species capable of converting xylose to xylitol continue to be discovered (see, e.g., Kamat et al., *J. App. Microbiol.* 115: 1357-1367 (2013); Bura et al., *J. Ind. Microbiol. Biotechnol.* 39:1003-1011 (2012); Junyapate et al., *Antonie Van Leeuwenhoek* 105:471-480 (2014); Guaman-Burneo et al., *Antonie Van Leeuwenhoek* 108: 919-931 (2015); Cadete et al., *Int. J. Syst. Evolv. Microbiol.* 65:2968-2974 (2015)).

*S. cerevisiae* is a yeast organism that is used in many food processes, but does not naturally utilize xylose efficiently. It has been engineered to produce xylitol from xylose by expressing xylose reductases from other yeast species such as *S. stipitis* (*P. stipitis*) and *C. shehatae* (see, e.g., Hallborn et al., *Bio/Technology* 9:1090-1095; Hallborn et al., *Appl. Microbiol. Biotechol.* 42:326-333 (1994); Lee et al., *Process Biochem.* 35:1199-1203 (2000); Giovinden et al., *Appl. Microbiol. Biotechnol.* 55:76-80 (2001); Chung et al., *Enzyme Microb. Technol.* 30:809-816 (2002)).

Alternate pathways for xylitol production in *S. cerevisiae* have been explored. Expression of *S. stipitis* xylitol dehydrogenase and deletion of the xylulokinase gene in a transketolase-deficient strain of *S. cerevisiae* allowed conversion of glucose to xylitol through a multistep pathway (see, e.g., Toivari et al., *Appl. Enviorn. Microbiol.* 73:5471-5476 (2007)).

Expression of *Neurospora crassa* cellodextrin transporter and intracellular β-glucosidase allowed it to simultaneously utilize cellobiose and xylose during xylitol production (see, e.g., Oh et al., *Metab. Eng.* 15:226-234 (2013); Zha et al., *PLoS One* 8:e68317 (2013)). Furthermore, the overexpression of *S. cerevisae* ALD5, IDP2 or *S. stipitis* ZWF1 lead to increased NADPH levels, resulting in higher xylitol productivity (see, e.g., Oh et al., *Metab. Eng.* 15:226-234 (2013)).

Xylitol production can be improved by the use of both NADPH-preferring and NADH-preferring xylose reductases to decrease the limitation of NAD(P)H cofactors. This strategy was used in *S. cerevisiae* with the expression of wild-type NADPH-preferring and mutant NADH-preferring *S. stipitis* xylose reductase and *S. cerevisiae* ZWF1 and ACS1 (see, e.g., Jo et al., *Biotechnol. J.* 10:1935-1943 (2015)).

In order to decrease processing costs of xylitol production, *S. stipitis* xylose reductase, *Aspergillus aculeatus* β-glucosidase, *A. oryzae* β-xylosidase, and *Trichoderma reesei* endoxylanase were expressed in *S. cerevisiae* (see, e.g., Guirimand et al., *Appl. Microbiol. Biotechnol.* 100: 3477-3487 (2016)). Expression of these fungal enzymes allowed direct degradation of hemicellulose without the addition of exogenous enzymes.

*C. tropicalis* is pathogenic, but is also one of the natural producers of xylitol. Several patents and literature have described the application of yeast from genus *Candida* as the host strain for xylitol production from xylose; i.e. *C. tropicalis* ATCC 13803 (PCT/IN2009/000027 & KR100259470), *C. tropicalis* ATCC 9968 (PCT/FI1990/000015), *C. tropicalis* KFCC 10960 (KR100199819), *C. tropicalis* (NRRL 12968) (PCT/IN2013/000523), *C. tropicalis* ATCC 750 (West et al., *World J. Mircrobiol. Biotechnol.* 25:913-916 (2009)) and *C. tropicalis* ATCC 7349 (SAROTE et al., *J. Ferment. and Bioeng.* 80:565-570 (1995)). One strategy used to improve xylitol production in *C. tropicalis* was the expression of an NADH-preferring xylose reductase from *C. parapsilosis*, which allowed reduction of xylose with both NADPH and NADH (see, e.g., Lee et al., *Appl. Enviorn. Microbiol.* 69:6179-6188 (2003)). Deletion of xylitol dehydrogenase increases xylitol production by blocking xylitol catabolism, but a co-substate such as glucose or glycerol is needed to regenerate NADPH for xylose reductase activity (see, e.g., Ko et al., *Appl. Environ. Microbiol.* 72:4207-4213 (2006); Ko et al., *Biotechnol. Lett.* 28:1159-1162 (2006)). Further improvements for xylitol production were made by combining deletion of the xylitol dehydrogenase gene with expression of *N. crassa* xylose reductase (see, e.g., Jeon et al., *Bioprocess Biosyst. Eng.* 35:191-198 (2012)). The xylose uptake and xylitol productivity of this strain was again further improved by expressing a xylose transporter from *Arabidopsis thaliana* (see, e.g., Jeon et al., *Bioprocess Biosyst. Eng.* 36:809-817 (2013)).

If glycerol is provided as a co-substrate, NADPH regeneration can be enhanced by expressing glucose-6-phosphate dehydrogenase and 6-phosphogluconate dehydrogenase in *C. tropicalis* (see, e.g., Ahmad et al., *Bioprocess Biosyst. Eng.* 35:199-204 (2012)). Xylitol production can also be enhanced by deleting glycerol kinase and expressing three NADPH-regenerating glycerol dehydrogenases from *S. stipitis* (see, e.g., Ahmad et al., *Bioprocess Biosyst. Eng.* 36:1279-1284 (2013)). One of the problems with producing xylitol from mixed sugar substrates is that the xylose reductase from *C. tropicalis* can convert arabinose to arabitol, a contaminant in xylitol production. To prevent this, the endogenous xylose reductase was deleted and a mutant xylose-specific xylose reductase from *N. crassa* was expressed along with bacterial arabinose assimilation enzymes (see, e.g., Yoon et al., *Biotechnol. Lett.* 33:747-753 (2011); Nair et al., *ChemBioChem* 9:1213-1215 (2008)). This minimized arabitol formation while allowing arabinose assimilation for cell growth.

*K. marxianus* is a thermotolerant yeast often found in dairy products. It can be used for xylitol production due to its high growth rate, tolerance to temperatures up to 52° C., and ability to utilize various sugars. Expression of the *N. crassa* xylose reductase alone or in conjunction with deletion of the xylitol dehydrogenase gene in *K. marxianus* led to xylitol production optimally at 42° C. (see, e.g., Zhang et al., *Bioresour. Technol.* 152:192-201 (2014)). Further improvements to xylitol production were made by testing the expression of various xylose transporters: *K. marxianus* aquaglyceroporin, *C. intermedia* glucose/xylose facilitator, or *C. intermedia* glucose/xylose symporter (see, e.g., Zhang et al., *Bioresour. Technol.* 175:642-645 (2015)). The expression of the *C. intermedia* glucose/xylose facilitator was found to be effective at increasing xylitol yield and productivity, and notably, produced the highest reported final xylitol concentration. *K. marxianus* was also used in an evolutionary adaptation experiment that resulted in a strain with improved xylose utilization and xylitol production capabilities (see, e.g., Sharma et al., *Bioprocess Biosyst. Eng.* 39:835-843 (2016)).

Two other yeast species have been genetically engineered to explore xylitol production. *D. hansenii* is another natural producer of xylitol that is osmotolerant and non-pathogenic. Xylitol production was enhanced in this species by deletion of the xylitol dehydrogenase gene (see, e.g., Pal et al., *Bioresour. Technol.* 147:449-455 (2013)). *P. pastoris* is a yeast commonly used for protein expression. It has been engineered to produce xylitol directly from glucose through the glucose-arabitol-xylulose-xylitol pathway (see, e.g., Cheng et al., *Appl. Microbiol. Biotechnol.* 98:3539-3552 (2014)). This was achieved by expressing xylitol dehydrogenase from *Gluconobacter oxydans* and the xylulose-forming arabitol dehydrogenase from *Klebsiella pneumoniae*.

It is understood that recombinant yeast provided herein or otherwise known in the art with either natural or engineered biosynthesis pathways to produce xylitol can be used as the host strain, which can improve production of xylicol when expressing a polynucleotide encoding an engineered peptide as described herein. Further metabolic engineering can be adopted to still further increase xylitol production in these host strains.

Microbial organisms having a biosynthesis pathway to produce n-butanol are known in the art (see, e.g., Kudahettige-Nilsson R L, et al., *Bioresour Technol.* 176:71-9 (2015); Xin F, et al., *Appl Environ Microbiol.*, 80(15):4771-8 (2014); Xiao H, et al., *Metab Eng.* 14(5):569-78 (2012); Zhang J, et al., *Biotechnol Lett.* 38(4):611-7 (2016); Yu L, et al. *Biotechnol Bioeng.* 112(10):2134-41 (2015); Steen, et al, *Microb Cell Fact.* 7:36 (2008); Pásztor A, et al., *Biotechnol Bioeng.*, 112(1):120-8 (2015); Shi S, et al., *Sci Rep.* 6:25675 (2016); Dellomonaco C, et al., *Nature,* 10:476(7360):355-9 (2011). In some embodiments, provided herein are recombinant yeast having at least one polynucleotide encoding an engineered peptide as described herein, as well as a biosynthesis pathway for producing n-butanol. With protection from bacterial contaminants, such as lactic acid bacteria contamination, improved production of n-butanol can be achieved. Provided herein are also methods of producing a bioderived n-butanol by culturing the recombinant yeast provided herein having an n-butanol biosynthesis pathway under conditions and for a sufficient period of time to produce n-butanol.

Butanol biosynthesis can be achieved through the acetone, butanol, and ethanol fermentation pathway (the "ABE pathway"). The products of this butanol fermentative production pathway using a solvent-producing species of the bacterium *Clostridium acetobutylicum* are six parts butanol, three parts acetone, and one part ethanol. Butanol-production pathway has been introduced to various host organisms. For instance, the pathway was expressed in *S. cerevisiae* (see, e.g., Steen et al., *Microb. Cell Fact* 7:36 (2008)) for their high growth rates and the efficiency of genetic tools.

An alternative to the use of food crops as starting material for butanol production is biomass, specifically lignocellulosic biomass. *Clostridium* spp. strains have been engineered to produce butanol, such as *C. saccharoperbutylacetonicum* (e.g., *C. saccharoperbutylacetonicum* strain ATCC 27021 or

*C. saccharoperbutylacetonicum* strain ATCC 27022) (see, e.g., U.S. Pat. No. 8,900,841. *C. cellulolyticum* was engineered to divert its native valine synthesis pathway for isobutanol production from crystalline cellulose (see, e.g., Higashide et al., *Appl. Environ. Microb.* 77:2727-2733 (2011)). *C. cellulovorans*, which natively produces butyric acid as the main metabolic product, was introduced with an aldehyde/alcohol dehydrogenase (AdhE2) to convert precursor butyryl-CoA to 1-butanol from cellulose (see, e.g., Yang et al., *Metab. Eng* 32:39-48 (2015)). 1-Butanol production from xylose was also demonstrated using *Thermoanaerobacterium saccharolyticum* (see, e.g., Bhandiwad et al., *Metab. Eng.* 21:17-25 (2014)).

It is understood that recombinant yeast provided herein or otherwise known in the art with either natural or engineered biosynthesis pathways to produce n-butanol can be used as the host strain, which can improve production of n-butanol when expressing a polynucleotide encoding an engineered peptide as described herein. Further metabolic engineering can be adopted to still further increase n-butanol production in these host strains.

Microbial organisms having a biosynthesis pathway to produce isobutanol are known in the art (see, e.g., Felpeto-Santero C, et al., *AMB Express* 5(1):119 (2015)). In some embodiments, provided herein are recombinant yeast having at least one polynucleotide encoding an engineered peptide as described herein, as well as a biosynthesis pathway for producing isobutanol. With protection from bacterial contaminants, such as lactic acid bacteria contamination, improved production of isobutanol can be achieved. Provided herein are also methods of producing a bioderived ethanol by culturing the recombinant yeast provided herein having an isobutanol biosynthesis pathway under conditions and for a sufficient period of time to produce isobutanol.

Isobutanol, also a biofuel candidate, has been produced in recombinant microorganisms expressing a heterologous, five-step metabolic pathway (see, e.g., WO/2007/050671, WO/2008/098227, and WO/2009/103533). Other pathways for isobutanol production are also known in the art (see e.g., U.S. Pat. No. 8,530,226 B2; U.S. Pat. No. 8,114,641 B2; U.S. Pat. No. 8,975,049 B2). The recombinant microorganism including a pathway for the production of isobutanol from five-carbon (pentose) sugars including xylose is also known in the art (see, e.g., WO 2012173659; WO 2011153144). The recombinant microorganism can be engineered to express a functional exogenous xylose isomerase. Exogenous xylose isomerases functional in yeast are known in the art (see, e.g., US2006/0234364). The exogenous xylose isomerase gene can be operatively linked to promoter and terminator sequences that are functional in the yeast cell. Various methods of genetic engineering to improve isobutanol production are also known in the art (see, e.g., Avalos et al., *Nature Biotechnology* 31, 335-41 (2013)).

For example, recombinant *S. cerevisiae* was known to produce isobutanol (see, e.g., US20130035515, Brat et al., *FEMS yeast research* 13.2 (2013): 241-244; Lee, Won-Heong et al. *Bioprocess and biosystems engineering* 35.9 (2012): 1467-1475). Simultaneous overexpression of an optimized, cytosolically localized valine biosynthesis pathway together with overexpression of xylose isomerase XylA from *C. phytofermentans*, transaldolase Tal1 and xylulokinase Xks1 enabled recombinant *S. cerevisiae* cells to complement the valine auxotrophy of ilv2,3,5 triple deletion mutants for growth on D-xylose as the sole carbon source. Moreover, after additional overexpression of ketoacid decarboxylase Aro10 and alcohol dehydrogenase Adh2, the cells were able to ferment D-xylose directly to isobutanol.

It is understood that recombinant yeast provided herein or otherwise known in the art with either natural or engineered biosynthesis pathways to produce isobutanol can be used as the host strain, which can improve production of isobutanol when expressing a polynucleotide encoding an engineered peptide as described herein. Further metabolic engineering can be adopted to still further increase isobutanol production in these host strains.

Microbial organisms having a biosynthesis pathway to produce isopropanol are known in the art (see, e.g., Hanai T, et al., *Appl Environ Microbiol.*, 73(24):7814-8 (2007). In some embodiments, provided herein are recombinant yeast having at least one polynucleotide encoding an engineered peptide as described herein, as well as a biosynthesis pathway for producing isopropanol. With protection from bacterial contaminants, such as lactic acid bacteria contamination, improved production of isopropanol can be achieved. Provided herein are also methods of producing a bioderived isopropanol by culturing the recombinant yeast provided herein having an isopropanol biosynthesis pathway under conditions and for a sufficient period of time to produce isopropanol.

Production of isopropanol has been observed in recombinant *Lactobacillus* host cells (e.g., *Lactobacillus reuteri*) engineered to have an isopropanol pathway and produce increased amounts of isopropanol (see, e.g., WO2013178699 A1). Direct isopropanol production from cellobiose by engineered *Escherichia coli* using a synthetic pathway was also observed (see, e.g., Soma et al., *Journal of bioscience and bioengineering* 114.1: 80-85 (2012)).

It is understood that recombinant yeast provided herein or otherwise known in the art with either natural or engineered biosynthesis pathways to produce isopropanol can be used as the host strain, which can improve production of isopropanol when expressing a polynucleotide encoding an engineered peptide as described herein. Further metabolic engineering can be adopted to still further increase isopropanol production in these host strains.

Microbial organisms having a biosynthesis pathway to produce arabitol are known in the art. Arabitol can be produced by yeasts in the processes of bioconversion or biotransformation of waste materials from agriculture, the forest industry (L-arabinose, glucose) and the biodiesel industry (glycerol). There are native yeasts from the genera *Candida, Pichia*, Debaryomyces and *Zygosaccharomyces* as well as genetically modified strains of *Saccharomyces cerevisiae* that are able to utilize biomass hydrolysates to effectively produce L- or D-arabitol (see, e.g., Kordowska-Wiater, *Journal of Applied Microbiology* 119, 303-314 (2015); Nozaki et al., *Biosci. Biotechnol. Biochem.*, 67(9): 1923-29 (2003)). In some embodiments, provided herein are recombinant yeast having at least one polynucleotide encoding an engineered peptide as described herein, as well as a biosynthesis pathway for producing arabitol. With protection from bacterial contaminants, such as lactic acid bacteria contamination, improved production of arabitol can be achieved. Provided herein are also methods of producing a bioderived arabitol by culturing the recombinant yeast provided herein having an arabitol biosynthesis pathway under conditions and for a sufficient period of time to produce arabitol.

For example, the *Zygocaccharomyces rouxxii* NRRL 27,624 strain is known to produce D-arabitol as the main metabolic product from glucose (see, e.g., Saha et al., *J Ind Microbiol Biotechnol* 34:519-523 (2007)). Additionally, *Candida maltosa* has been shown to produce D-arabitol from D-xylulose by a xylulose reductase (see, e.g., Cheng et al., *Microbial. Cell Factories*, 10:5 (2011)). Production of arabitol was also found to be improved by the addition of xylose with glycerol in the yeast species within the genus of *Debaryomyces, Geotrichum* and *Metschnikowia* (see, e.g., International Application Publication WO 2012/011962 (2012)).

It is understood that recombinant yeast provided herein or otherwise known in the art with either natural or engineered biosynthesis pathways to produce arabitol can be used as the host strain, which can improve production of arabitol when expressing a polynucleotide encoding an engineered peptide as described herein. Further metabolic engineering can be adopted to still further increase arabitol production in these host strains.

Microbial organisms having a biosynthesis pathway to produce ethyl acetate are known in the art (see, e.g., Morrissey J P, et al., *Yeast,* 32(1):3-16 (2015)). In some embodiments, provided herein are recombinant yeast having at least one polynucleotide encoding an engineered peptide as described herein, as well as a biosynthesis pathway for producing ethyl acetate. With protection from bacterial contaminants, such as lactic acid bacteria contamination, improved production of ethyl acetate can be achieved. Provided herein are also methods of producing a bioderived ethyl acetate by culturing the recombinant yeast provided herein having an ethyl acetate biosynthesis pathway under conditions and for a sufficient period of time to produce ethyl acetate.

The ability of yeasts for producing larger amounts of this ester is known for a long time and can be applied to large-scale ester production from renewable raw materials. *P. anomala, C. utilis,* and *K. marxianus* are yeasts which convert sugar into ethyl acetate with a high yield (see, e.g., Loser et al., *Appl Microbiol Biotechnol* (2014) 98:5397-5415). Synthesis of much ethyl acetate requires oxygen, which is usually supplied by aeration. Ethyl acetate is highly volatile so that aeration results in its phase transfer and stripping. This stripping process cannot be avoided, but requires adequate handling during experimentation and offers a chance for a cost-efficient process-integrated recovery of the synthesized ester.

It is understood that recombinant yeast provided herein or otherwise known in the art with either natural or engineered biosynthesis pathways to produce ethyl acetate can be used as the host strain, which can improve production of ethyl acetate when expressing a polynucleotide encoding an engineered peptide as described herein. Further metabolic engineering can be adopted to still further increase ethyl acetate production in these host strains.

Microbial organisms having a biosynthesis pathway to produce phenyl-ethyl alcohol are known in the art (see, e.g., Kim B, et al., *Biotechnol Bioeng.* 111(1):115-24 (2014)). In some embodiments, provided herein are recombinant yeast having at least one polynucleotide encoding an engineered peptide as described herein, as well as a biosynthesis pathway for producing phenyl-ethyl alcohol. With protection from bacterial contaminants, such as lactic acid bacteria contamination, improved production of phenyl-ethyl alcohol can be achieved. Provided herein are also methods of producing a bioderived phenyl-ethyl alcohol by culturing the recombinant yeast provided herein having an phenyl-ethyl alcohol biosynthesis pathway under conditions and for a sufficient period of time to produce phenyl-ethyl alcohol.

Phenyl-ethyl alcohol a colorless, transparent, slightly viscous liquid that can be produced by microbial organisms. Phenyl-ethyl alcohol has been found in a number of natural essential oils, in food, spices and tobacco, and in undistilled alcoholic beverages, beers and wines. It prevents or retards bacterial growth, and thus protects cosmetics and personal care products from spoilage. Phenyl-ethyl alcohol also imparts a fragrance to a product.

It is understood that recombinant yeast provided herein or otherwise known in the art with either natural or engineered biosynthesis pathways to produce phenyl-ethyl alcohol can be used as the host strain, which can improve production of phenyl-ethyl alcohol when expressing a polynucleotide encoding an engineered peptide as described herein. Further metabolic engineering can be adopted to still further increase phenyl-ethyl alcohol production in these host strains.

Microbial organisms having a biosynthesis pathway to produce 2-methyl-butanol are known in the art (see, e.g., U.S. Pat. No. 8,114,641 B2; U.S. Pat. No. 8,975,049 B2). In some embodiments, provided herein are recombinant yeast having at least one polynucleotide encoding an engineered peptide as described herein, as well as a biosynthesis pathway for producing 2-methyl-butanol. With protection from bacterial contaminants, such as lactic acid bacteria contamination, improved production of 2-methyl-butanol can be achieved. Provided herein are also methods of producing a bioderived 2-methyl-butanol by culturing the recombinant yeast provided herein having an 2-methyl-butanol biosynthesis pathway under conditions and for a sufficient period of time to produce 2-methyl-butanol.

2-methyl-butanol can be used as a solvent and an intermediate in the manufacture of other chemicals. 2-methyl-butanol also has applications in fuel and lubricating oil additives, flotation aids, manufacture of corrosion inhibitors, pharmaceuticals, paint solvent, and extraction agent.

It is understood that recombinant yeast provided herein or otherwise known in the art with either natural or engineered biosynthesis pathways to produce 2-methyl-butanol can be used as the host strain, which can improve production of 2-methyl-butanol when expressing a polynucleotide encoding an engineered peptide as described herein. Further metabolic engineering can be adopted to still further increase 2-methyl-butanol production in these host strains.

Microbial organisms having a biosynthesis pathway to produce 3-methyl-butanol are known in the art (see, e.g., U.S. Pat. No. 8,114,641 B2; U.S. Pat. No. 8,975,049 B2; U.S. Pat. No. 7,985,567 B2). In some embodiments, provided herein are recombinant yeast having at least one polynucleotide encoding an engineered peptide as described herein, as well as a biosynthesis pathway for producing 3-methyl-butanol. With protection from bacterial contaminants, such as lactic acid bacteria contamination, improved production of ethanol can be achieved. Provided herein are also methods of producing a bioderived 3-methyl-butanol by culturing the recombinant yeast provided herein having an 3-methyl-butanol biosynthesis pathway under conditions and for a sufficient period of time to produce 3-methyl-butanol.

3-methyl-butanol (also known as isoamyl alcohol or isopentyl alcohol) is a clear, colorless alcohol. 3-methyl-butanol is a main ingredient in the production of banana oil, an ester found in nature and also produced as a flavouring in industry. It is also the main ingredient of Kovac's reagent, used for the bacterial diagnostic indole test. 3-methyl-butanol is also used as an antifoaming agent in the chloroform:isoamyl alcohol reagent.

It is understood that recombinant yeast provided herein or otherwise known in the art with either natural or engineered biosynthesis pathways to produce 3-methyl-butanol can be used as the host strain, which can improve production of 3-methyl-butanol when expressing a polynucleotide encoding an engineered peptide as described herein. Further metabolic engineering can be adopted to still further increase 3-methyl-butanol production in these host strains.

Microbial organisms having a biosynthesis pathway to produce a combination of carbonyl compounds, alcohols, acetals, acids, esters and nitrogen compounds found in wine, beer, or whiskey are known in the art. In some embodiments, provided herein are recombinant yeast having at least one polynucleotide encoding an engineered peptide as described herein, as well as biosynthesis pathways for producing a combination of carbonyl compounds, alcohols, acetals, acids, esters and nitrogen compounds found in wine, beer, or whiskey. With protection from bacterial contaminants, such as lactic acid bacteria contamination, improved production of the carbonyl compounds, alcohols, acetals, acids, esters and nitrogen compounds found in wine, beer, or whiskey can be achieved. Provided herein are also methods of producing a combination of carbonyl compounds, alcohols, acetals, acids, esters and nitrogen compounds found in wine, beer, or whiskey by culturing the recombinant yeast provided herein having such biosynthesis pathways under conditions and for a sufficient period of time to produce the combination.

The chemical composition of alcoholic beverages, such as wine, beer, or whiskey are well known in the art (see, e.g., IARC Working Group on the Evaluation of Carcinogenic Risks to Humans. Alcohol Drinking. Lyon (FR): International Agency for Research on *Cancer;* 1988. (IARC Monographs on the Evaluation of Carcinogenic Risks to Humans, No. 44.) 3, Chemical Composition of Alcoholic Beverages, Additives and Contaminants. Available from: ncbi.nlm.nih.gov/books/NBK531662/). Methods and techniques for producing wine, beer and whiskey are well known in the art, including methods and techniques using recombinant yeast for production of wine, beer and whiskey (see, e.g., Fleet, *FEMS Yeast Research,* 8(7):979-995 (2008); Gibson et al., *FEMS Yeast Research,* 17(4):FOX038 (2017); la Grange-Nel, Characterisation and Improvement of Whiskey Yeast, Thesis, University of Stellenbosch, April 2003).

It is understood that recombinant yeast provided herein or otherwise known in the art with either natural or engineered biosynthesis pathways to produce a combination of carbonyl compounds, alcohols, acetals, acids, esters and nitrogen compounds found in wine, beer, or whiskey can be used as the host strain, which can improve production of the combination when expressing a polynucleotide encoding an engineered peptide as described herein.

Methods for constructing and testing the expression levels of an engineered peptide provided herein in a recombinant yeast can be performed, for example, by recombinant and detection methods well known in the art. Such methods can be found described in, for example, Sambrook et al., *Molecular Cloning: A Laboratory Manual,* Third Ed., Cold Spring Harbor Laboratory, New York (2001); and Ausubel et al., *Current Protocols in Molecular Biology,* John Wiley and Sons, Baltimore, Md. (1999).

Culture Medium

Provided herein is a culture medium having an engineered peptide (e.g., engineered persulcatusin or engineered pediocin PA-1) described herein. Such a culture medium can be generated during cultivation of the recombinant yeast described herein. Alternatively or in addition, the culture medium can be generated by the addition of the engineered peptide (e.g., engineered persulcatusin or engineered pediocin PA-1) to any culture medium that is susceptible to contamination by lactic acid bacteria. Accordingly, in some embodiments, the culture medium can be a food or beverage, such as wine, beer or whiskey. In some embodiments, the culture medium containing the engineered peptide (e.g., engineered persulcatusin or engineered pediocin PA-1) described herein was used to produce a bioderived compound as described herein. Thus, the culture medium can be industrial cell culture medium that will be subjected to further processing in order to isolate the bioderived compound found in the culture medium.

In some embodiments, provided herein is a culture medium containing an engineered peptide (e.g., engineered persulcatusin or engineered pediocin PA-1) described herein and a different antibacterial peptide. Such a different peptide can have complementary activity against the engineered peptide (e.g., engineered persulcatusin or engineered pediocin PA-1) described herein. In other words, the culture medium can include a peptide that has antibacterial activity against different bacteria as compared to the engineered peptide (e.g., engineered persulcatusin or engineered pediocin PA-1) described herein. Exemplary peptides are described herein, including those peptides described in Example V. Accordingly, in some embodiments, provided herein is a culture medium having an engineered persulcatusin described herein as well as pediocin PA-1 (SEQ ID NO: 36) or a variant or functional fragment thereof. In some embodiments, provided herein is a culture medium having an engineered persulcatusin described herein or a functional fragment thereof as well as an engineered pediocin PA-1 described herein or a functional fragment thereof. Additionally, in some embodiments, provided herein is a culture medium having at least two, at least three, at least four or at least five different peptides that have antibacterial activity, including for example the engineered persulcatusin described herein and/or the engineered pediocin PA-1 described herein, and one or more peptides described in Example V. Accordingly, in some embodiments, provided herein is a culture medium having: (a) persulcatusin (SEQ ID NO: 1) or a variant or a functional fragment thereof and (b) pediocin PA-1 (SEQ ID NO: 36) or a variant or functional fragment thereof.

In some embodiments, the culture medium containing an engineered peptide described herein also contains a bioderived compound as described herein. For example, in some embodiments, the culture medium includes the bioderived compound selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey. Accordingly, in some embodiments, a culture medium includes an engineered peptide described herein and ethanol. In some embodiments, a culture medium includes an engineered peptide described herein and xylitol. In some embodiments, a culture medium includes an engineered peptide described herein and n-butanol. In some embodiments, a culture medium includes an engineered peptide described herein and isobutanol. In some embodiments, a culture medium includes an engineered peptide described herein and isopropanol. In some embodiments, a culture medium includes an engineered peptide described herein and arabitol. In some embodiments, a culture medium includes an engineered peptide described herein and ethyl acetate. In some embodiments, a culture medium includes an engineered peptide described herein and phenyl-ethyl alcohol. In some embodiments, a culture medium includes an engineered peptide described herein and 2-methyl-butanol. In some embodiments, a culture medium includes an engineered peptide described herein and 3-methyl-butanol. In some embodiments, a culture medium includes an engineered peptide described herein and combination of carbonyl compounds, alcohols, acetals, acids, esters and nitrogen compounds found in wine, beer, or whiskey.

Methods of Culturing Yeast and Uses of Engineered Peptides

Provided herein is a method for inhibiting bacterial growth in a yeast culture. Such a method can include culturing a recombinant yeast described herein, wherein the yeast expresses an engineered peptide (e.g., engineered persulcatusin or engineered pediocin PA-1) described herein. Also provided herein is a method for inhibiting bacterial growth in a yeast culture that includes culturing yeast in the presence of an engineered peptide (e.g., engineered persulcatusin or engineered pediocin PA-1) described herein. The presence of the engineered peptide can be due to culturing a recombinant yeast described herein, which can secrete the engineered peptide into the culture medium. Alternatively or in addition, the presence of the engineered peptide can be due to the addition of an engineered peptide to the culture medium that is susceptible to contamination by lactic acid bacteria. For example, in some embodiments, the method includes addition of a composition containing the engineered peptide described herein to the culture medium. Such a composition can contain isolated or purified forms of the engineered peptide described herein.

Also provided herein is a method for culturing a yeast that includes co-culturing a yeast in the presence of a recombinant yeast described herein. Such a method can include, for example, culturing a yeast to produce a bioderived compound as described herein, wherein the culture also includes a recombinant yeast that expresses an engineered peptide (e.g., engineered persulcatusin or engineered pediocin PA-1) described herein for inhibiting the growth of contaminating bacteria (e.g., lactic acid bacteria). Although the recombinant yeast itself may not produce the bioderived compound itself, the ability of the recombinant yeast to inhibit the growth of contaminating bacteria (e.g., lactic acid bacteria) and improve the production of the bioderived compound. Similarly, also provided is a method for culturing a yeast that includes culturing the yeast in the presence of an engineered peptide described herein. For example, the presence of the engineered peptide can be due to the addition of an engineered peptide to the culture medium that is susceptible to contamination by lactic acid bacteria. For example, in some embodiments, the method includes addition of a composition containing the engineered peptide described herein to the culture medium. Such a composition can contain isolated or purified forms of the engineered peptide described herein. In some embodiments, the method described herein includes fermentation.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719. Any of these conditions can be employed with the non-naturally occurring microbial organisms as well as other anaerobic conditions well known in the art. Under such anaerobic or substantially anaerobic conditions, the producer strains can synthesize the desired product at intracellular concentrations of 5-10 mM or more as well as all other concentrations exemplified herein. It is understood that, even though the above description refers to intracellular concentrations, the producing microbial organisms can produce the desired product intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary fed-batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a fed-batch fermentation process, the time period for the fermentation is generally in the range of several hours to several days, for example, 8 to 24 hours, or 1, 2, 3, 4 or 5 days, or up to two weeks, depending on the desired culture conditions. The pH can be controlled or not, as desired, in which case a culture in which pH is not controlled will typically decrease to pH 3-6 by the end of the run. In some embodiment, the initial pH can first decrease and then increase during the cultivation period. In one embodiment, the initial pH of the medium is around 6, and during the cultivation period, the pH decreased first to 5.5 and later increased to around 6.5. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, usually with relatively high sugar concentration, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

The culture conditions can include, for example, liquid culture procedures as well as fermentation and other large scale culture procedures. As described herein, particularly useful yields of the biosynthetic products can be obtained under anaerobic or substantially anaerobic culture conditions.

The culture conditions described herein can be scaled up and grown continuously for manufacturing of a desired product. All of these processes are well known in the art. Fermentation procedures are particularly useful for the biosynthetic production of commercial quantities of a desired product. Generally, and as with non-continuous culture procedures, the continuous and/or near-continuous production includes culturing the microbial organisms provided herein in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism provided herein is for a sufficient period of time to produce a sufficient amount of product for a desired purpose.

In some embodiments, a method described herein can include a small molecule antibiotic in addition to an engineered peptide (e.g., engineered persulcatusin or engineered pediocin PA-1) described herein. Thus, in some embodiments, a method described herein includes culturing a yeast or recombinant yeast described herein in the presence of a small molecule antibiotic, such as ampicillin, chloramphenicol, clarithromycin, erythromycin, monensin, penicillin, streptomycin, tetracyclines, tylosin, virginiamycin, erythromycin, or streptomycin. The presence of such a small molecule antibiotic can be to complement the antibacterial activity of an engineered peptide (e.g., engineered persulcatusin or engineered pediocin PA-1) described herein. Accordingly, in some embodiments, the method includes culturing in the presence of ampicillin. In some embodiments, the method includes culturing in the presence of chloramphenicol. In some embodiments, the method includes culturing in the presence of clarithromycin. In some embodiments, the method includes culturing in the presence of erythromycin. In some embodiments, the method includes culturing in the presence of monensin. In some embodiments, the method includes culturing in the presence of penicillin. In some embodiments, the method includes culturing in the presence of streptomycin. In some embodiments, the method includes culturing in the presence of tetracyclines. In some embodiments, the method includes culturing in the presence of virginiamycin. In some embodiments, the method includes culturing in the presence of tylosin. In some embodiments, the method includes culturing in the presence of erythromycin. In some embodiments, the method includes culturing in the presence of streptomycin.

In some embodiments, a method described herein includes culturing to produce a bioderived compound described herein. As described herein, a recombinant yeast that can express an engineered peptide (e.g., engineered persulcatusin or engineered pediocin PA-1) described herein can also produce a desired bioderived compound, such as ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey. Accordingly, in some embodiments, a method described herein include culturing a yeast or recombinant yeast to produce a bioderived compound selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey.

Also provided herein is the use of an engineered peptide (e.g., engineered persulcatusin or engineered pediocin PA-1) described herein for the production of a bioderived compound. Similarly, provided herein is the use of a recombinant yeast described herein in the production of a bioderived compound. The use can be for the production of a bioderived compound selected from ethanol, xylitol, n-butanol, isobutanol, isopropanol, arabitol, ethyl acetate, phenyl-ethyl alcohol, 2-methyl-butanol, 3-methyl-butanol and a combination of carbonyl compounds, alcohols, acetals, acids, esters and nitrogen compounds found in wine, beer, or whiskey. According, in some embodiments, provided herein is the use of an engineered peptide (e.g., engineered persulcatusin or engineered pediocin PA-1) or recombinant yeast described herein for production of ethanol. In some embodiments, provided herein is the use of an engineered peptide (e.g., engineered persulcatusin or engineered pediocin PA-1) or recombinant yeast described herein for production of xylitol. In some embodiments, provided herein is the use of an engineered peptide (e.g., engineered persulcatusin or engineered pediocin PA-1) or recombinant yeast described herein for production of n-butanol. In some embodiments, provided herein is the use of an engineered peptide (e.g., engineered persulcatusin or engineered pediocin PA-1) or recombinant yeast described herein for production of isobutanol. In some embodiments, provided herein is the use of an engineered peptide (e.g., engineered persulcatusin or engineered pediocin PA-1) or recombinant yeast described herein for production of isopropanol. In some embodiments, provided herein is the use of an engineered peptide (e.g., engineered persulcatusin or engineered pediocin PA-1) or recombinant yeast described herein for production of arabitol. In some embodiments, provided herein is the use of an engineered peptide (e.g., engineered persulcatusin or engineered pediocin PA-1) or recombinant yeast described herein for production of ethyl acetate. In some embodiments, provided herein is the use of an engineered peptide (e.g., engineered persulcatusin or engineered pediocin PA-1) or recombinant yeast described herein for production of phenyl-ethyl alcohol. In some embodiments, provided herein is the use of an engineered peptide (e.g., engineered persulcatusin or engineered pediocin PA-1) or recombinant yeast described herein for production of 2-methyl-butanol. In some embodiments, provided herein is the use of an engineered peptide (e.g., engineered persulcatusin or engineered pediocin PA-1) or recombinant yeast described herein for production of 3-methyl-butanol. In some embodiments, provided herein is the use of an engineered peptide (e.g., engineered persulcatusin or engineered pediocin PA-1) or recombinant yeast described herein for production of a combination of carbonyl compounds, alcohols, acetals, acids, esters and nitrogen compounds found in wine, beer, or whiskey.

SEQUENCES

The sequences in Table 1 illustrate amino acid sequences and nucleotide sequences that can be used to generate the compositions and perform the methods described herein. As needed, an RNA sequence can be readily deduced from the DNA sequence.

TABLE 1

| SEQ ID NO: | Description | Amino Acid or Nucleic Acid Sequence |
|---|---|---|
| 1. | Wild-type persulcatusin [Ixodes persulcatus] | GFGCPFNQGACHRHCRSIGRRGGYCAGLFKQTCTCYSR |
| 2. | Engineered persulcatusin with [F6A] | GFGCPANQGACHRHCRSIGRRGGYCAGLFKQTCTCYSR |
| 3. | Engineered persulcatusin with [R13A] | GFGCPFNQGACHAHCRSIGRRGGYCAGLFKQTCTCYSR |
| 4. | Engineered persulcatusin with [R16A] | GFGCPFNQGACHRHCASIGRRGGYCAGLFKQTCTCYSR |
| 5. | Engineered persulcatusin with [R20A] | GFGCPFNQGACHRHCRSIGARGGYCAGLFKQTCTCYSR |
| 6. | Engineered persulcatusin with [R21A] | GFGCPFNQGACHRHCRSIGRAGGYCAGLFKQTCTCYSR |
| 7. | Engineered persulcatusin with [L28A] | GFGCPFNQGACHRHCRSIGRRGGYCAGAFKQTCTCYSR |
| 8. | Engineered persulcatusin with [F29A] | GFGCPFNQGACHRHCRSIGRRGGYCAGLAKQTCTCYSR |
| 9. | Engineered persulcatusin with [R38A] | GFGCPFNQGACHRHCRSIGRRGGYCAGLFKQTCTCYSA |
| 10. | Engineered persulcatusin with [R13S] | GFGCPFNQGACHSHCRSIGRRGGYCAGLFKQTCTCYSR |
| 11. | Engineered persulcatusin with [R21G] | GFGCPFNQGACHRHCRSIGRGGGYCAGLFKQTCTCYSR |
| 12. | Engineered persulcatusin with [A26D] | GFGCPFNQGACHRHCRSIGRRGGYCDGLFKQTCTCYSR |
| 13. | Engineered persulcatusin with [F6V/R13S] | GFGCPVNQGACHSHCRSIGRRGGYCAGLFKQTCTCYSR |
| 14. | Engineered persulcatusin with [N7D/R16S] | GFGCPFDQGACHRHCSSIGRRGGYCAGLFKQTCTCYSR |
| 15. | Engineered persulcatusin with [N7D/F29L] | GFGCPFDQGACHRHCRSIGRRGGYCAGLLKQTCTCYSR |
| 16. | Engineered persulcatusin with [G9D/H14Q] | GFGCPFNQDACHRQCRSIGRRGGYCAGLFKQTCTCYSR |
| 17. | Engineered persulcatusin with [G9D/R20S] | GFGCPFNQDACHRHCRSIGSRGGYCAGLFKQTCTCYSR |
| 18. | Engineered persulcatusin with [R13S/R16K] | GFGCPFNQGACHSHCKSIGRRGGYCAGLFKQTCTCYSR |

TABLE 1-continued

| SEQ ID NO: | Description | Amino Acid or Nucleic Acid Sequence |
|---|---|---|
| 19. | Engineered persulcatusin with [R13S/I18N] | GFGCPFNQGACHSHCRSNGRRGGYCAGLFKQTCTCYSR |
| 20. | Engineered persulcatusin with [R13S/R20T] | GFGCPFNQGACHSHCRSIGTRGGYCAGLFKQTCTCYSR |
| 21. | Engineered persulcatusin with [R13S/R21G] | GFGCPFNQGACHSHCRSIGRGGGYCAGLFKQTCTCYSR |
| 22. | Engineered persulcatusin with [R13S/R21S] | GFGCPFNQGACHSHCRSIGRSGGYCAGLFKQTCTCYSR |
| 23. | Engineered persulcatusin with [R13S/A26D] | GFGCPFNQGACHSHCRSIGRRGGYCDGLFKQTCTCYSR |
| 24. | Engineered persulcatusin with [R13S/L28M] | GFGCPFNQGACHSHCRSIGRRGGYCAGMFKQTCTCYSR |
| 25. | Engineered persulcatusin with [R16S/R20S] | GFGCPFNQGACHRHCSSIGSRGGYCAGLFKQTCTCYSR |
| 26. | Engineered persulcatusin with [R16G/F29V] | GFGCPFNQGACHRHCGSIGRRGGYCAGLVKQTCTCYSR |
| 27. | Engineered persulcatusin with [R20S/R21G] | GFGCPFNQGACHRHCRSIGSGGGYCAGLFKQTCTCYSR |
| 28. | Engineered persulcatusin with [F6L/N7D/H14Q] | GFGCPLDQGACHRQCRSIGRRGGYCAGLFKQTCTCYSR |
| 29. | Engineered persulcatusin with [F6L/G9D/H14Q] | GFGCPLNQDACHRQCRSIGRRGGYCAGLFKQTCTCYSR |
| 30. | Engineered persulcatusin with [F6L/G9D/R20K] | GFGCPLNQDACHRHCRSIGKRGGYCAGLFKQTCTCYSR |
| 31. | Engineered persulcatusin with [F6V/R13S/A26D] | GFGCPVNQGACHSHCRSIGRRGGYCDGLFKQTCTCYSR |
| 32. | Engineered persulcatusin with [N7D/H14F/R16S] | GFGCPFDQGACHRFCSSIGRRGGYCAGLFKQTCTCYSR |
| 33. | Engineered persulcatusin with [G9D/I18F/F29L] | GFGCPFNQDACHRHCRSFGRRGGYCAGLLKQTCTCYSR |
| 34. | Engineered persulcatusin with [F6L/G9D/R13S/H14Q] | GFGCPLNQDACHSQCRSIGRRGGYCAGLFKQTCTCYSR |
| 35. | Engineered persulcatusin with [F6S/R13S/R16K/I18V] | GFGCPSNQGACHSHCKSVGRRGGYCAGLFKQTCTCYSR |
| 36. | Pediocin PA-1 from [*Pediococcus acidilactici*] | KYYGNGVTCGKHSCSVDWGKATTCIINNGAMAWATGGHQGNHKC |
| 37. | Wild-type persulcatusin [*Ixodes persulcatus*] | GGTTTTGGTTGTCCATTCAATCAAGGTGCTTGTCATAGACATTGCAGATCCATTGGTAGAAGAGGCGGTTATTGTGCTGGTTTGTTTAAGCAAACTTGTACCTGCTACTCCAGGTGA |
| 38. | Engineered persulcatusin with [F6A] | GGTTTTGGTTGTCCAGCTAATCAAGGTGCTTGTCATAGACATTGCAGATCCATTGGTAGAAGAGGCGGTTATTGTGCTGGTTTGTTTAAGCAAACTTGTACCTGCTACTCCAGGTGA |
| 39. | Engineered persulcatusin with [R13A] | GGTTTTGGTTGTCCATTCAATCAAGGTGCTTGTCATGCTCATTGCAGATCCATTGGTAGAAGAGGCGGTTATTGTGCTGGTTTGTTTAAGCAAACTTGTACCTGCTACTCCAGGTGA |
| 40. | Engineered persulcatusin with [R16A] | GGTTTTGGTTGTCCATTCAATCAAGGTGCTTGTCATAGACATTGCGCTTCCATTGGTAGAAGAGGCGGTTATTGTGCTGGTTTGTTTAAGCAAACTTGTACCTGCTACTCCAGGTGA |
| 41. | Engineered persulcatusin with [R20A] | GGTTTTGGTTGTCCATTCAATCAAGGTGCTTGTCATAGACATTGCAGATCCATTGGTGCTAGAGGCGGTTATTGTGCTGGTTTGTTTAAGCAAACTTGTACCTGCTACTCCAGGTGA |

TABLE 1-continued

| SEQ ID NO: | Description | Amino Acid or Nucleic Acid Sequence |
|---|---|---|
| 42. | Engineered persulcatusin with [R21A] | GGTTTTGGTTGTCCATTCAATCAAGGTGCTTGTCATAGAC<br>ATTGCAGATCCATTGGTAGAGCTGGCGGTTATTGTGCTGG<br>TTTGTTTAAGCAAACTTGTACCTGCTACTCCAGGTGA |
| 43. | Engineered persulcatusin with [L28A] | GGTTTTGGTTGTCCATTCAATCAAGGTGCTTGTCATAGAC<br>ATTGCAGATCCATTGGTAGAAGAGGCGGTTATTGTGCTGG<br>TGCTTTTAAGCAAACTTGTACCTGCTACTCCAGGTGA |
| 44. | Engineered persulcatusin with [F29A] | GGTTTTGGTTGTCCATTCAATCAAGGTGCTTGTCATAGAC<br>ATTGCAGATCCATTGGTAGAAGAGGCGGTTATTGTGCTGG<br>TTTGGCTAAGCAAACTTGTACCTGCTACTCCAGGTGA |
| 45. | Engineered persulcatusin with [R38A] | GGTTTTGGTTGTCCATTCAATCAAGGTGCTTGTCATAGAC<br>ATTGCAGATCCATTGGTAGAAGAGGCGGTTATTGTGCTGG<br>TTTGTTTAAGCAAACTTGTACCTGCTACTCCGCTTGA |
| 46. | Engineered persulcatusin with [R13S] | GGTTTTGGTTGTCCATTCAATCAAGGTGCTTGTCATAGTC<br>ATTGCAGATCCATTGGTAGAAGAGGCGGTTATTGTGCTGG<br>TTTGTTTAAGCAAACTTGTACCTGCTACTCCAGGTGA |
| 47. | Engineered persulcatusin with [R21G] | GGTTTTGGTTGTCCATTCAATCAAGGTGCTTGTCATAGAC<br>ATTGCAGATCCATTGGTAGAGGAGGCGGTTATTGTGCTGG<br>TTTGTTTAAGCAAACTTGTACCTGCTACTCCAGGTGA |
| 48. | Engineered persulcatusin with [A26D] | GGTTTTGGTTGTCCATTCAATCAAGGTGCTTGTCATAGAC<br>ATTGCAGATCCATTGGTAGAAGAGGCGGTTATTGTGATGG<br>TTTGTTTAAGCAAACTTGTACCTGCTACTCCAGGTGA |
| 49. | Engineered persulcatusin with [F6V/R13S] | GGTTTTGGTTGCCCAGTCAATCAAGGTGCTTGTCATAGTC<br>ATTGTAGATCCATTGGTAGAAGAGGCGGATATTGTGCTGG<br>TTTGTTTAAGCAAACTTGTACCTGCTACTCCAGGTGA |
| 50. | Engineered persulcatusin with [N7D/R16S] | GGTTTTGGTTGTCCATTCGATCAAGGCGCTTGTCATAGAC<br>ATTGCAGTTCCATTGGTAGAAGAGGCGGTTATTGTGCTGG<br>TTTGTTTAAGCAAACTTGTACCTGCTACTCCAGGTGA |
| 51. | Engineered persulcatusin with [N7D/F29L] | GGTTTTGGTTGTCCATTCGATCAAGGTGCTTGTCATAGAC<br>ATTGCAGATCCATTGGTAGAAGAGGCGGTTATTGTGCTGG<br>TTTGCTTAAGCAAACTTGTACCTGCTACTCTAGGTGA |
| 52. | Engineered persulcatusin with [G9D/H14Q] | GGCTTTGGTTGTCCATTCAATCAAGATGCTTGTCATAGAC<br>AATGCAGATCCATTGGTAGAAGAGGCGGTTATTGTGCTGG<br>TTTGTTTAAGCAAACATGTACCTGCTACTCCAGGTGA |
| 53. | Engineered persulcatusin with [G9D/R20S] | GGTTTTGGTTGCCCATTCAATCAAGATGCTTGTCATAGAC<br>ATTGCAGATCCATTGGTAGTAGAGGCGGTTATTGTGCTGG<br>TTTGTTTAAGCAAACTTGTACCTGCTACTCCAGGTGA |
| 54. | Engineered persulcatusin with [R13S/R16K] | GGTTTTGGTTGTCCATTCAATCAAGGTGCTTGTCATAGTC<br>ATTGCAAATCCATTGGTAGAAGAGGCGGTTATTGTGCTGG<br>TTTGTTTAAGCAAACTTGTACCTGCTACTCCAGGTGA |
| 55. | Engineered persulcatusin with [R13S/I18N] | GGTTTTGGTTGTCCATTCAATCAAGGTGCTTGTCATAGTC<br>ATTGCAGATCCAATGGTAGAAGAGGCGGTTATTGTGCTGG<br>TTTGTTTAAGCAAACTTGTACCTGCTACTCCAGGTGA |
| 56. | Engineered persulcatusin with [R13S/R20T] | GGTTTTGGTTGTCCATTCAATCAAGGTGCTTGTCATAGTC<br>ATTGCAGATCCATTGGTACAAGAGGCGGTTATTGTGCTGG<br>TTTGTTTAAGCAAACTTGTACCTGCTACTCCAGGTGA |
| 57. | Engineered persulcatusin with [R13S/R21G] | GGTTTTGGTTGTCCATTCAATCAAGGTGCTTGTCATAGAC<br>ATTGCAGATCCATTGGTAGTGGAGGCGGTTATTGTGCTGG<br>TTTGTTTAAACAAACTTGTACCTGCTACTCCAGGTGA |
| 58. | Engineered persulcatusin with [R13S/R21S] | GGTTTTGGTTGTCCATTCAATCAAGGTGCTTGTCATAGTC<br>ATTGCAGATCCATTGGTAGAAGTGGCGGTTATTGTGCTGG<br>TTTGTTTAAGCAAACTTGTACCTGCTACTCCAGGTGA |
| 59. | Engineered persulcatusin with [R13S/A26D] | GGTTTTGGTTGTCCATTCAATCAAGGTGCTTGTCATAGTC<br>ATTGCAGATCCATTGGTAGAAGAGGCGGTTATTGTGATGG<br>TTTGTTTAAGCAAACTTGTACCTGCTACTCCAGGTGA |
| 60. | Engineered persulcatusin with [R13S/L28M] | GGTTTTGGTTGTCCATTCAATCAAGGTGCTTGTCATAGTC<br>ATTGCAGATCCATTGGTAGAAGAGGCGGTTATTGTGCTGG<br>TATGTTTAAGCAAACTTGTACCTGCTACTCCAGGTGA |

TABLE 1-continued

| SEQ ID NO: | Description | Amino Acid or Nucleic Acid Sequence |
|---|---|---|
| 61. | Engineered persulcatusin with [R16S/R20S] | GGTTTTGGTTGTCCATTCAATCAAGGAGCTTGTCATAGAC ATTGCAGCTCCATTGGTAGCAGAGGCGGATATTGTGCTGG TTTGTTTAAGCAAACTTGTACCTGCTACTCCAGGTGA |
| 62. | Engineered persulcatusin with [R16G/F29V] | GGTTTTGGTTGTCCATTCAATCAAGGTGCTTGTCATAGAC ATTGCGGATCCATTGGTAGAAGAGGCGGTTATTGTGCTGG TTTGGTTAAGCAAACTTGTACCTGCTACTCCAGGTGA |
| 63. | Engineered persulcatusin with [R20S/R21G] | GGTTTTGGTTGTCCATTCAATCAAGGTGCTTGTCATAGAC ATTGCAGATCCATTGGTAGTGGAAGCGGTTATTGTGCTGG TTTGTTTAAACAAACTTGTACCTGCTACTCCAGGTGA |
| 64. | Engineered persulcatusin with [F6L/N7D/H14Q] | GGTTTTGGCTGTCCACTCGATCAAGGTGCTTGTCATAGAC AATGCAGATCCATTGGTAGAAGAGGCGGTTATTGTGCTGG TTTGTTTAAGCAAACTTGTACCTGCTACTCCAGGTGA |
| 65. | Engineered persulcatusin with [F6L/G9D/H14Q] | GGTTTTGGTTGTCCACTCAATCAAGATGCTTGTCATAGAC AATGCAGATCCATTGGTAGAAGAGGCGGTTATTGTGCTGG TTTGTTTAAGCAAACTTGTACCTGCTACTCCAGGTGA |
| 66. | Engineered persulcatusin with [F6L/G9D/R20K] | GGTTTTGGTTGTCCACTCAATCAAGATGCTTGTCATAGAC ATTGCAGATCCATTGGTAAAAGAGGCGGTTATTGTGCTGG TTTGTTTAAGCAAACTTGTACCTGCTACTCCAGGTGA |
| 67. | Engineered persulcatusin with [F6V/R13S/A26D] | GGTTTTGGTTGTCCAGTCAATCAAGGTGCTTGTCATAGTC ATTGTAGATCCATTGGTAGAAGAGGCGGTTATTGTGATGG TTTGTTTAAGCAAACTTGTACCTGCTACTCCAGGTGA |
| 68. | Engineered persulcatusin with [N7D/H14F/R16S] | GGTTTTGGTTGTCCGTTCGATCAAGGTGCTTGTCATAGAT TTTGCAGTTCCATAGGTAGAAGAGGCGGTTATTGTGCTGG TTTGTTTAAGCAAACTTGTACCTGCTACTCCAGGTGA |
| 69. | Engineered persulcatusin with [G9D/I18F/F29L] | GGTTTTGGATGCCCATTCAATCAAGATGCTTGTCATAGGC ATTGCAGATCCTTTGGTAGAAGAGGCGGTTATTGTGCAGG TTTGCTTAAGCAAACTTGTACCTGCTACTCCAGGTGA |
| 70. | Engineered persulcatusin with [F6L/G9D/R13S/H14Q] | GGTTTTGGTTGTCCACTCAATCAAGATGCTTGTCATAGTC AATGCAGATCCATTGGTAGAAGAGGCGGTTATTGTGCTGG TTTGTTTAAGCAAACTTGTACCTGCTACTCCAGGTGA |
| 71. | Engineered persulcatusin with [F6S/R13S/I216K/I18V] | GGTTTTGGTTGTCCATCCAATCAAGGTGCTTGTCACAGTC ATTGCAAATCCGTTGGTAGAAGAGGCGGTTATTGTGCCGG TTTGTTTAAGCAAACTTGTACCTGCTACTCCAGGTGA |
| 72. | Pediocin PA-1 from [*Pediococcus acidilactici*] | AAGTACTACGGTAACGGTGTTACCTGTGGTAAACATTCTT GTTCTGTTGATTGGGGTAAAGCCACTACCTGCATTATTAA CAATGGTGCTATGGCTTGGGCTACTGGTGGTCATCAAGGT AATCATAAGTGTTGA |
| 73. | Engineered pediocin PA-1 with [K1A] | AYYGNGVTCGKHSCSVDWGKATTCIINNGAMAWATGGHQG NHKC |
| 74. | Engineered pediocin PA-1 with [K1T] | TYYGNGVTCGKHSCSVDWGKATTCIINNGAMAWATGGHQG NHKC |
| 75. | Engineered pediocin PA-1 with [S13A] | KYYGNGVTCGKHACSVDWGKATTCIINNGAMAWATGGHQG NHKC |
| 76. | Engineered pediocin PA-1 with [S15A] | KYYGNGVTCGKHSCAVDWGKATTCIINNGAMAWATGGHQG NHKC |
| 77. | Engineered pediocin PA-1 with [G19A] | KYYGNGVTCGKHSCSVDWAKATTCIINNGAMAWATGGHQG NHKC |
| 78. | Engineered pediocin PA-1 with [K20A] | KYYGNGVTCGKHSCSVDWGAATTCIINNGAMAWATGGHQG NHKC |
| 79. | Engineered pediocin PA-1 with [T22A] | KYYGNGVTCGKHSCSVDWGKAATCIINNGAMAWATGGHQG NHKC |
| 80. | Engineered pediocin PA-1 with [K1A/S13A] | AYYGNGVTCGKHACSVDWGKATTCIINNGAMAWATGGHQG NHKC |
| 81. | Engineered pediocin PA-1 with [K1A/S15A] | AYYGNGVTCGKHSCAVDWGKATTCIINNGAMAWATGGHQG NHKC |
| 82. | Engineered pediocin PA-1 with [K1A/G19A] | AYYGNGVTCGKHSCSVDWAKATTCIINNGAMAWATGGHQG NHKC |

TABLE 1-continued

| SEQ ID NO: | Description | Amino Acid or Nucleic Acid Sequence |
|---|---|---|
| 83. | Engineered pediocin PA-1 with [K1A/K20A] | AYYGNGVTCGKHSCSVDWGAATTCIINNGAMAWATGGHQGNHKC |
| 84. | Engineered pediocin PA-1 with [K1A/T22A] | AYYGNGVTCGKHSCSVDWGKAATCIINNGAMAWATGGHQGNHKC |
| 85. | Engineered pediocin PA-1 with [K1A/T22A/S13A] | AYYGNGVTCGKHACSVDWGKAATCIINNGAMAWATGGHQGNHKC |
| 86. | Engineered pediocin PA-1 with [K1A/T22A/S15A] | AYYGNGVTCGKHSCAVDWGKAATCIINNGAMAWATGGHQGNHKC |
| 87. | Engineered pediocin PA-1 with [K1A/T22A/G19A] | AYYGNGVTCGKHSCSVDWAKAATCIINNGAMAWATGGHQGNHKC |
| 88. | Engineered pediocin PA-1 with [K1A] | GCTTACTACGGTAACGGTGTTACCTGTGGTAAACATTCTTGTTCTGTTGATTGGGGTAAAGCCACTACCTGCATTATTAACAATGGTGCTATGGCTTGGGCTACTGGTGGTCATCAAGGTAATCATAAGTGTTGA |
| 89. | Engineered pediocin PA-1 with [K1T] | ACGTACTACGGTAACGGTGTTACCTGTGGTAAACATTCTTGTTCTGTTGATTGGGGTAAAGCCACTACCTGCATTATTAACAATGGTGCTATGGCTTGGGCTACTGGTGGTCATCAAGGTAATCATAAGTGTTGA |
| 90. | Engineered pediocin PA-1 with [S13A] | AAGTACTACGGTAACGGTGTTACCTGTGGTAAACATGCTTGTTCTGTTGATTGGGGTAAAGCCACTACCTGCATTATTAACAATGGTGCTATGGCTTGGGCTACTGGTGGTCATCAAGGTAATCATAAGTGTTGA |
| 91. | Engineered pediocin PA-1 with [S15A] | AAGTACTACGGTAACGGTGTTACCTGTGGTAAACATTCTTGTGCTGTTGATTGGGGTAAAGCCACTACCTGCATTATTAACAATGGTGCTATGGCTTGGGCTACTGGTGGTCATCAAGGTAATCATAAGTGTTGA |
| 92. | Engineered pediocin PA-1 with [G19A] | AAGTACTACGGTAACGGTGTTACCTGTGGTAAACATTCTTGTTCTGTTGATTGGGCTAAAGCCACTACCTGCATTATTAACAATGGTGCTATGGCTTGGGCTACTGGTGGTCATCAAGGTAATCATAAGTGTTGA |
| 93. | Engineered pediocin PA-1 with [K20A] | AAGTACTACGGTAACGGTGTTACCTGTGGTAAACATTCTTGTTCTGTTGATTGGGGTGCTGCCACTACCTGCATTATTAACAATGGTGCTATGGCTTGGGCTACTGGTGGTCATCAAGGTAATCATAAGTGTTGA |
| 94. | Engineered pediocin PA-1 with [T22A] | AAGTACTACGGTAACGGTGTTACCTGTGGTAAACATTCTTGTTCTGTTGATTGGGGTAAAGCCGCTACCTGCATTATTAACAATGGTGCTATGGCTTGGGCTACTGGTGGTCATCAAGGTAATCATAAGTGTTGA |
| 95. | Engineered pediocin PA-1 with [K1A/S13A] | GCTTACTACGGTAACGGTGTTACCTGTGGTAAACATGCTTGTTCTGTTGATTGGGGTAAAGCCACTACCTGCATTATTAACAATGGTGCTATGGCTTGGGCTACTGGTGGTCATCAAGGTAATCATAAGTGTTGA |
| 96. | Engineered pediocin PA-1 with [K1A/S15A] | GCTTACTACGGTAACGGTGTTACCTGTGGTAAACATTCTTGTGCTGTTGATTGGGGTAAAGCCACTACCTGCATTATTAACAATGGTGCTATGGCTTGGGCTACTGGTGGTCATCAAGGTAATCATAAGTGTTGA |
| 97. | Engineered pediocin PA-1 with [K1A/G19A] | GCTTACTACGGTAACGGTGTTACCTGTGGTAAACATTCTTGTTCTGTTGATTGGGCTAAAGCCACTACCTGCATTATTAACAATGGTGCTATGGCTTGGGCTACTGGTGGTCATCAAGGTAATCATAAGTGTTGA |
| 98. | Engineered pediocin PA-1 with [K1A/K20A] | GCTTACTACGGTAACGGTGTTACCTGTGGTAAACATTCTTGTTCTGTTGATTGGGGTGCTGCCACTACCTGCATTATTAACAATGGTGCTATGGCTTGGGCTACTGGTGGTCATCAAGGTAATCATAAGTGTTGA |
| 99. | Engineered pediocin PA-1 with [K1A/T22A] | GCTTACTACGGTAACGGTGTTACCTGTGGTAAACATTCTTGTTCTGTTGATTGGGGTAAAGCCGCTACCTGCATTATTAACAATGGTGCTATGGCTTGGGCTACTGGTGGTCATCAAGGTAATCATAAGTGTTGA |

TABLE 1-continued

| SEQ ID NO: | Description | Amino Acid or Nucleic Acid Sequence |
|---|---|---|
| 100. | Engineered pediocin PA-1 with [K1A/T22A/S13A] | GCTTACTACGGTAACGGTGTTACCTGTGGTAAACATGCTT GTTCTGTTGATTGGGGTAAAGCCGCTACCTGCATTATTAA CAATGGTGCTATGGCTTGGGCTACTGGTGGTCATCAAGGT AATCATAAGTGTTGA |
| 101. | Engineered pediocin PA-1 with [K1A/T22A/S15A] | GCTTACTACGGTAACGGTGTTACCTGTGGTAAACATTCTT GTGCTGTTGATTGGGGTAAAGCCGCTACCTGCATTATTAA CAATGGTGCTATGGCTTGGGCTACTGGTGGTCATCAAGGT AATCATAAGTGTTGA |
| 102. | Engineered pediocin PA-1 with [K1A/T22A/G19A] | GCTTACTACGGTAACGGTGTTACCTGTGGTAAACATTCTT GTTCTGTTGATTGGGCTAAAGCCGCTACCTGCATTATTAA CAATGGTGCTATGGCTTGGGCTACTGGTGGTCATCAAGGT AATCATAAGTGTTGA |

It is understood that modifications which do not substantially affect the activity of the various embodiments of this invention are also provided within the definition of the invention provided herein. Accordingly, the following examples are intended to illustrate but not limit the present invention.

EXAMPLE I

Plasmid Construction

The pHVXKD3 plasmid (Dahabieh et al., J. Enol. Vitic. 60:537-541 (2009)) was modified to create pHVXU-mRUBY by inserting the URA3 coding region between PGK1p and PGK1t and replacing the kan$^r$ between AgTEFp and AgTEFt with "MFα1-J23119-mRUBY" (FIG. 1). pHVXU-mRUBY2 was created by replacing MFα1 in pHVXU-mRUBY with a fusion secretion signal consisting of Ost1 and MFα1 secretion signals (Fitzgerald et al., Microb. Cell Fact., 13:125 (2014); and Barrero et al., Microb. Cell Fact., 17:161 (2018)). The DNA sequence for wild-type persulcatusin (SEQ ID NO: 37) was synthesized and cloned into pHVXU-mRUBY to create pHVXU-IP by replacing "J23119-mRUBY" between MFα1 and AgTEFt with persulcatusin. The DNA sequence for wild-type pediocin PA-1 (SEQ ID NO: 72) was similarly used to create pHVXU-pedA.

EXAMPLE II

Alanine Scanning of Persulcatusin

Alanine scanning was performed with persulcatusin to gain insight into each amino acid residue of persulcatusin. The mutated persulcatusin sequences were synthesized by performing PCR to extend overlapping primers that contained the desired mutations. This was cloned into the linearized vector obtained by using PCR to amplify pHVXU-mRUBY using primers complementary to the MFα1 and AgTEFt regions followed by DpnI digestion and gel purification. The resulting plasmids were sequenced and transformed into S. cerevisiae BY4742, which was tested for activity using the soft-agar overlay assay with L. fermentum NCCB 46038.

For the soft-agar overlay assay, engineered yeast were spotted onto agar plates and grown at 30° C. The agar plates for growing yeast contained either YPD (10 g/L yeast extract, 20 g/L peptone and 20 g/L dextrose) or YNBD minus uracil (1.7 g/L yeast nitrogen base without amino acids and ammonium sulfate, 20 g/L dextrose, 1.92 g/L yeast synthetic drop-out medium supplement without uracil). Lactic acid bacteria (LAB) were grown in MRS media at 37° C. Molten MRS with 0.7% agar was cooled to 50° C. before inoculating to 1% v/v with the LAB culture. The soft-agar overlay was gently poured over the yeast colonies grown 1-3 days on the agar plates and incubated at 30° C. Growth inhibition of the LAB around the yeast secreting the peptides was observed if the peptide being secreted was effective against the specific LAB being tested. Bigger growth inhibition zones indicated higher antibacterial activity of the peptide secreted by the yeast.

Figure 2:
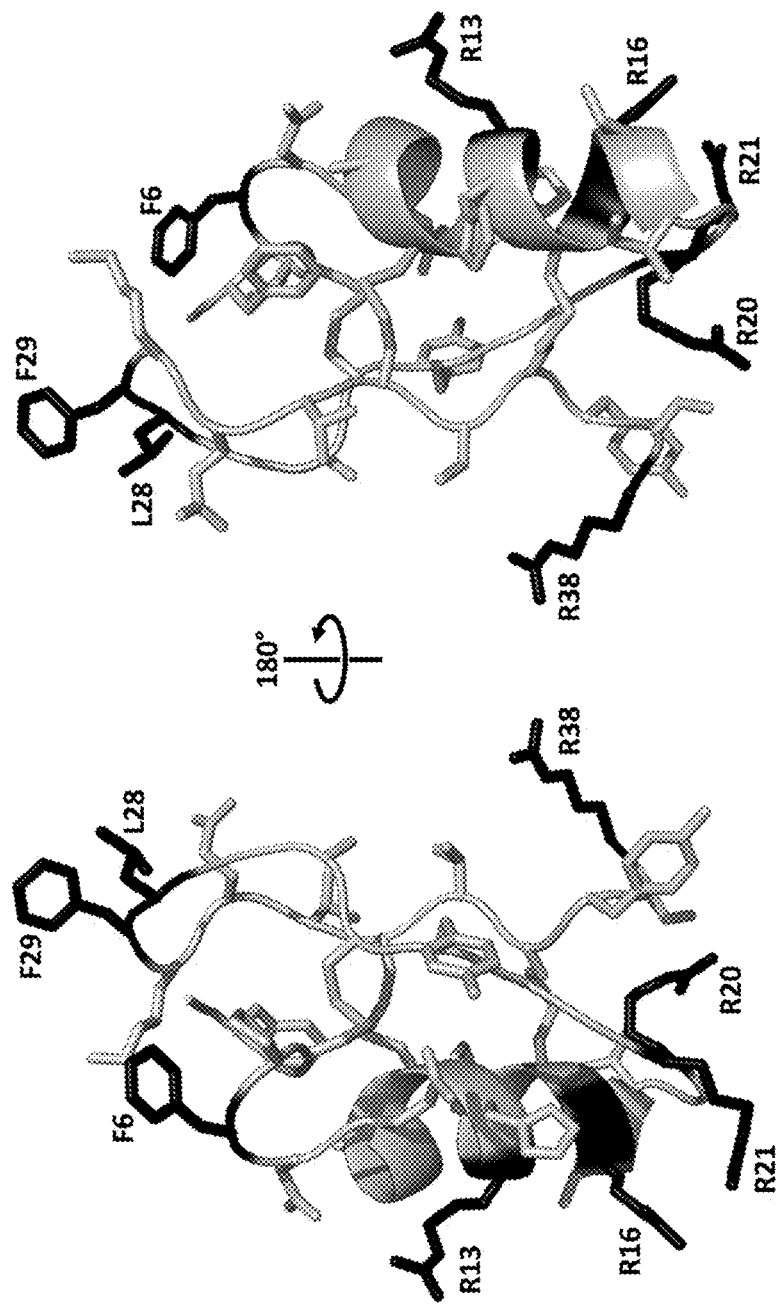
FIG. 2 shows a homology model of persulcatusin. Homology models of persulcatusin were created using SWISS-MODEL (Waterhouse et al., SWISS-MODEL: Homology modelling of protein structures and complexes. Nucleic Acids Res. (2018), doi:10.1093/nar/gky427; and Guex et al., Electrophoresis (2009), doi:10.1002/elps.200900140). The model shown was created using BmKDfsin3 (PDB ID:5XA6), which has 76% sequence identity with persulcatusin, as a template. Three disulfide bonds were predicted in the structure between C4 and C25, C11 and C33, and C15 and C35. The residues where alanine substitutions increased activity are labelled and colored black. In addition to the alpha-helix shown above, an anti-parallel beta-sheet is observed between approximately G23-A26 and T32-C35 in models using other templates. This figure was prepared with PyMOL (pymol.org).

The alanine scanning experiment on persulcatusin indicated that alanine substitutions at F6, R13, R16, R20, R21, L28, F29, and R38 resulted in higher antibacterial activity (Table 2). Based on a structural homology model of persulcatusin, these positions are localized at more than one area of the peptide (FIG. 2). Alanine substitutions at 22 of the positions resulted in decreased activity, which indicates that function is easily perturbed by mutations. As so many of these substitutions resulted in decreased activity, additional analysis as described in Example III was conducted to provide a clearer indication of which residues are particularly necessary for function.

TABLE 2

Antibacterial activity change with alanine scanning for persulcatusin

| Mutation | Change in activity |
|---|---|
| G1A | − |
| F2A | − |
| G3A | = |
| C4A | − |
| P5A | = |
| F6A | + |
| N7A | − |
| Q8A | − |
| G9A | = |
| A10 | N/A |
| C11A | − |
| H12A | − |
| R13A | + |
| H14A | − |
| C15A | − |
| R16A | + |
| S17A | − |
| I18A | = |
| G19A | = |

TABLE 2-continued

Antibacterial activity change with alanine scanning for persulcatusin

| Mutation | Change in activity |
|---|---|
| R20A | + |
| R21A | + |
| G22A | − |
| G23A | − |
| Y24A | − |
| C25A | − |
| A26 | N/A |
| G27A | − |
| L28A | + |
| F29A | + |
| K30A | − |
| Q31A | − |
| T32A | − |
| C33A | − |
| T34A | − |
| C35A | − |
| Y36A | − |
| S37A | = |
| R38A | + |

(−) Decrease in activity, (=) no change in activity, (+) increase in activity, and (N/A) not applicable relative to wild-type as determined by soft-agar overlay assay against *Lactobacillus fermentum* NCCB 46038.

EXAMPLE III

Random Mutagenesis of Persulcatusin

Random mutagenesis was performed using error-prone PCR to amplify and mutate persulcatusin from pHVXU-IP with 50 bp primers flanking persulcatusin and complementary to regions in MFα1 and AgTEFt (Viña-Gonzalez et al., J. Vis. Exp. e53761 (2016)). The template pHVXU-IP was digested by DpnI and the insert containing mutated persulcatusin was gel purified. The linearized vector was obtained by cutting pHVXU-mRUBY in the mRUBY sequence with NdeI or by using PCR to amplify pHVXU-mRUBY using primers complementary to the MFα1 and AgTEFt regions followed by DpnI digestion and gel purification.

The mutated persulcatusin insert and linearized vector was transformed into *Saccharomyces cerevisiae* BY4742 using the LiAc/SS carrier DNA/PEG method (Gietz et al., Nat. Protoc. 2:38-41 (2007)). The transformants were plated onto YNBD minus uracil agar plates and grown for 3-5 days at 30° C. Yeast colonies that grew were expected to contain the plasmid created by in vivo homologous recombination between the insert containing the mutated persulcatusin and the vector containing the URA3 selection marker. These plates were used with a soft-agar overlay of *L. fermentum* NCCB 46038 as described in Example II. Colonies that had large inhibition zones were picked and retested with the soft-agar overlay assay.

Colony PCR was performed with the colonies of interest to amplify the persulcatusin insert using 50 bp flanking primers. The PCR fragment was sequenced to determine the beneficial mutations.

The PCR fragments containing mutated persulcatusin from multiple colonies were pooled and used as a DNA template for a second round of random mutagenesis. This insert was transformed with linearized pHVXU-mRUBY or pHVXU-mRUBY2 into *S. cerevisiae* BY4742. The process of determining beneficial mutations was repeated similarly to the first round of mutagenesis.

Using the above approach, several persulcatusin mutants were identified that had increased antibacterial activity against *L. fermentum* NCCB 46038. Such persulcatusin mutants are shown in Table 3. Many of these mutations occurred at the same positions that where identified by the alanine substitutions described in Example II as also increasing activity, which indicates that different amino acid substitutions at the same positions can be beneficial.

TABLE 3

Persulcatusin mutants showing increased antibacterial activity

| Clone Name | Mutation(s) | Increase in Activity |
|---|---|---|
| S7-140-2 | R13S | + |
| S7-140-8 | R21G | + |
| S7-140-9 | A26D | + |
| S-176-2-1 | F6V/R13S | ++ |
| S7-140-18 | N7D/R16S | + |
| S7-140-42 | N7D/F29L | ++ |
| S7-192-7 | G9D/H14Q | ++ |
| S7-144-4 | G9D/R20S | ++ |
| S7-144-59 | R13S/R16K | + |
| S7-140-1 | R13S/I18N | + |
| S7-140-34 | R13S/R20T | ++ |
| S7-140-10 | R13S/R21G | + |
| S7-176-3-1 | R13S/R21S | ++ |
| S7-144-75 | R13S/A26D | ++ |
| S7-144-43 | R13S/L28M | + |
| S7-144-11 | R16S/R20S | ++ |
| S7-140-7 | R16G/F29V | + |
| S7-140-3 | R20S/R21G | + |
| S7-192-22 | F6L/N7D/H14Q | ++ |
| S7-192-26 | F6L/G9D/H14Q | +++ |
| S7-176-5-1 | F6L/G9D/R20K | ++ |
| S7-176-4-1 | F6V/R13S/A26D | ++ |
| S7-192-4 | N7D/H14F/R16S | ++ |
| S7-156-22 | G9D/R13S/I18F/F29L | + |
| S7-192-1 | F6L/G9D/R13S/H14Q | ++++ |
| S7-156-36 | F6S/R13S/R16K/I18V | ++ |

Increase in activity observed by increase of growth inhibition zones in soft-agar overlay assays.

EXAMPLE IV

Yeast Strain Construction and Ethanol Production

Figure 3:
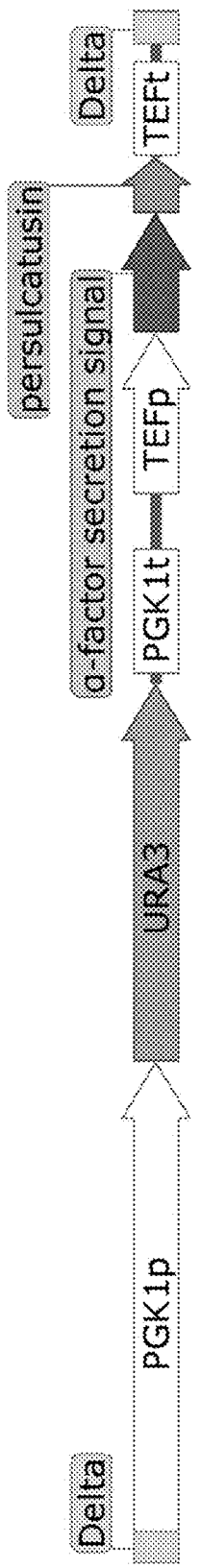
FIG. 3 shows an exemplary gene cassette for expression of engineered persulcatusin. A gene cassette was created for expressing engineered persulcatusin having alterations F6L, G9D, R13S and H14Q by PCR amplification of the cassette from pHVXU-IPm4 using primers that contained flanking regions homologous to chromosomal delta sites.

The wine strain, *S. cerevisiae* Enoferm M2, was used as a model yeast in mock fermentation experiments. The plasmid pHVXU-IPm4, which expresses an engineered persulcatusin having alterations F6L, G9D, R13 S and H14Q, was transformed into M2 MATa/α ura3Δ/ura3Δ using the LiAc/SS carrier DNA/PEG method to create the strain, M2-pIPm4. The transformants were screened for antibacterial activity using the soft-agar overlay assay as described in Example II. The strain M2-cIPm4, M2 MA Talα ura3Δ/ura3Δ which expresses an engineered persulcatusin having alterations F6L, G9D, R13S and H14Q from chromosomally integrated cassettes, was created by transforming with a DNA expression cassette targeting delta integration sites (FIG. 3). The cassette was created by PCR amplification from pHVXU-IPm4 using primers with flanking delta site sequences, DpnI digestion, and gel purification. The transformants were screened for antibacterial activity using the soft-agar overlay assay. Presence of the pHVXU-IPm4 inadvertently transformed into the yeast was not detected by colony PCR. The best strain, M2-cIPm4, was used for mock fermentation experiments.

Small-scale mock ethanol fermentations were carried out in 2 mL microcentrifuge tubes with a venting hole in the cap made with a 30 gauge needle. Starter cultures of yeast were grown in YPD at 30° C. with agitation. Starter cultures of *L.* fermentum CCUG 72619 were grown in MRS at 37° C. without agitation. Yeast and *L. fermentum* CCUG 72619 were resuspended in fermentation media (filter sterilized corn mash, 1.2 g/L ammonium sulfate) and used to inoculate fermentation media with final volumes of 1 mL. The yeast starting $OD_{600}=1$ and the bacterial contamination level was varied. Control fermentations contained 2 mg/L virginiamycin. The fermentations were incubated at 30° C. without agitation for 72 hours and then analyzed by HPLC.

Figure 4B:
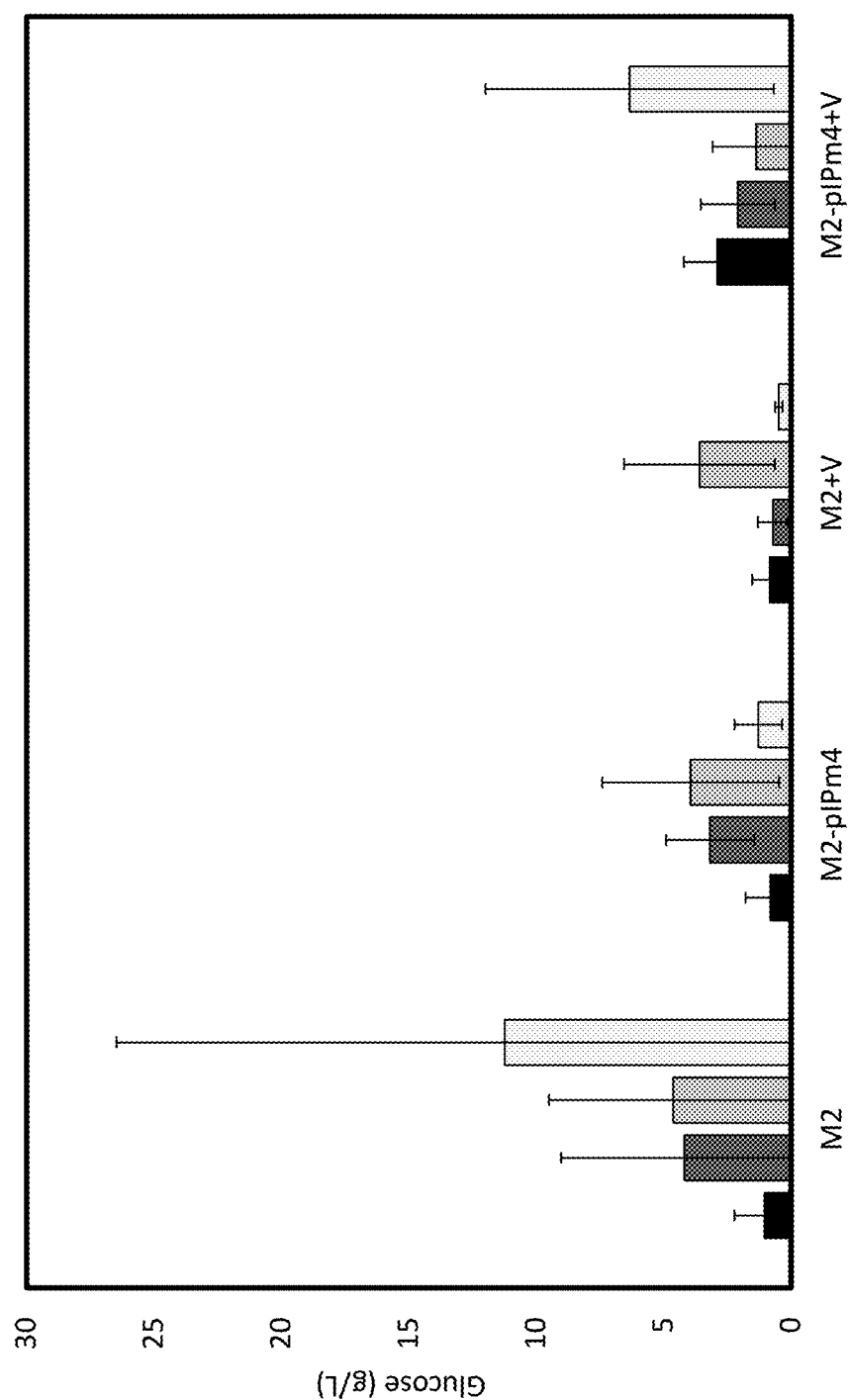
Figure 4C:
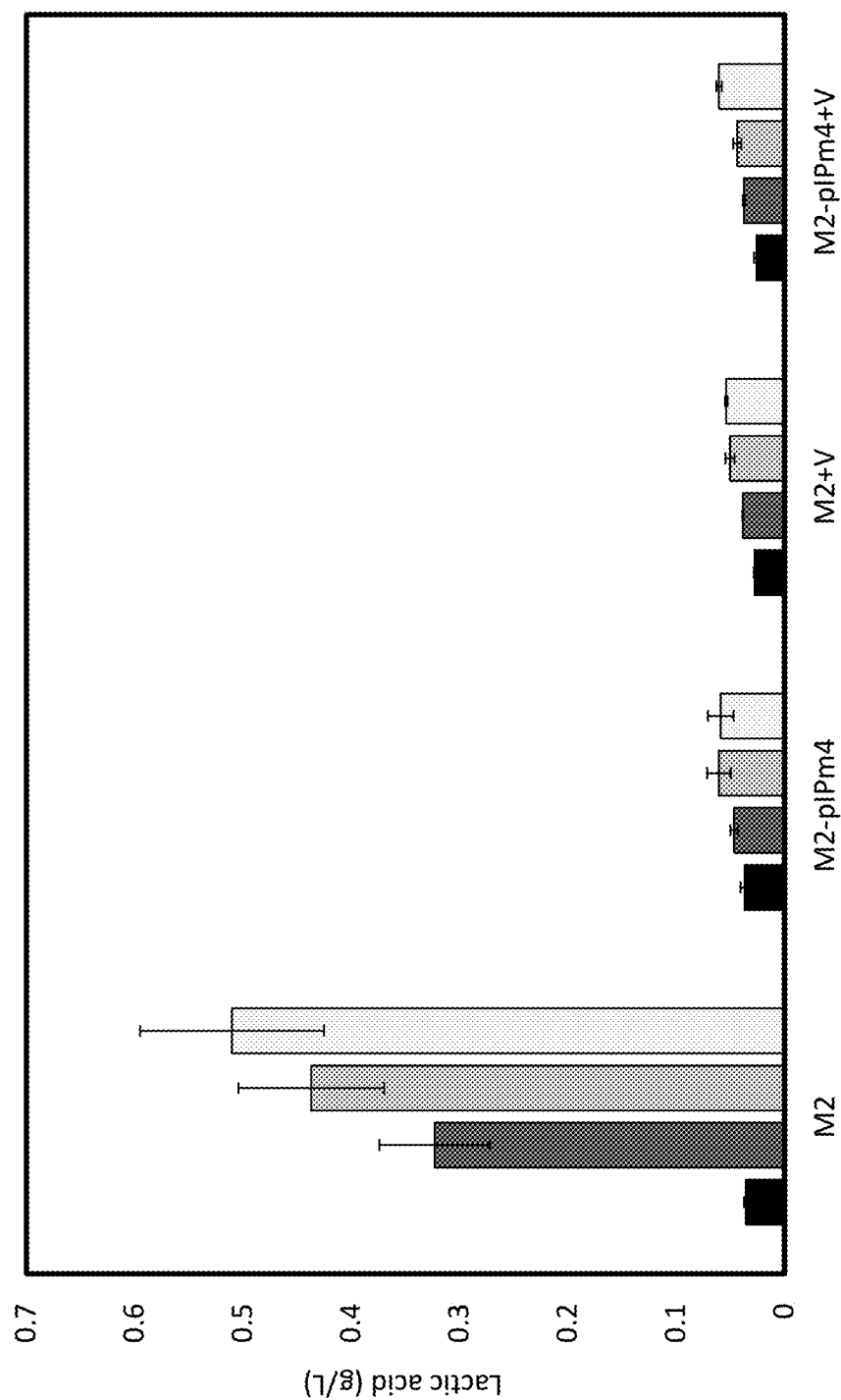
Figure 4E:
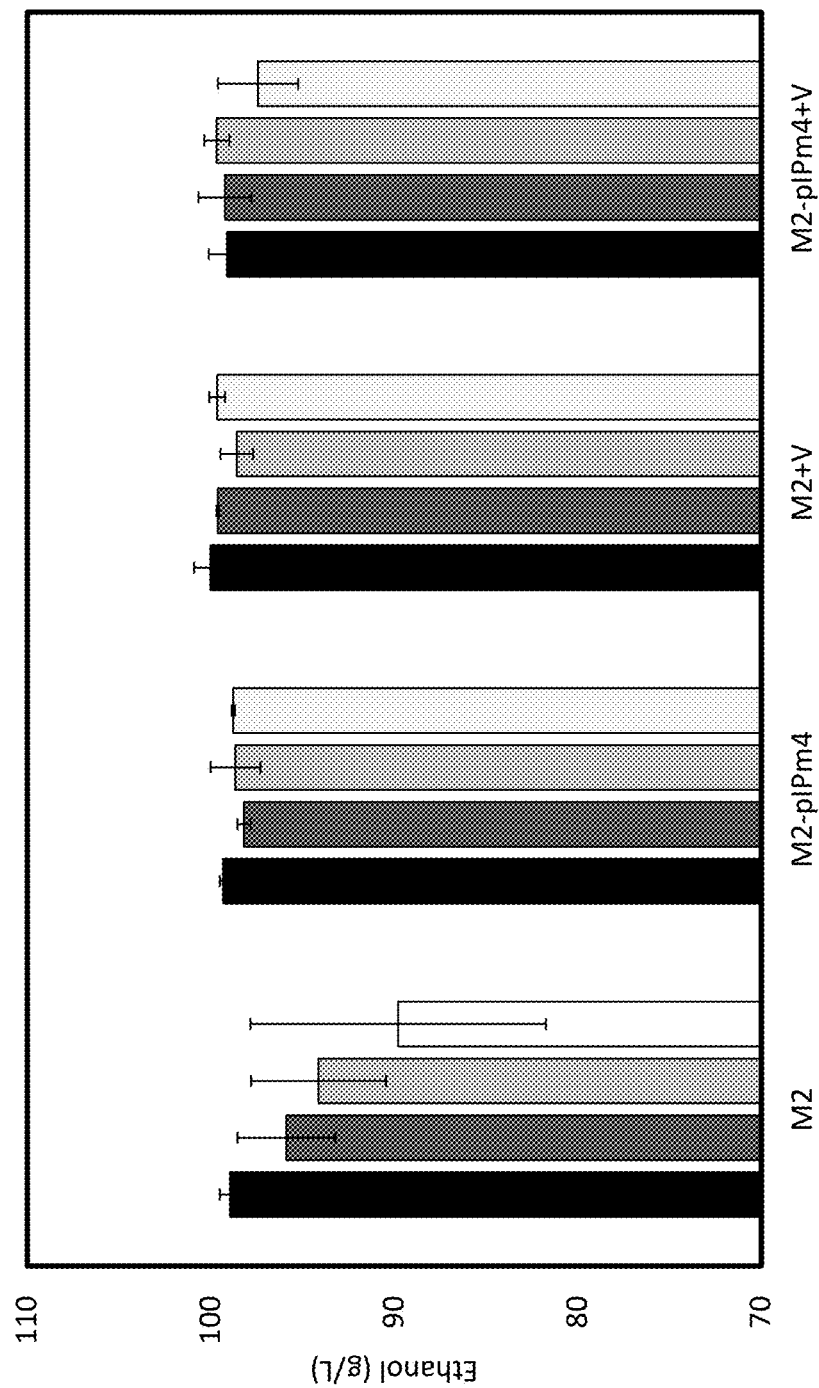
FIGS. 4E-4H show the same exemplary results of FIGS. 4A-4D, respectively, except with corrections for calibration errors.
Figure 4F:
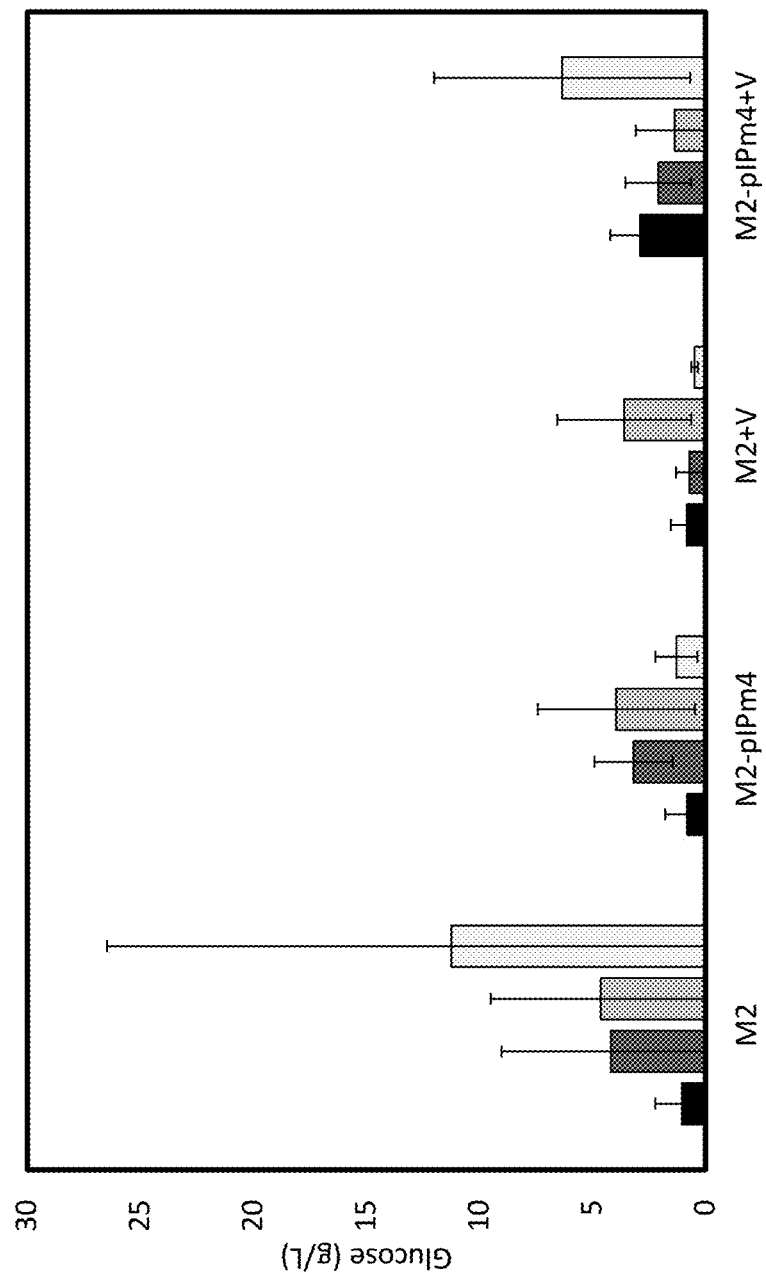
Figure 4G:
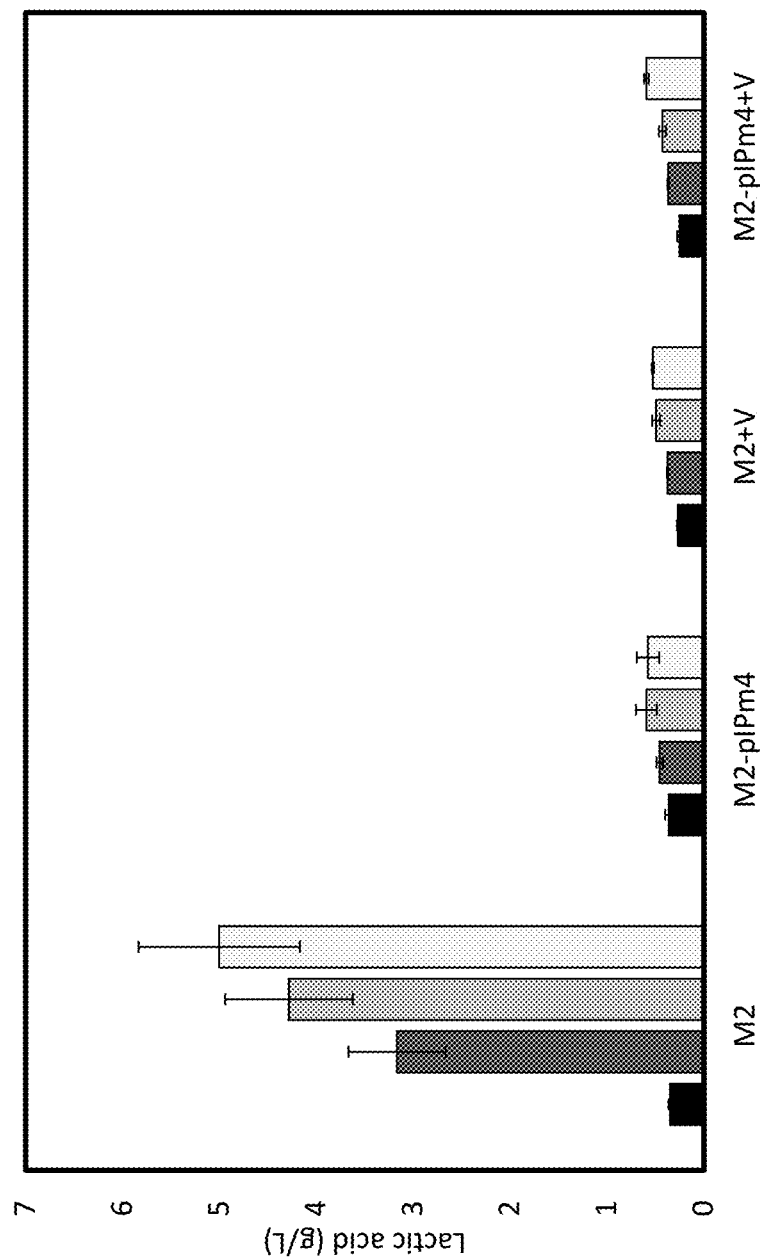
Figure 4H:
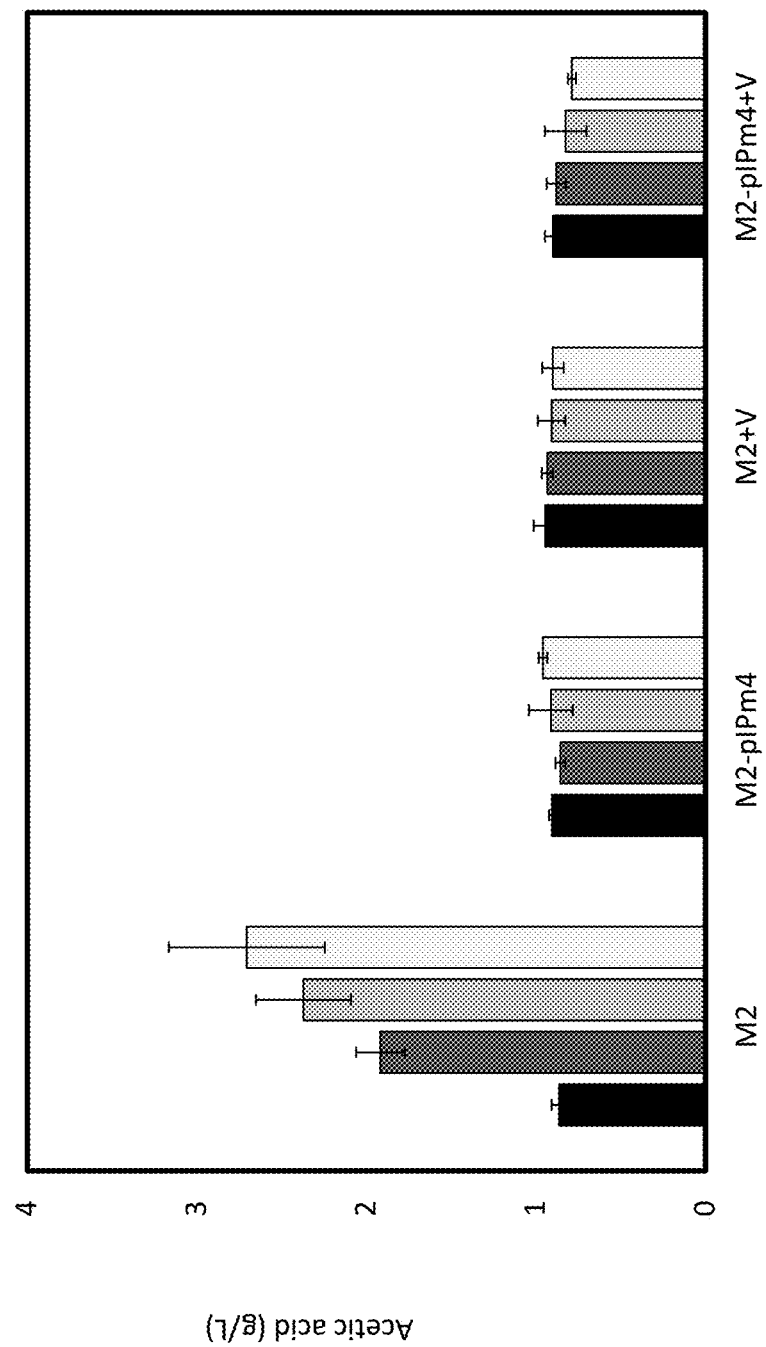
Figure 5A:
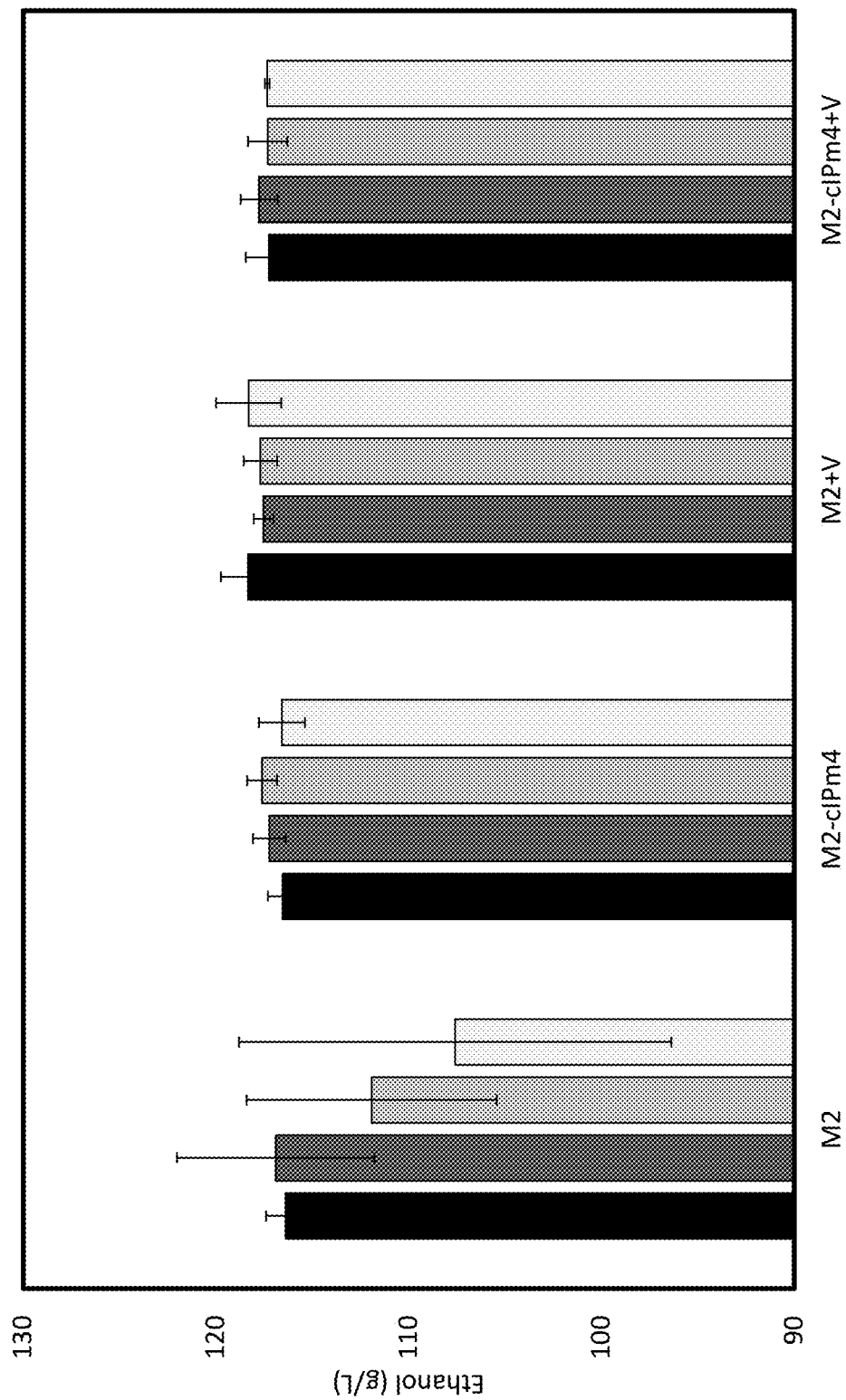
FIGS. 5A-5D show exemplary results for fermentations with M2 wild-type and M2-cIPm4 expressing engineered persulcatusin having alterations F6L, G9D, R13S and H14Q from chromosomally integrated cassettes with varying levels of *L. fermentum* contamination. Filtered corn mash supplemented with 1.2 g/L ammonium sulfate was inoculated with M2 and M2-cIPm4 to an $OD_{600}$=1. M2 and M2-cIPm4 were not supplemented with virginiamycin and M2+V and M2-cIPm4+V were supplemented with 2 mg/L virginiamycin. Fermentations were not contaminated (black bars) or artificially contaminated with *L. fermentum* to $OD_{600}$ levels of 0.05 (dark grey bars), 0.1 (light grey bars), or 0.15 (white bars). After 72 hours, levels of ethanol (FIG. 5A), glucose (FIG. 5B), lactic acid (FIG. 5C), and acetic acid (FIG. 5D) were determined by HPLC. Fermentations were performed in triplicate and the error bars represent standard deviation.
Figure 5B:
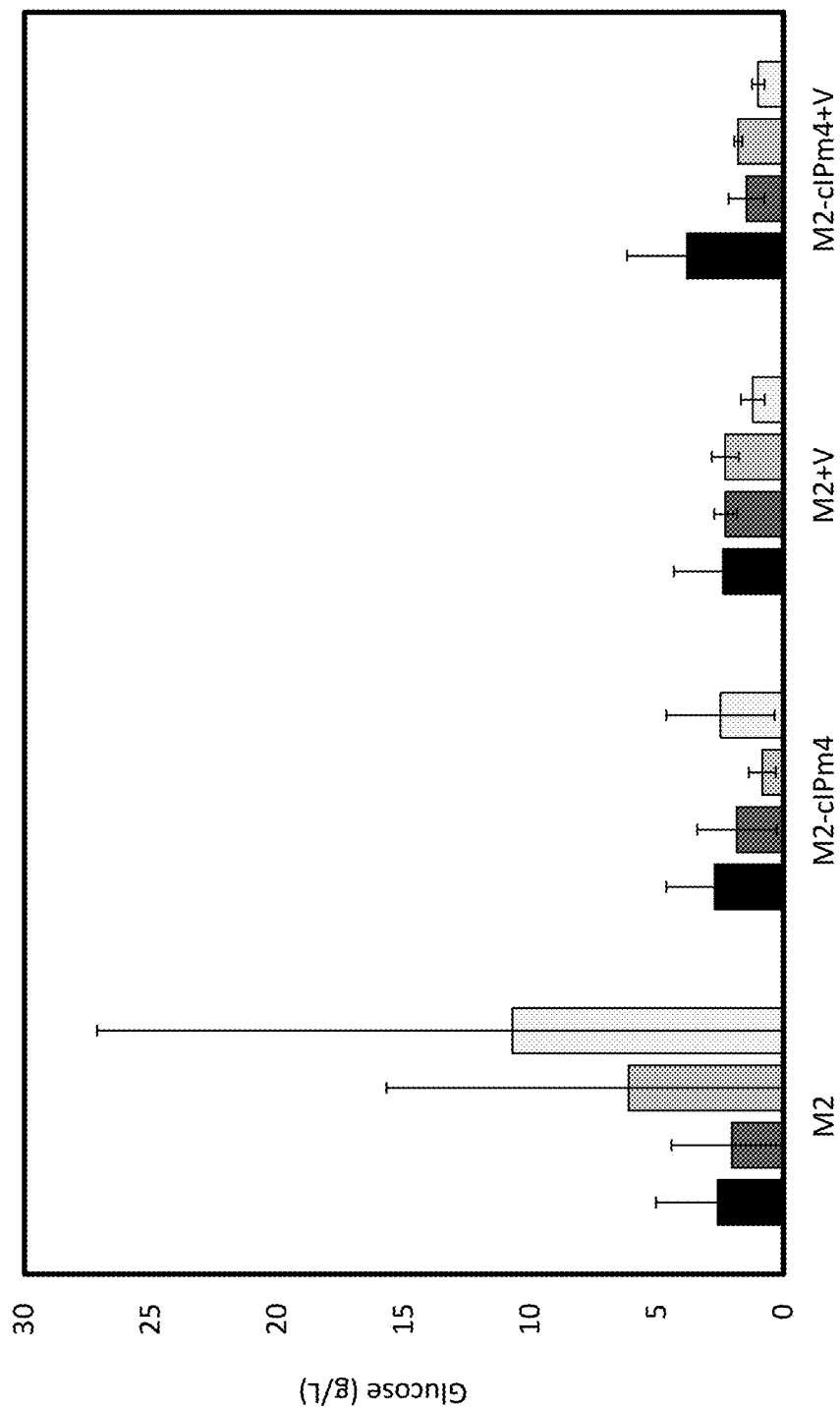
Figure 5C:
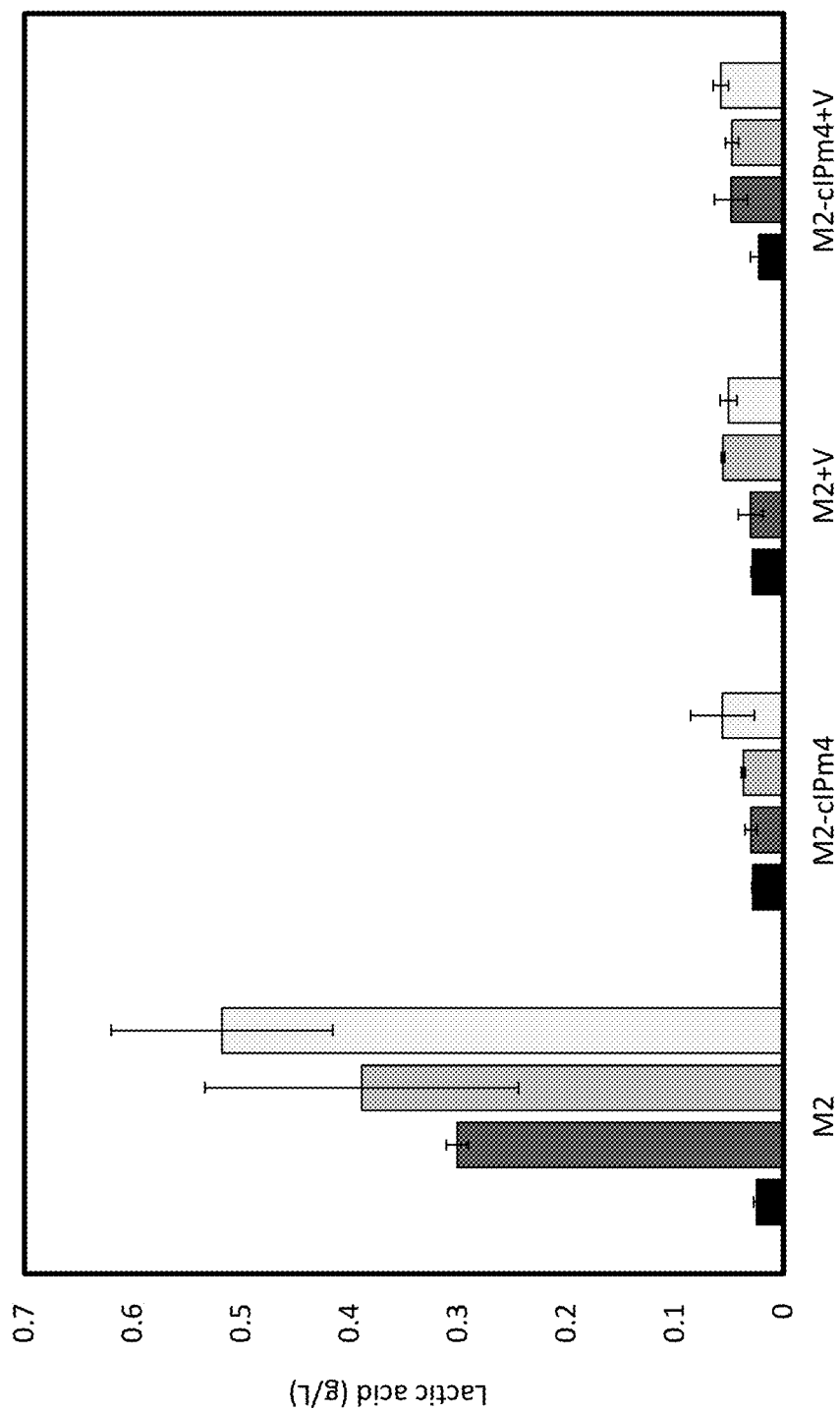
Figure 5D:
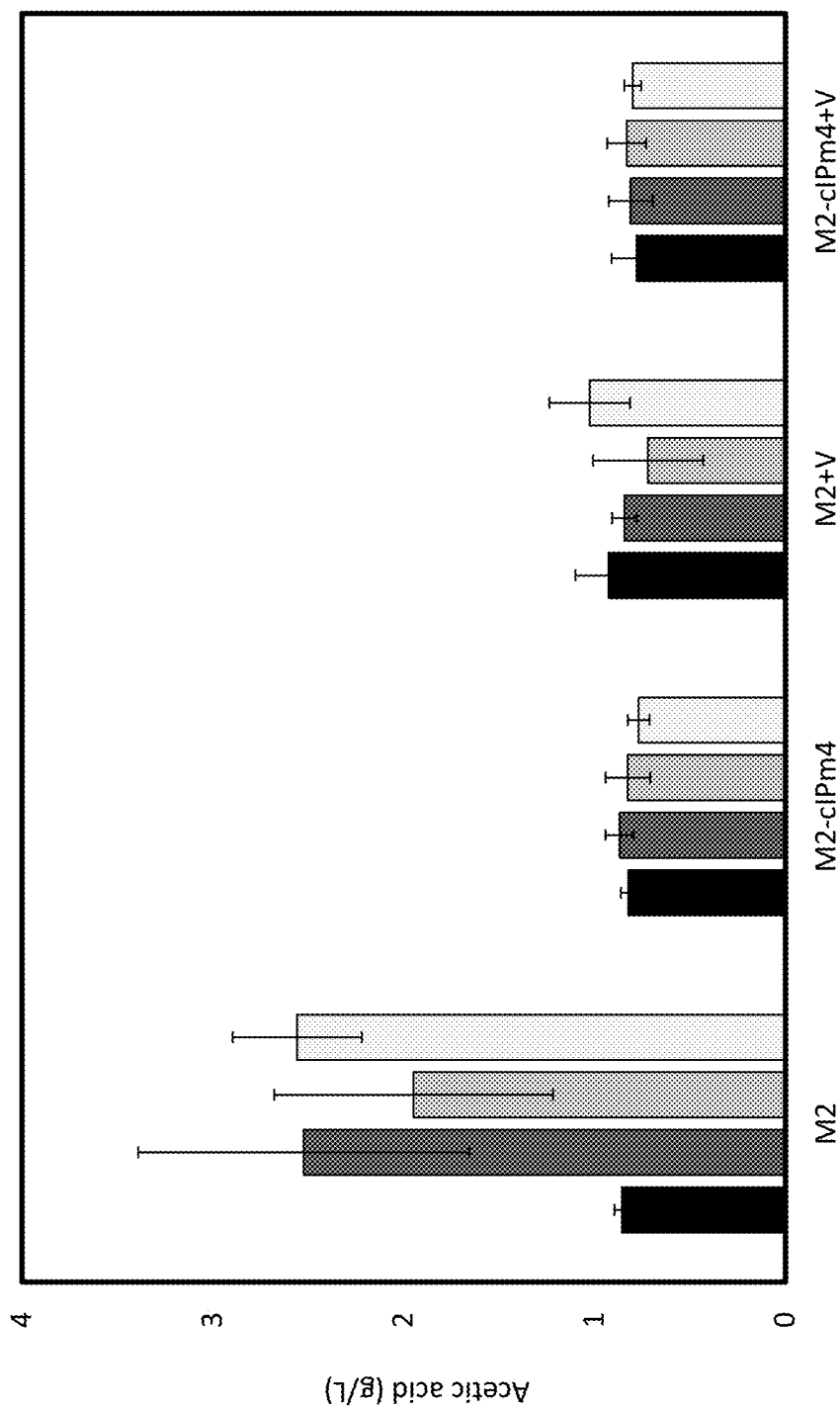
Figure 5E:
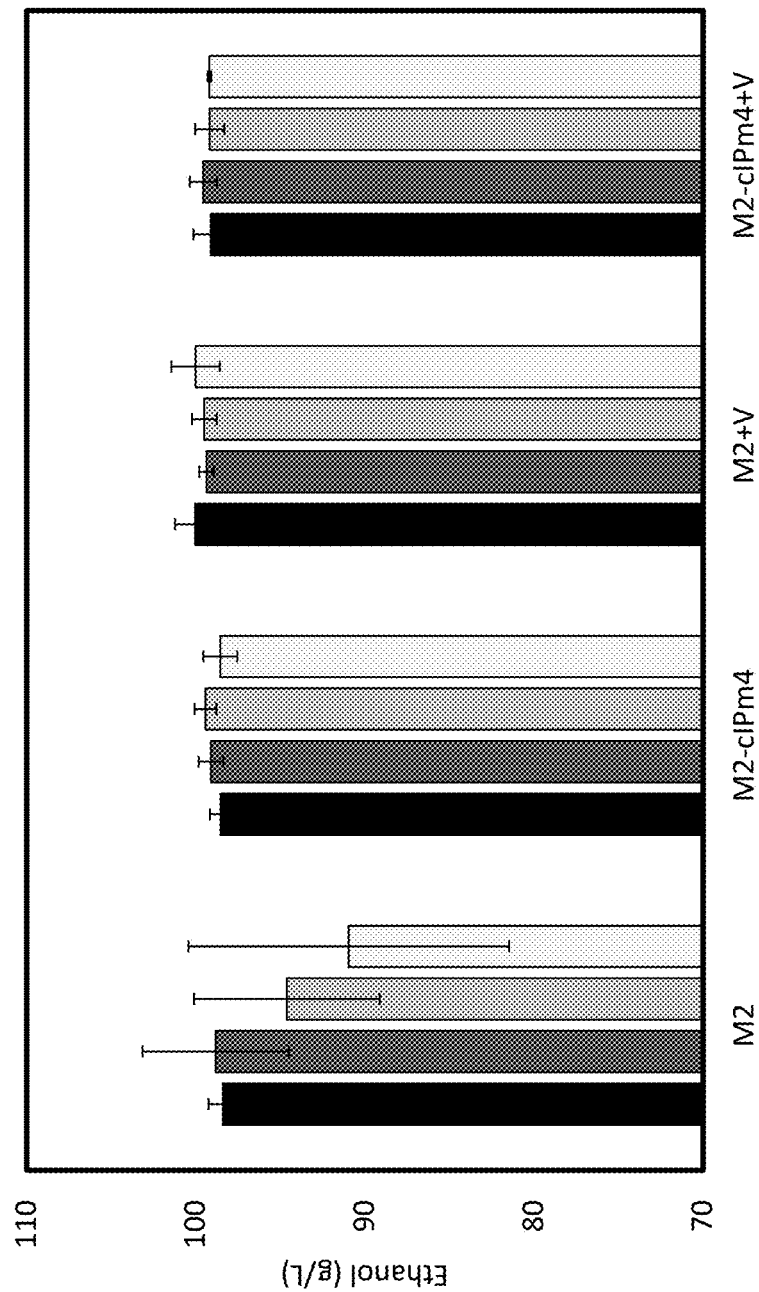
FIGS. 5E-5H show the same exemplary results of FIGS. 5A-5D, respectively, except with corrections for calibration errors.
Figure 5F:
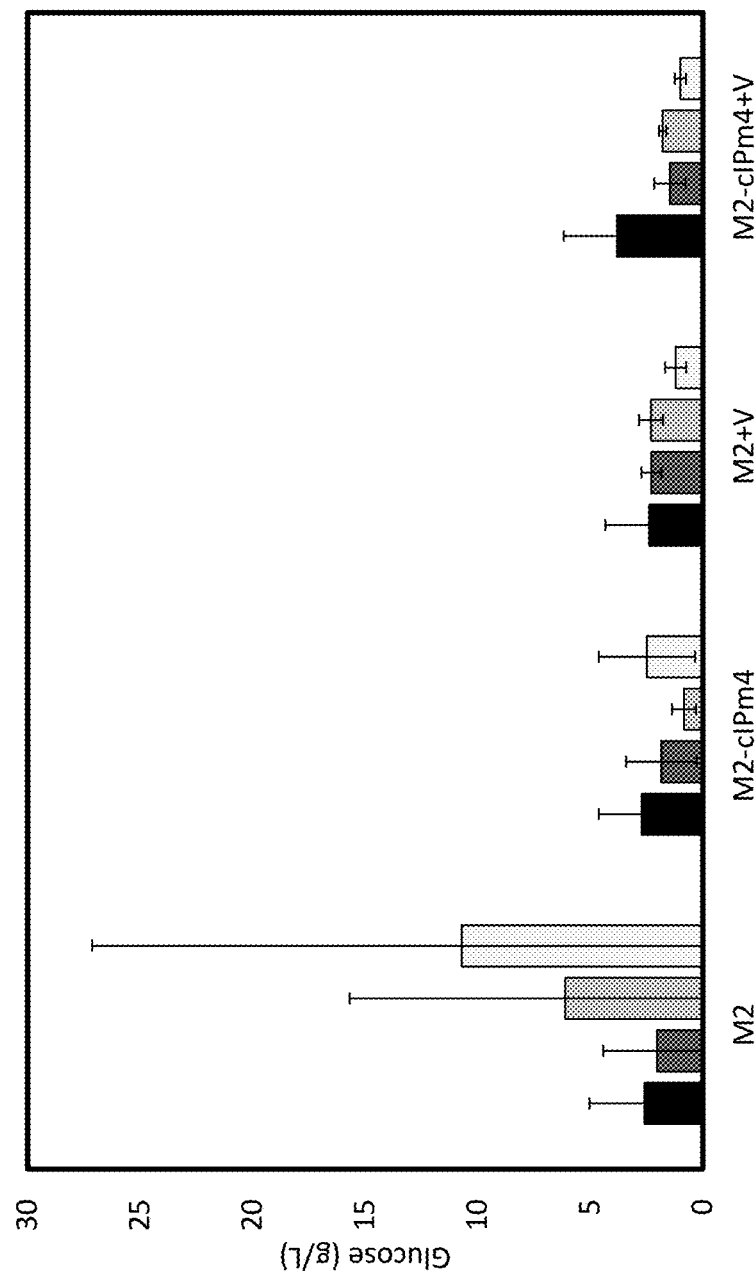
Figure 5G:
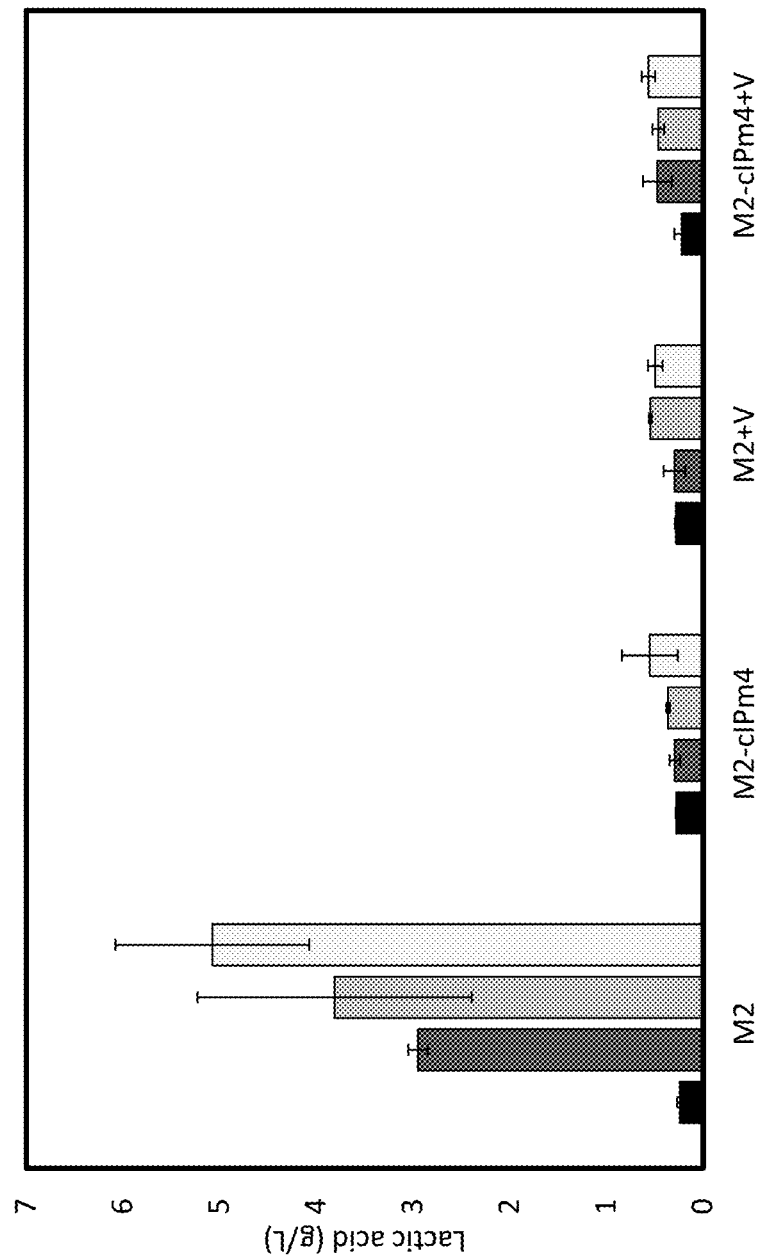
Figure 5H:
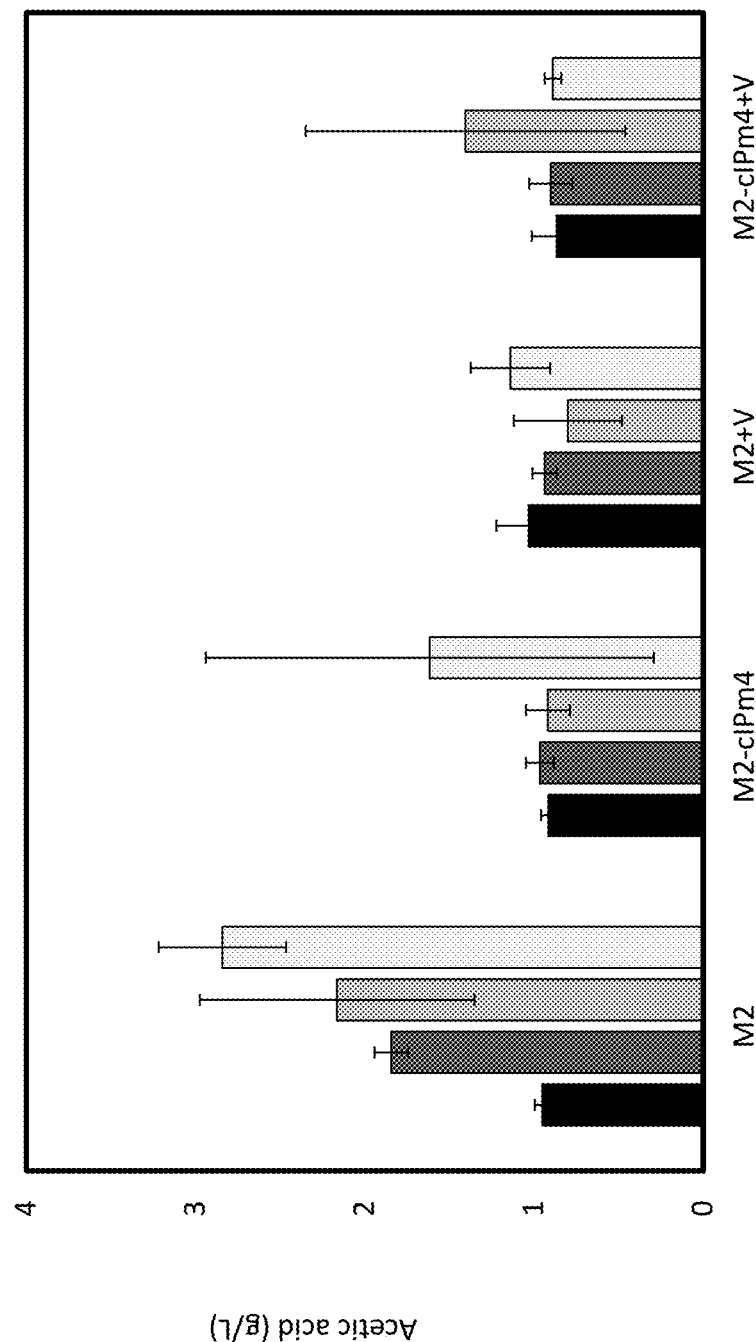

M2-pIPm4 and M2-cIPm4, which expresses an engineered persulcatusin having alterations F6L, G9D, R13S and H14Q from plasmids or from chromosomally integrated cassettes, respectively, were compared to M2 wild-type with varying levels of *L. fermentum* CCUG 72619 contamination. *L. fermentum* contamination resulted in reduced ethanol yields and increased variability in its production (FIGS. 4A-4H and FIGS. 5A-5H). For example, lactic and acetic acid levels were significantly increased in the contaminated fermentations compared to the non-contaminated fermentations (FIG. 4C/4G, FIG. 4D/4F, FIG. 5C/5G and FIG. 5D/5F), which is consistent with the expectation that these acids are produced by *L. fermentum*. M2-pIPm4, M2-cIPm4, and fermentations with virginiamycin did not appear to suffer from reduced ethanol yields due to bacterial contamination (FIG. 4A/4E and FIG. 5A/5E). The fermentations of M2 with the highest levels of *L. fermentum* contamination appeared to have considerable variability in residual glucose, which tended to be reduced when using M2-pIPm4, M2-cIPm4, or virginiamycin (FIGS. 4B/4F and FIGS. 4C/4G). The lactic and acetic acid levels were significantly lower in these fermentations than the contaminated fermentations with M2 wild-type (FIGS. 4C/4G, FIGS. 4D/4H, FIGS. 5C/5G and FIGS. 5D/5G). The fermentations with M2 wild-type supplemented with virginiamycin and engineered strains expressing an engineered persulcatusin, both from plasmid and chromosomally, did not appear to suffer from the negative effects of *L. fermentum* contamination as observed in M2 wild-type without virginiamycin.

EXAMPLE V

Complementing Antibacterial Activity Screen

Figure 6:
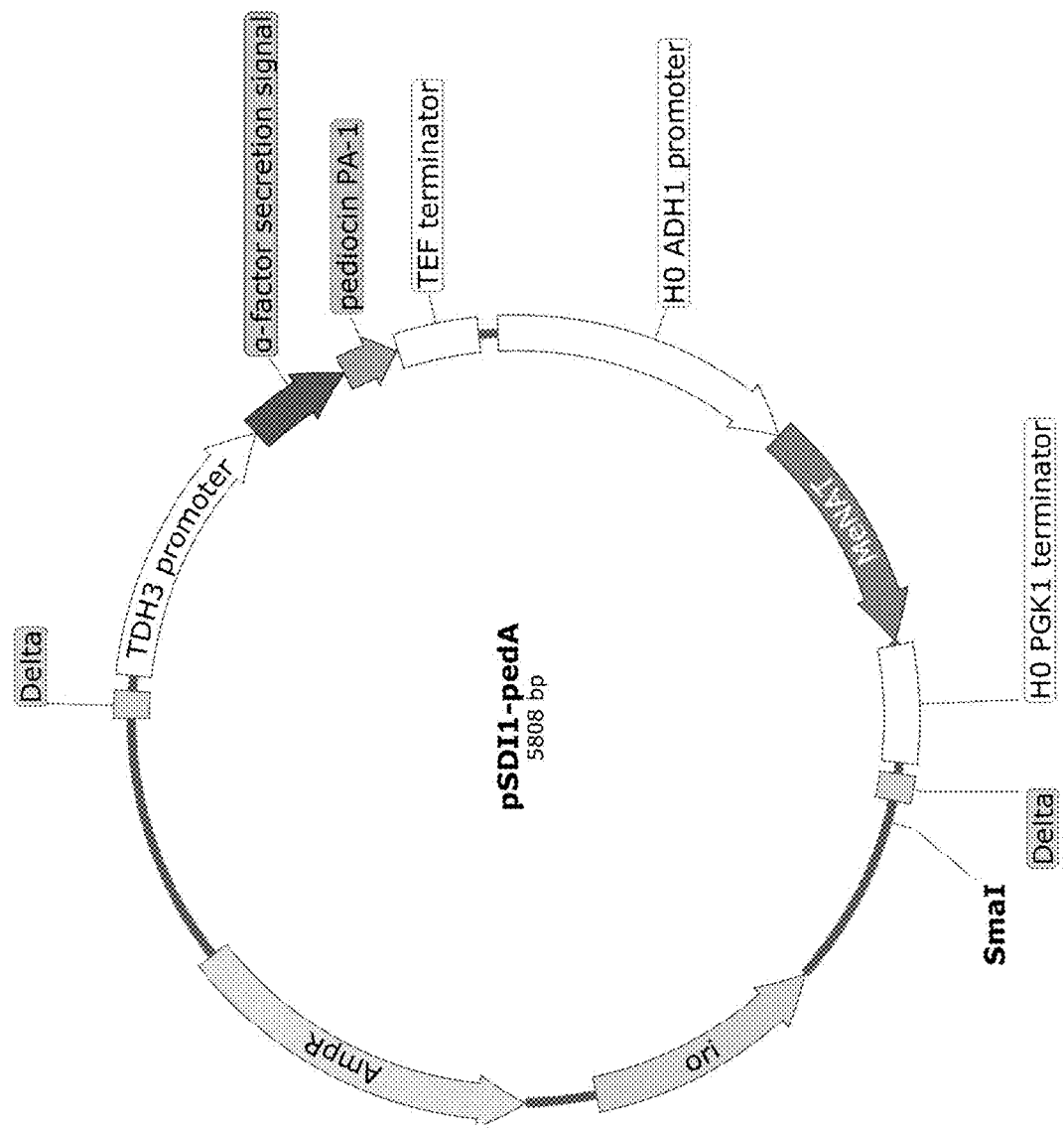
FIG. 6 shows a plasmid map of pSDI1-pedA. pSDI-pedA was used for expression and secretion of pediocin PA-1 in *S. cerevisiae*. Similar plasmids were used to express and secrete different antibacterial peptides by replacing pediocin PA-1 with the peptide of interest. The vector can be linearized by restriction enzyme digestion at the SmaI cut site. H0 *Metschnikowia* sp. ADH1 promoter and PGK1 terminator were used for expression of a modified natMX (MeNAT) to confer resistance to nourseothricin (U.S. Ser. No. 10/435, 721B2). The delta sites were targeted for chromosomal integration.

To test the expression and secretion of antibacterial peptides in *S. cerevisiae*, plasmids were constructed that contain a TDH3 promoter, a mating factor alpha-1 secretion signal with a Kex2 cleavage site followed by an antibacterial peptide, and a TEF1 terminator (FIG. 6). The plasmids contain a nourseothricin resistance gene with an H0 ADH1 promoter and an H0 PGK1 terminator. These elements are flanked by delta integration sites, which are for integrating multiple copies of the cassette into the yeast chromosomes. The plasmid contains a SmaI cut site that can be used for linearization of the plasmid before transformation.

Amino acid sequences for numerous antibacterial peptides, which included 72 bacteriocins, a synthetic peptide (HHC-36), 15 human defensins, a plant antimicrobial peptide and 44 invertebrate antimicrobial peptides, were obtained from BACTIBASE (bactibase.hammamilab.org/main.php), the antimicrobial peptide database (ap-s.unmc.edu/AP/), UniProt (uniprot.org), and various publications. Genes for the antibacterial peptides were synthesized and optimized for *S. cerevisiae* using the GeneOptimizer algorithm provided by ThermoFisher Scientific.

*S. cerevisiae* BY4742 was transformed with the linearized peptide expression cassettes by electroporation and selected on YPD-clonNAT plates. Four colonies from each transformation were grown on YPD plates and tested for antibacterial activity using the soft-agar overlay assay. Soft-agar (MRS media with 0.7% agar) was cooled to 50° C., inoculated with lactic acid bacteria, and poured over the yeast colonies. The lactic acid bacteria/yeast were grown overnight, and the plates were visually inspected for bacterial growth inhibition zones around the yeast colonies. Antibacterial activity was assayed against the lactic acid bacteria *Enterococcus faecium, Lactobacillus delbrueckii, Lactobacillus fermentum, Lactobacillus mucosae, Lactobacillus reuteri, Lactococcus lactis, Pediococcus pentosaceus*, and *Weissella confusa*, which were found as the predominant bacterial species in ethanol plants (Liu et al., *Biotechnol. Biofuels*, 8:132 (2015)), and as well as other lactic acid bacteria, including *Lactobacillus plantarum, Lactobacillus paracasei, Streptococcus thermophilus, Lactobacillus amylovorus, Lactobacillus casei, Leuconostoc mesenteroides* subsp. *mesenteroides, Pediococcus acidilactici, Pediococcus damnosus, Lactobacillus plantarum*, and *Lactobacillus brevis* for certain antibacterial peptides.

Figure 7:
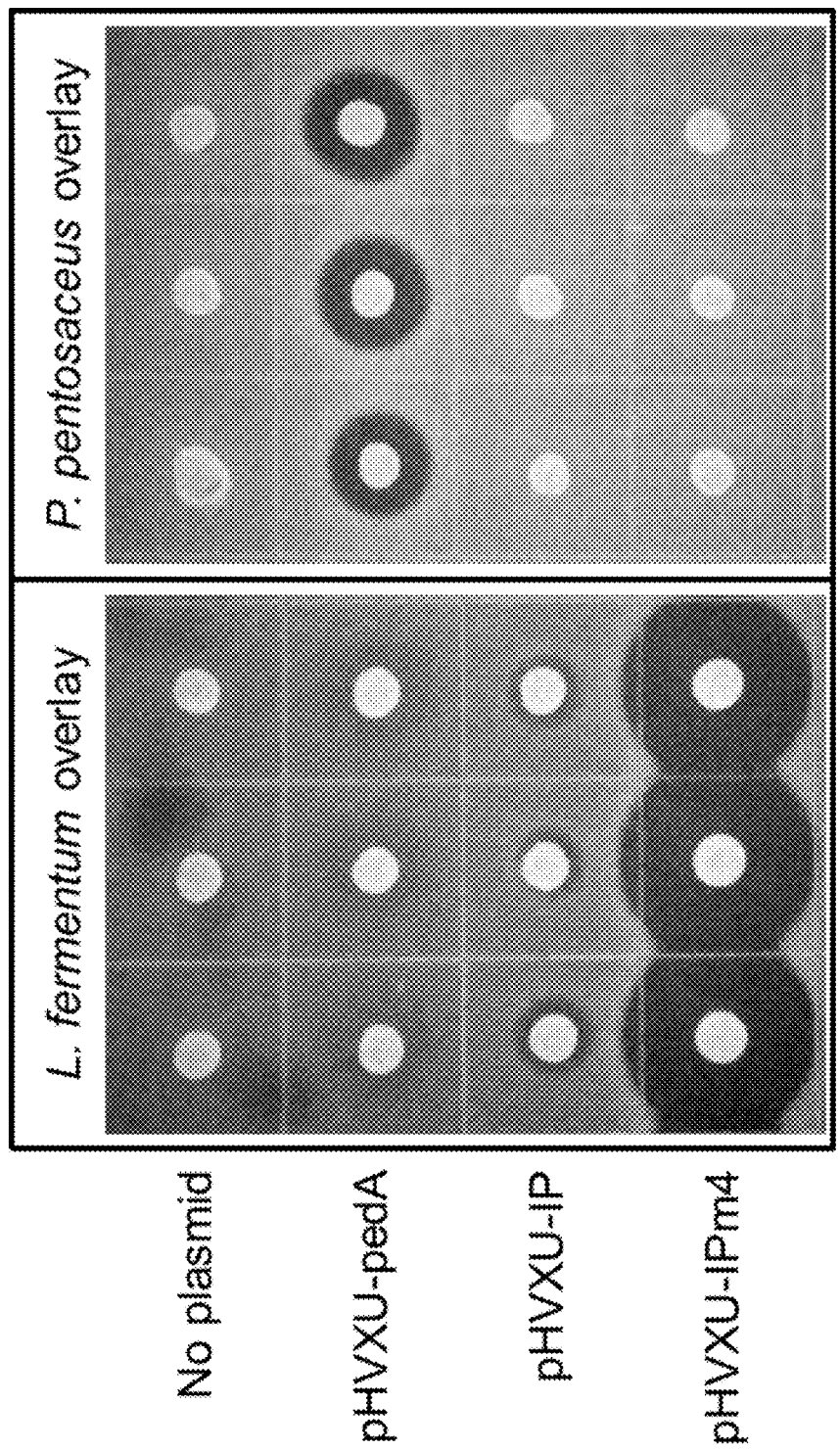
FIG. 7 shows exemplary results of a soft-agar overlay assay of *S. cerevisiae* BY4742 without plasmid, and *S. cerevisiae* BY4742 expressing pediocin PA-1, wild-type persulcatusin, or an engineered persulcatusin with alterations F6L, G9D, R13S, and H14Q. *S. cerevisiae* BY4742 wild-type and 3 colonies each from *S. cerevisiae* BY4742 transformed with plasmids expressing pediocin PA-1 (pHVXU-pedA), wild-type persulcatusin (pHVXU-IP), or engineered persulcatusin (pHVXU-IPm4) were spotted onto YPD agar plates and grown at 30° C. for 1 day. Soft-agar overlays containing *L. fermentum* NCCB 46038 or *P. pentosaceus* NCCB 31016 were poured over the yeast colonies and incubated at 30° C. for 1 day. Growth inhibition zones of *L. fermentum* are observable around *S. cerevisiae* BY4742 expressing wild-type persulcatusin, with significantly bigger zones for the engineered persulcatusin. Growth inhibition zones of *P. pentosaceus* are observable around *S. cerevisiae* BY4742 expressing pediocin PA-1.

Of the antibacterial peptides screened, eight bacteriocins (pediocin PA-1, leucocin C, enterocin A, hiracin JM79, S-Rpediocin, ubericin A, coagulin A, bactofencin A) were discovered to have antibacterial activity against at least 1 of the 9 indicator bacteria used (Table 4). Differences in the levels of inhibition were observed between transformants of the same cassettes, which might have been due to differences in the copy numbers of the cassettes. None of the bacteriocins had antibacterial activity against all the indicator bacteria tested. Moreover, only bactofencin A appeared to have activity outside the antibacterial spectrum of pediocin PA-1, which was determined to include four of the nine indicator bacteria. Surprisingly, the invertebrate peptide, persulcatusin, was identified as having antibacterial activity against two of the nine indicator bacteria that were not inhibited by pediocin PA-1. Moreover, an engineered persulcatusin having alterations F6L, G9D, R13S and H14Q as described in Example III, when similarly assayed for antibacterial activity, showed improved antibacterial activity against several lactic acid bacteria (Table 4 and FIG. 7), especially against *Lactobacillus fermentum* as described in Example III. Pediocin PA-1 and the engineered persulcatusin also showed some antibacterial activity against *Lactobacillus amylovorus* and *Lactobacillus casei*, albeit sometimes weak antibacterial activity. Pediocin PA-1 still further showed antibacterial activity against *Leuconostoc mesenteroides* subsp. *mesenteroides, Lactobacillus delbrueckii* subsp. *delbrueckii, Lactococcus lactis* subsp. *cremoris, Pediococcus acidilactici, Pediococcus damnosus, Lactobacillus plantarum*, and *Lactobacillus brevis*.

TABLE 4

Screening peptide-expressing yeast against lactic acid bacteria.

| Peptides | Lactic acid bacteria | | | | | | | | |
|---|---|---|---|---|---|---|---|---|---|
| | L. reuteri CCUG 32624 | L. fermentum NCCB 46038 | P. pentosaceus NCCB 31016 | E. faecium NCCB 86023 | W. confusa CCUG30113 | W. confusa CCUG30943 | L. mucosae CCUG 43179 | L. lactis NCCB 26066 | L. delbrueckii CCUG 34222 |
| Bacteriocins | | | | | | | | | |
| Pediocin PA-1 | − | − | + | + | − | − | n.d. | + | + |
| Leucocin C | − | − | + | + | − | − | n.d. | + | + |
| Enterocin A | − | − | + | − | − | − | n.d. | + | + |
| Hiracin JM79 | − | − | − | + | − | − | n.d. | − | − |
| S-Rpediocin | − | − | − | + | − | − | n.d. | − | − |
| Ubericin A | − | − | + | − | − | − | n.d. | + | + |
| Coagulin A | − | − | + | + | − | − | n.d. | + | + |
| Bactofencin A | − | + | + | + | − | − | n.d. | + | + |
| Invertebrate peptide | | | | | | | | | |
| Persulcatusin | − | + | − | − | + | − | n.d. | − | − |
| Engineered Persulcatusin | + | + | − | − | + | + | n.d. | − | − |

(+) Inhibition observed, (−) no inhibition observed, and (n.d.) inhibition not determined in the soft-agar overlay assays.

EXAMPLE VI

Alanine Scanning of Pediocin PA-1

In order to to gain insight into each amino acid residue of pediocin PA-1 that would increase the antibacterial activity of pediocin PA-1, an alanine scan of pediocin PA-1 (SEQ ID NO: 36) was conducted in order to generate various pediocin PA-1 variants. The alanine scan methods and plasmid generation procedures were consistent with those described in Example II.

Figure 8:
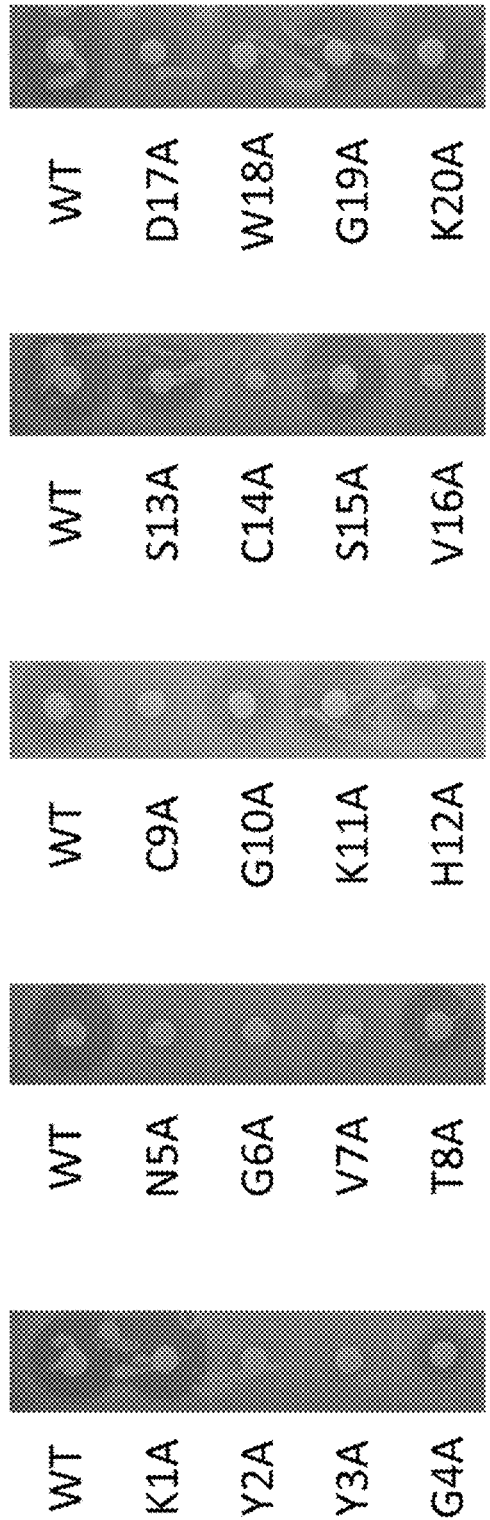
FIG. 8 shows exemplary results of a soft-agar overlay assay of *S. cerevisiae* M2 strain transformed with a plasmid encoding wild-type pediocin PA-1 (WT) or pediocin PA-1 variants from an alanine scan (K1A, Y2A, Y3A, G4A, N5A, G6A, V7A, T8A, C9A, G10A, K11A, H12A, S13A, C14A, S15A, V16A, D17A, W18A, G19A, K20A, T22A, T23A, C24A, I25A, I26A, I26A, N27A, N28A, G29A, M31A, W33A, T35A, G36A, G37A, H38A, Q39A, G40A, N41A, H42A, K43A or C44A). Strains were spotted onto YPD agar plates and grown at 30° C. for 1 day. Soft-agar overlays containing *P. pentosaceus* NCCB 31016 were poured over the yeast colonies and incubated at 30° C. for 1 day. Growth inhibition zones of *P. pentosaceus* were observable around *S. cerevisiae* expressing several of the pediocin PA-1 variants, including variants with an S13A, S15A, G19A, K20A, or T22A mutation, with the K1A mutation having the largest halo compared to wild-type pediocin PA-1.
Figure 8:
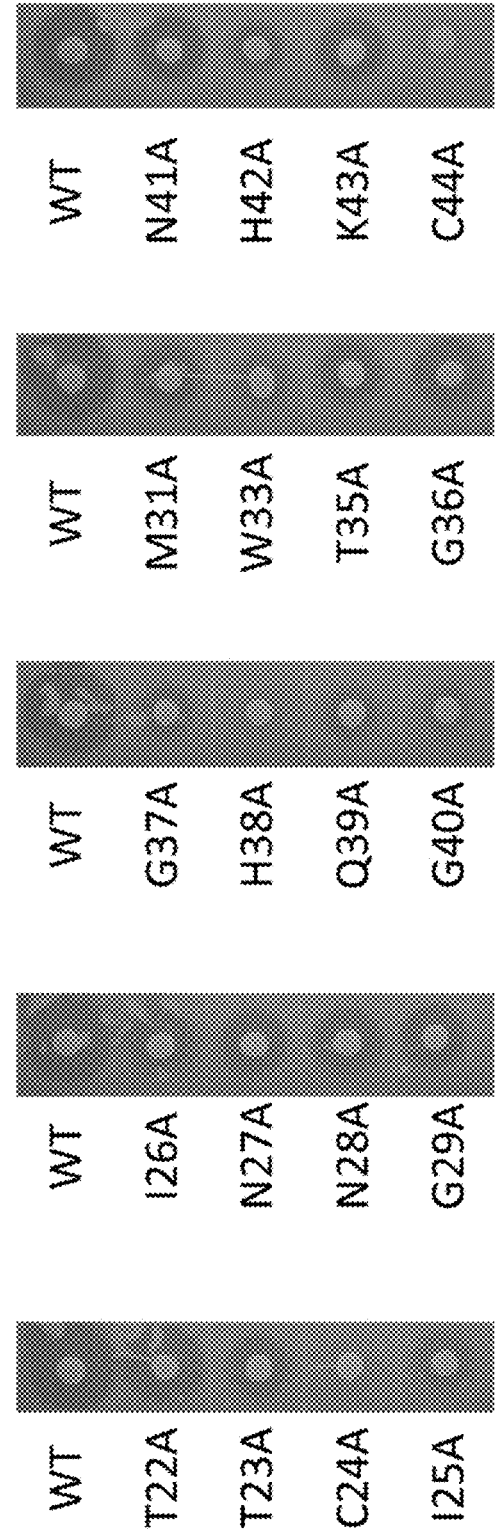
Figure 9:
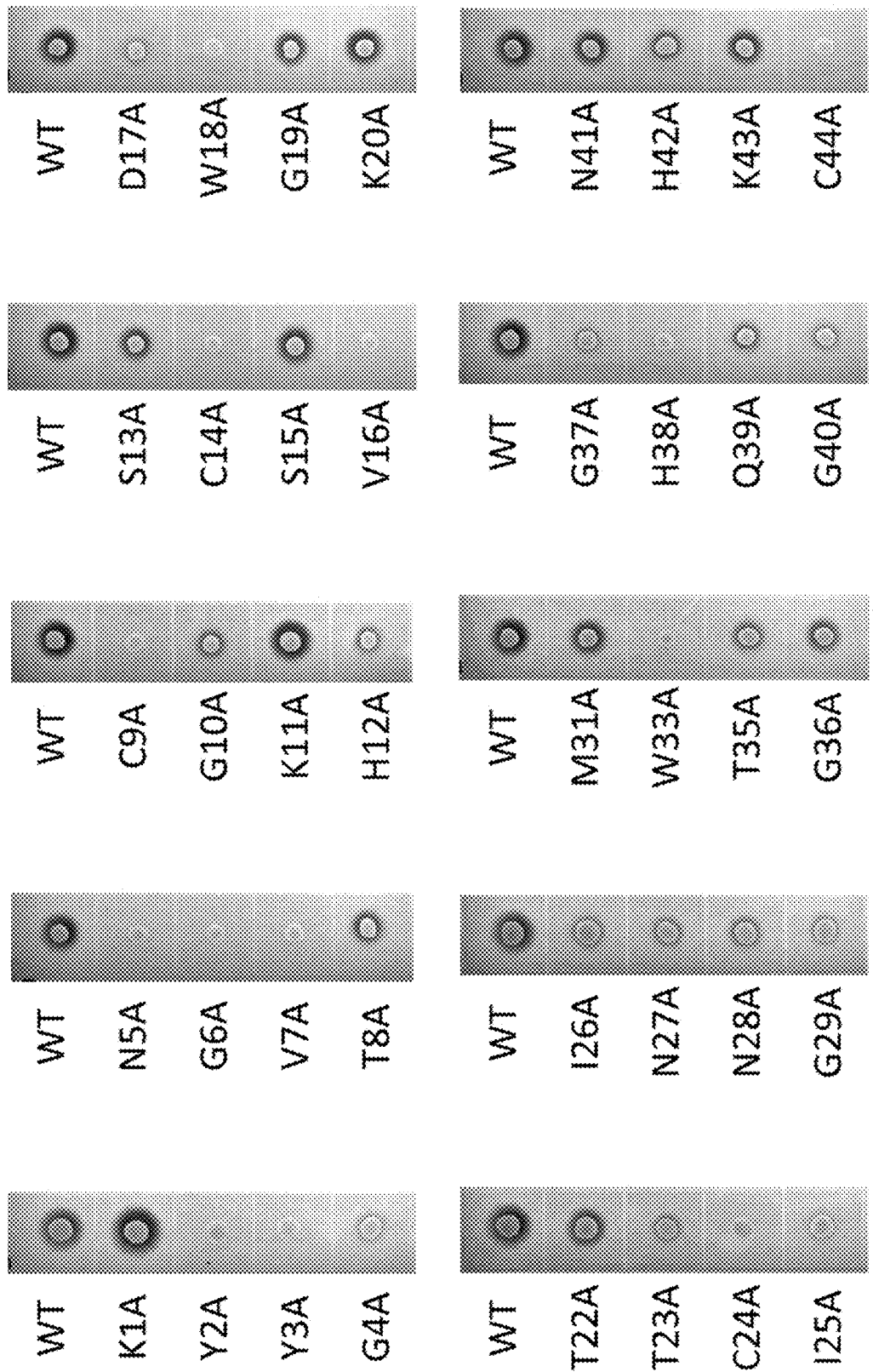
FIG. 9 shows exemplary results of a soft-agar overlay assay of *S. cerevisiae* M2 strain transformed with a plasmid encoding wild-type pediocin PA-1 (WT) or engineered pediocin PA-1 variants from an alanine scan (K1A, Y2A, Y3A, G4A, N5A, G6A, V7A, T8A, C9A, G10A, K11A, H12A, S13A, C14A, S15A, V16A, D17A, W18A, G19A, K20A, T22A, T23A, C24A, I25A, I26A, I26A, N27A, N28A, G29A, M31A, W33A, T35A, G36A, G37A, H38A, Q39A, G40A, N41A, H42A, K43A or C44A). Strains were spotted onto YPD agar plates and grown at 30° C. for 1 day. Soft-agar overlays containing *L. delbrueckii* CCUG 34222T were poured over the yeast colonies and incubated at 30° C. for 1 day. Growth inhibition zones of *L. delbrueckii* were observable around *S. cerevisiae* expressing several of the pediocin PA-1 variants, including variants with an S13A, S15A, G19A, K20A, or T22A mutation, with the K1A mutation having the largest halo compared to wild-type pediocin PA-1.

An *S. cerevisiae* M2 strain having ura3Δ/ura3Δ mutations were transformed with the plasmids encoding the pediocin PA-1 variants. Six transformants for each variant encoding plasmid were tested for antibacterial activity using a soft-agar overlay assay as described in Example II with *P. pentosaceus* or *L. delbrueckii*. Exemplary results of these overlay assays are shown in FIG. 8 for *P. pentosaceous* and FIG. 9 for *L. delbrueckii*. The pediocin PA-1 variant having a K1A mutation appeared to have the largest halos compared to wild-type pediocin PA-1. Pediocin PA-1 variants with similar size halos to wild-type pediocin PA-1 included pediocin PA-1 variants having a S13A, S15A, G19A, K20A, and T22A mutation.

Figure 10:
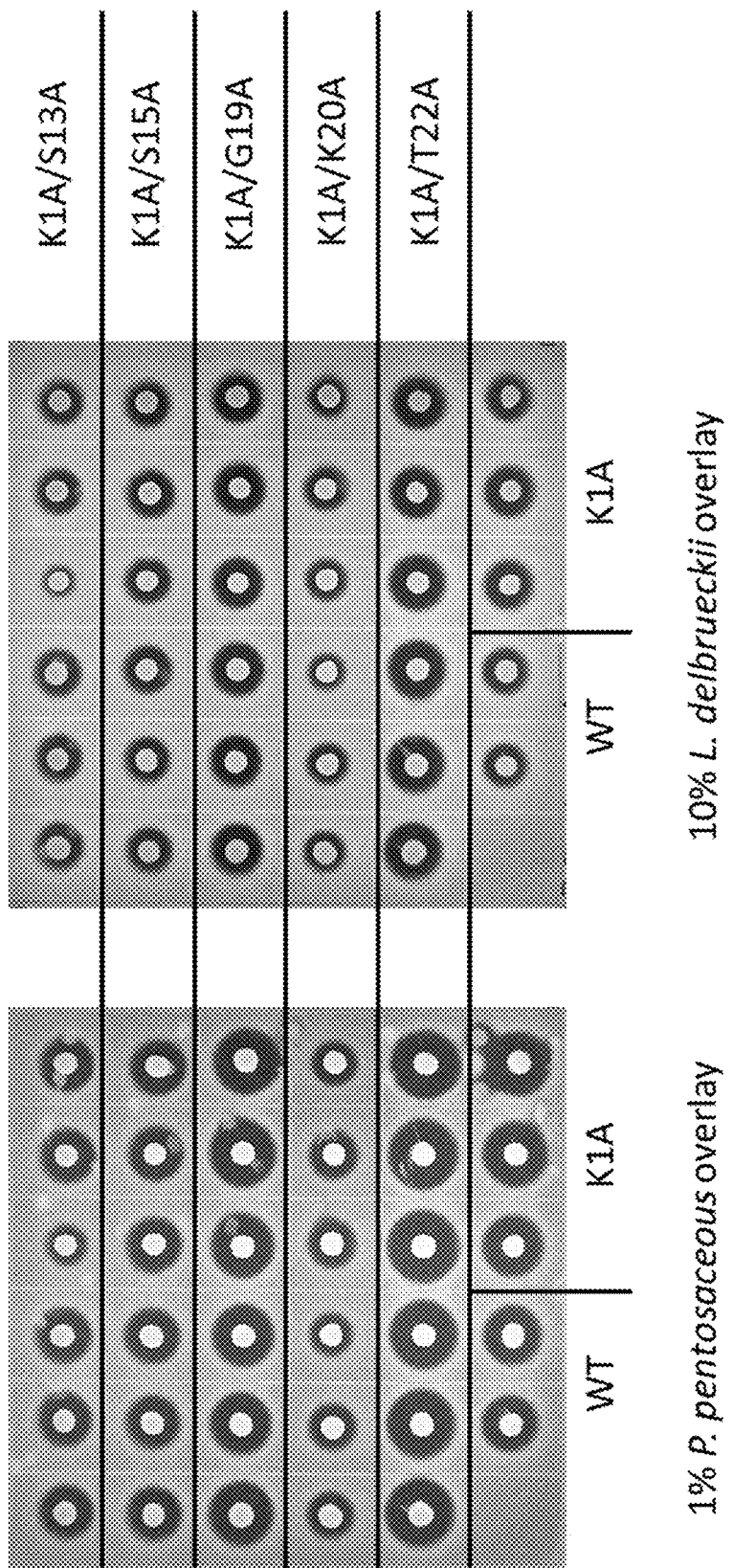
FIG. 10 shows exemplary results of a soft-agar overlay assay of *S. cerevisiae* M2 strain transformed with a plasmid encoding engineered pediocin PA-1 variants having double mutations (K1A/S13A, K1A/S15A, K1A/G19A, K1A/K20A or K1A and T22A). Strains were spotted onto YPD agar plates and grown at 30° C. for 1 day. Soft-agar overlays containing *P. pentosaceus* NCCB 31016 or *L. delbrueckii* CCUG 34222T were poured over the yeast colonies and incubated at 30° C. for 1 day. Growth inhibition zones of *P. pentosaceus* and *L. delbrueckii* were observable around *S. cerevisiae* expressing any of the pediocin PA-1 double mutations, but pediocin double variant K1A/T22A appeared to show the largest halo compared to wild-type and the pediocin variant K1A.

Based on these results, several pediocin PA-1 variants containing double alanine mutations (pediocin double variants) were generated and transformed into an M2 strain having ura3Δ/ura3Δ mutations. These pediocin double variants included pediocin PA-1 (SEQ ID NO: 36) having K1A/S13A, K1A/S15A, K1A/G19A, K1A/K20A, or K1A/T22A mutations. The double mutants were generated by performing PCR with the pediocin S13A, S15A, G19A, K20A, or T22A plasmids as the DNA template, a primer that inserted the K1A mutation and overlaps the 5' end of pediocin and the MFα1 region, and a primer that overlaps the 3' end of pediocin and the AgTEFt region. This was cloned into the linearized vector obtained by using PCR to amplify pHVXU-mRUBY using primers complementary to the MFα1 and AgTEFt regions followed by DpnI digestion and gel purification. These pediocin double variants were tested for antibacterial activity using the same soft-agar overlay assay described in Example II with *P. pentosaceous* or *L. delbrueckii*. Exemplary results of these overlay assays are shown in FIG. 10. Pediocin double variant K1A/T22A appeared to show the largest halo compared to wild-type and the pediocin variant K1A.

Several pediocin variants containing triple alanine mutations (pediocin triple variants) were generated as described above and assayed for antibacterial activity using the same soft-agar overlay assay described in Example II. These pediocin triple variants included pediocin PA-1 (SEQ ID NO: 36) having K1A/T22A/S13A, K1A/T22A/S15A, or K1A/T22A/G19A. None of the pediocin triple variants appeared to further increase activity beyond that which was observed for pediocin double variant K1A/T22A.

EXAMPLE VII

Random Mutagenesis of Pediocin PA-1

In order to identify further alterations that would increase the antibacterial activity of pediocin PA-1, pediocin PA-1 was randomly mutated and transformed into *S. cerevisiae* M2 strain containing ura3Δ/ura3Δ, similarly to the method described in Example III for generating engineered persulcatusin variants. An *S. cerevisiae* M2 strain having ura3Δ/ura3Δ mutations were transformed with the plasmids encoding the pediocin PA-1 variants. Transformants were tested for antibacterial activity using a soft-agar overlay assay as described in Example II with *P. pentosaceous* or *L. delbrueckii*. Many transformants with large inhibition zones were identified, but further experiments showed that many of the large inhibition zones may have been due to a contamination with a different bacteriocin.

Figure 11:
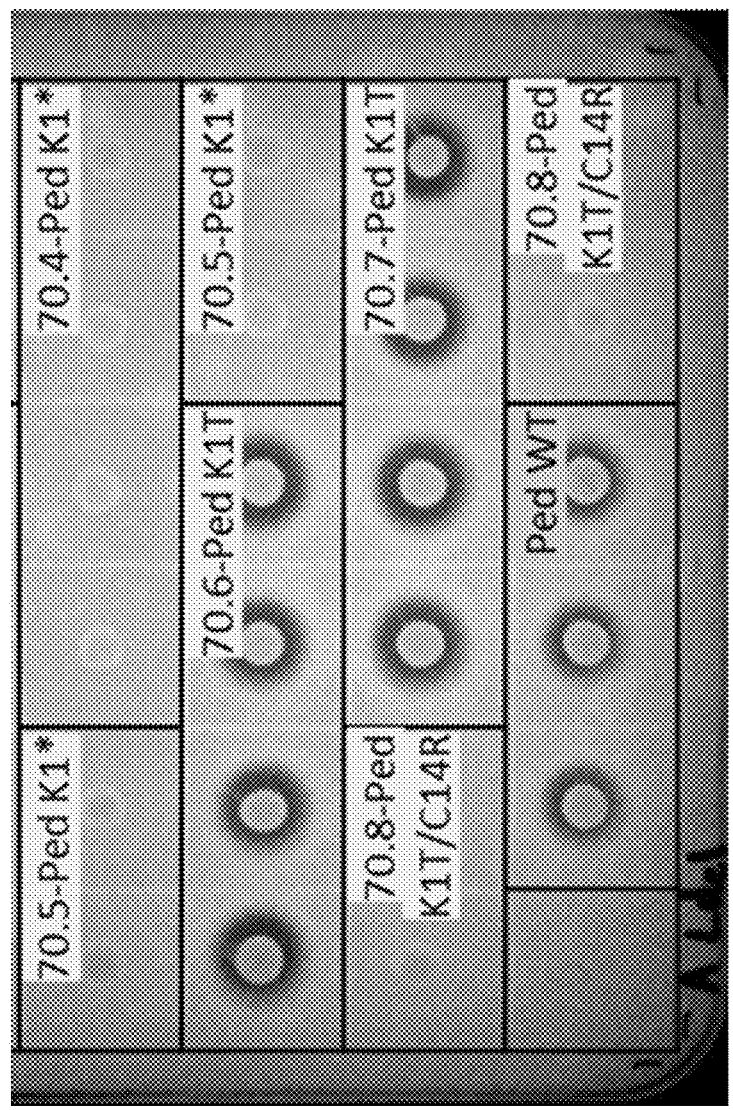
FIG. 11 shows exemplary results of a soft-agar overlay assay of *S. cerevisiae* M2 strain transformed with a plasmid encoding wild-type pediocin PA-1 (WT) or engineered pediocin PA-1 variants having mutations generated by random mutagenesis (K1T or K1T/C14R). K1* represents K1Stop (a nonsense mutation). Strains were spotted onto YPD agar plates and grown at 30° C. for 1 day. Soft-agar overlays containing *L. delbrueckii* CCUG 34222T were poured over the yeast colonies and incubated at 30° C. for 1 day. Growth inhibition zones were observable around *S. cerevisiae* expressing the pediocin PA-1 K1T mutation.

Nevertheless, from the transformants with the largest inhibition zones (#70 & #91), following PCR amplification, sequencing and recloning, eight plasmids were cloned from each transformant, retransformed into an *S. cerevisiae* M2 strain having ura3Δ/ura3Δ mutations and four transformants for each plasmid were tested for antibacterial activity using a soft-agar overlay assay as described in Example II with *L. delbrueckii*. Exemplary results of these assays are shown in FIG. 11. A pediocin PA-1 variant having a KU' mutation appeared to have a slightly bigger halo than wild-type pediocin PA-1, whereas a pediocin PA-1 variant having a K1T/C14R double mutation showed no inhibition zone.

Example VIII

Combined Inhibition with Engineered Persulcatusin and Engineered Pediocin PA-1

Figure 12:
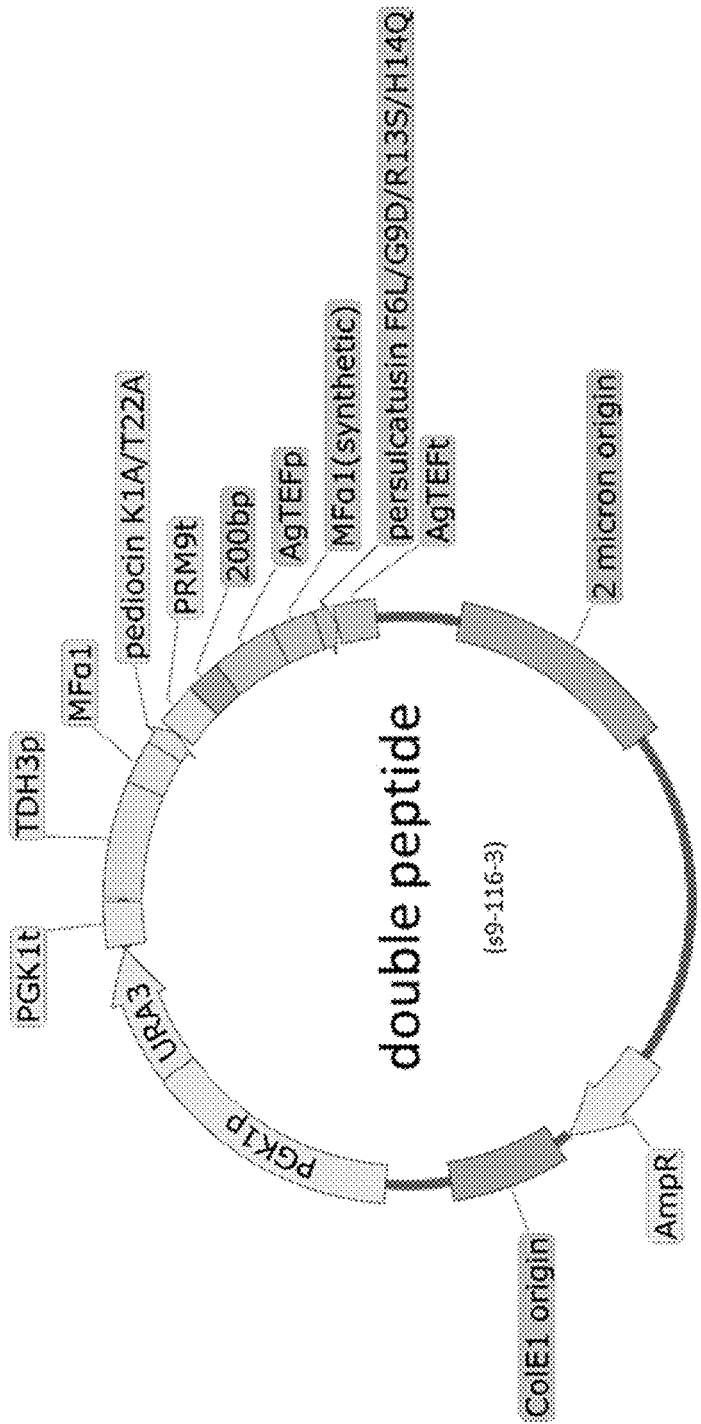
FIG. 12 shows a plasmid map of pHVXU-mRUBY containing expression cassettes for two engineered peptides-persulcatusin variant having F6L/G9D/R13S/H14Q mutations and a pediocin PA-1 variant having K1A/T22A mutations ("double peptide" plasmid). The pediocin and persulcatusin cassettes are separated by 200 bp of random sequence. The α-factor secretion signals preceding the pediocin and persulcatusin variants are natural and codon-optimized sequences, respectively. Expression of secreted pediocin and persulcatusin variants were controlled by the *S. cerevisiae* TDH3 promoter/PRM9 terminator and the *Ashbya gossypii* TEF promoter/TEF terminator, respectively.

In order to evaluate the antibacterial activity of combining an engineered persulcatusin with an engineered pediocin PA-1, a "double peptide" plasmid was generated that encoded a persulcatusin variant having F6L/G9D/R13S/H14Q mutations (as identified in Example V) and a pediocin PA-1 variant having K1A/T22A mutations (identified in Example VI). A schematic depiction of the double peptide plasmid is provided in FIG. 12.

Figure 13:
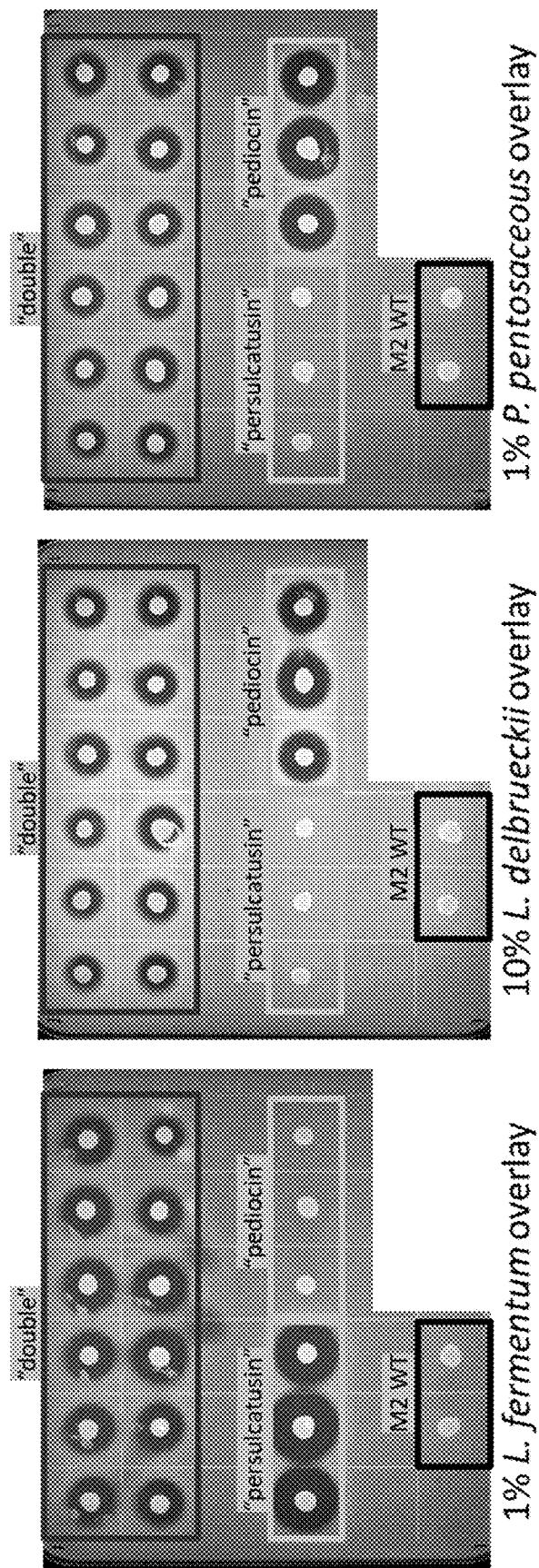
FIG. 13 shows exemplary results of a soft-agar overlay assay of *S. cerevisiae* M2 strain transformed with the plasmid of FIG. 12 compared to *S. cerevisiae* M2 strain itself, or *S. cerevisiae* M2 strain transformed with plasmids encoding persulcatusin F6L/G9D/R13S/H14Q or pediocin PA-1 K1A/T22A alone. Strains were spotted onto YPD agar plates and grown at 30° C. for 1 day. Soft-agar overlays containing *L. fermentum* NCCB 46038, *L. delbrueckii* CCUG 34222T or *P. pentosaceus* NCCB 31016 were poured over the yeast colonies and incubated at 30° C. for 1 day. Growth inhibition zones were observable from the *S. cerevisiae* M2 strain transformed with the plasmid of FIG. 12 across the three different lactic acid bacteria.

An S. cerevisiae M2 strain having ura3Δ/ura3Δ mutations was transformed with the double peptide plasmid and the resulting transformants were tested for antibacterial activity using a soft-agar overlay assay as described in Example II with L. fermentum, L. delbrueckii or P. pentosaceous. Exemplary results of these assays are shown in FIG. 13. Expression of both an engineered persulcatusin with an engineered pediocin PA-1 showed antibacterial activity across the three different lactic acid bacteria that were tested, which was an improved diversity of the antibacterial activity seen for the persulcatusin variant having F6L/G9D/R13S/H14Q or pediocin PA-1 variant having K1A/T22A alone.

Example IX

Fermentation with Engineered Pediocin PA-1

In order to assess the antibacterial activity of the engineered pediocin PA-1 described in Example VI, mock fermentations were conducted using an S. cerevisiae M2 strain having ura3Δ/ura3Δ mutations transformed with plasmids encoding pediocin PA-1 wild-type and variants having K1A, K1A/T22A, or K1 T mutations (identified in Example VI). The resulting strains, M2-pPedA, M2-pPedA-K1A, M2-pPedA-K1A/T22A, and M2-pPedA-K1T, were screened for antibacterial activity using the soft-agar overlay assay as described in Example II.

Figure 14A:
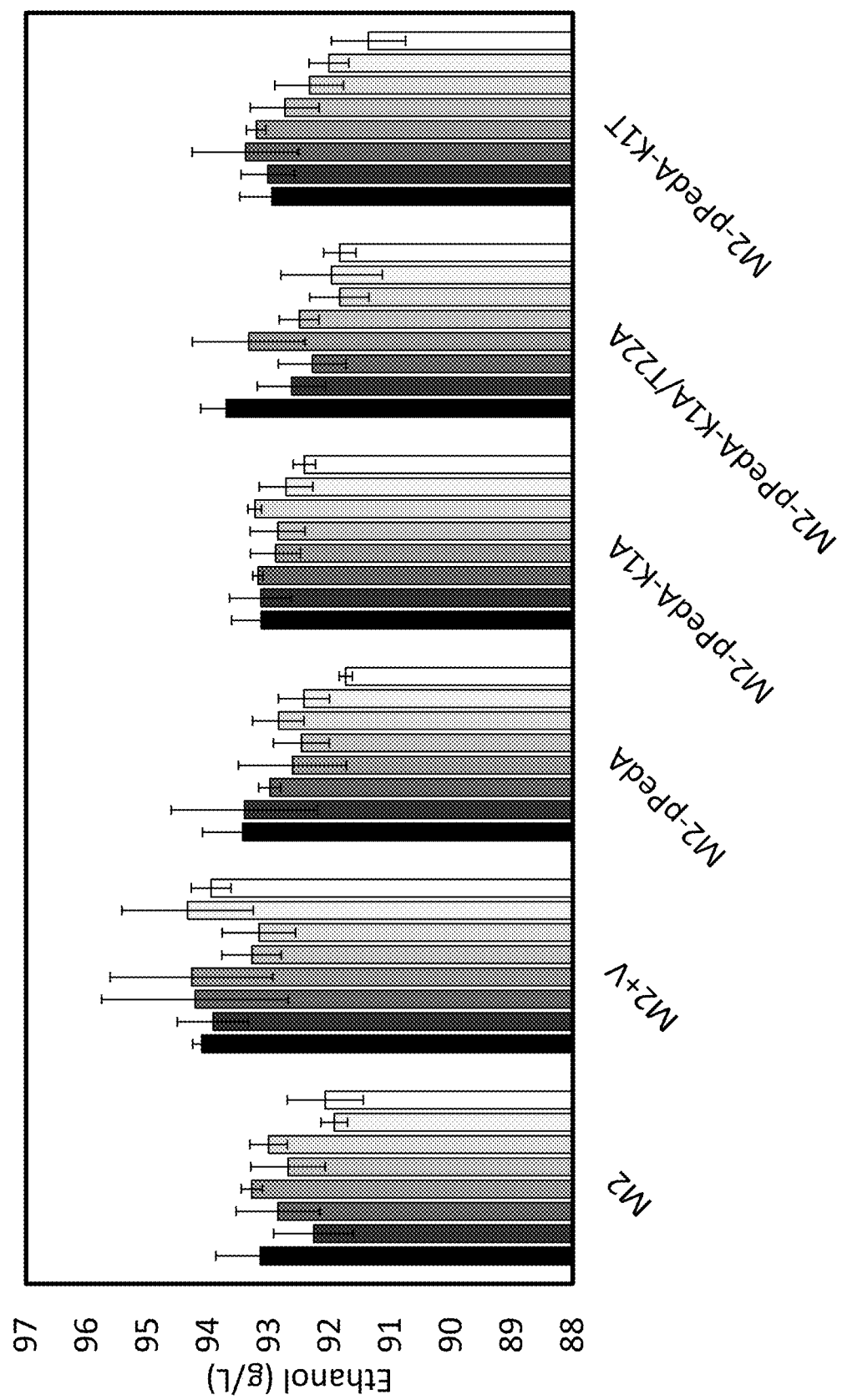
FIG. 14A-14D show exemplary results for fermentations with M2 wild-type, M2-pPedA, M2-pPedA-K1A, M2-pPedA-K1A/T22A, and M2-pPedA-K1T expressing wild-type and engineered pediocin having the mutations K1A, K1A/T22A, or K1T from plasmids with varying levels of *L. delbrueckii* contamination. Filtered corn mash supplemented with 1.2 g/L ammonium sulfate was inoculated with M2, M2-pPedA, M2-pPedA-K1A, M2-pPedA- K1A/T22A, and M2-pPedA-K1T to an $OD_{600}=1$. M2+V was supplemented with 2 mg/L virginiamycin. Fermentations were not contaminated (black bars) or artificially contaminated with *L. delbrueckii* to $OD_{600}$ levels of 0.00005, 0.00025, 0.0005, 0.0025, 0.005, 0.025, and 0.05 (increasing levels represented by progressively lighter bars). After 72 hours, levels of ethanol (FIG. 14A), glucose (FIG. 14B), lactic acid (FIG. 14C), and acetic acid (FIG. 14D) were determined by HPLC. Fermentations were performed in triplicate and the error bars represent standard deviation.
Figure 14B:
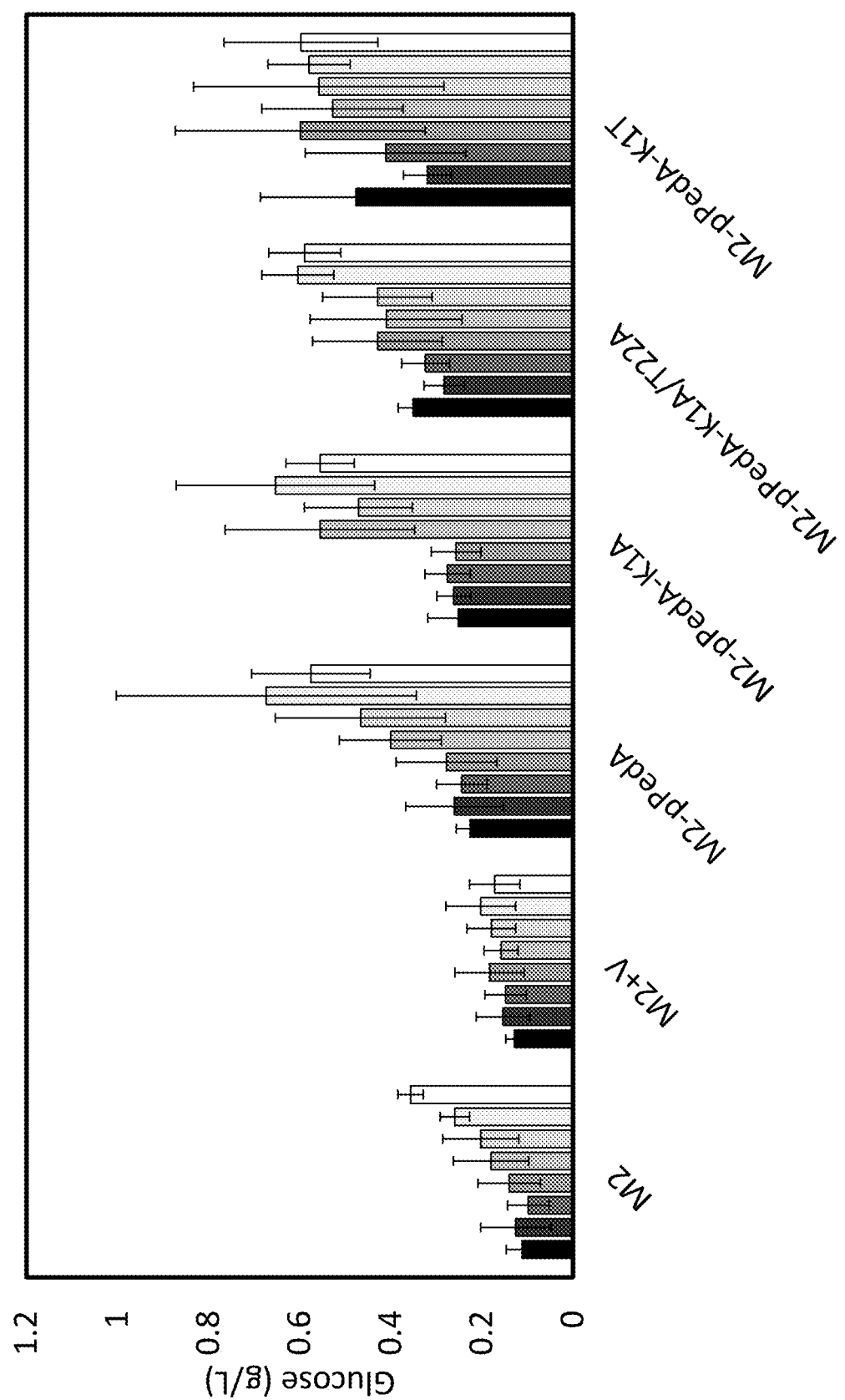
Figure 14C:
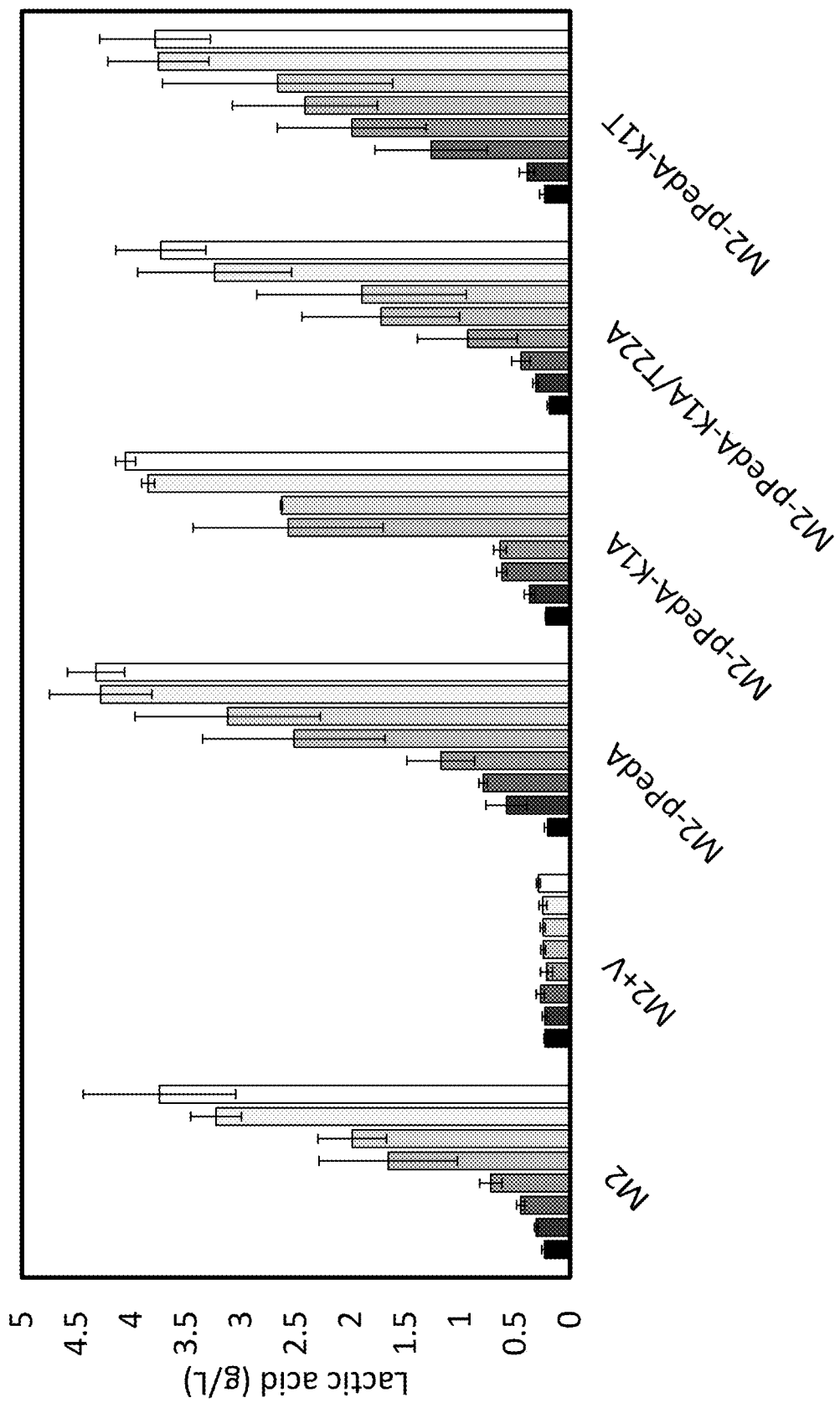
Figure 14D:
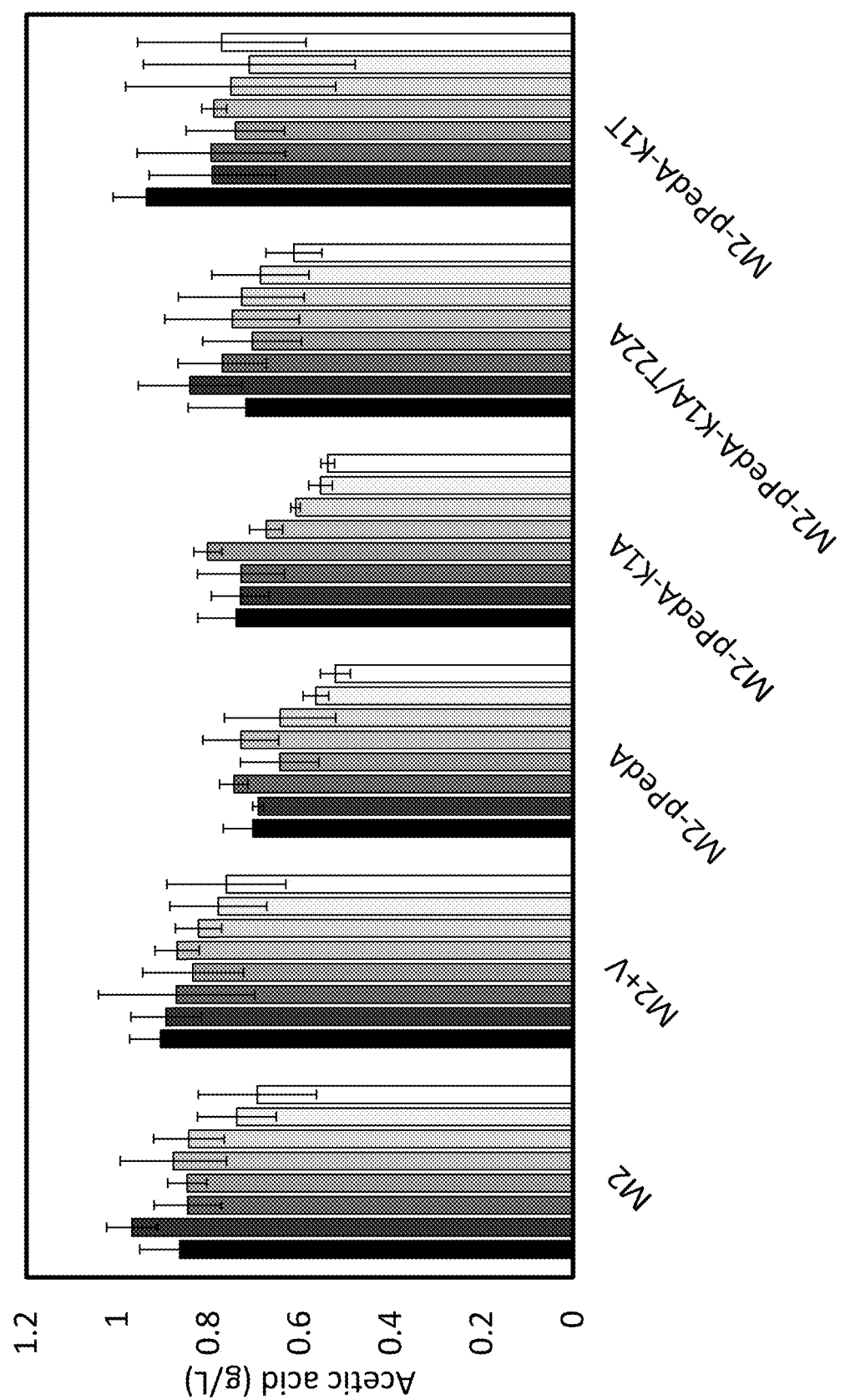
Figure 15A:
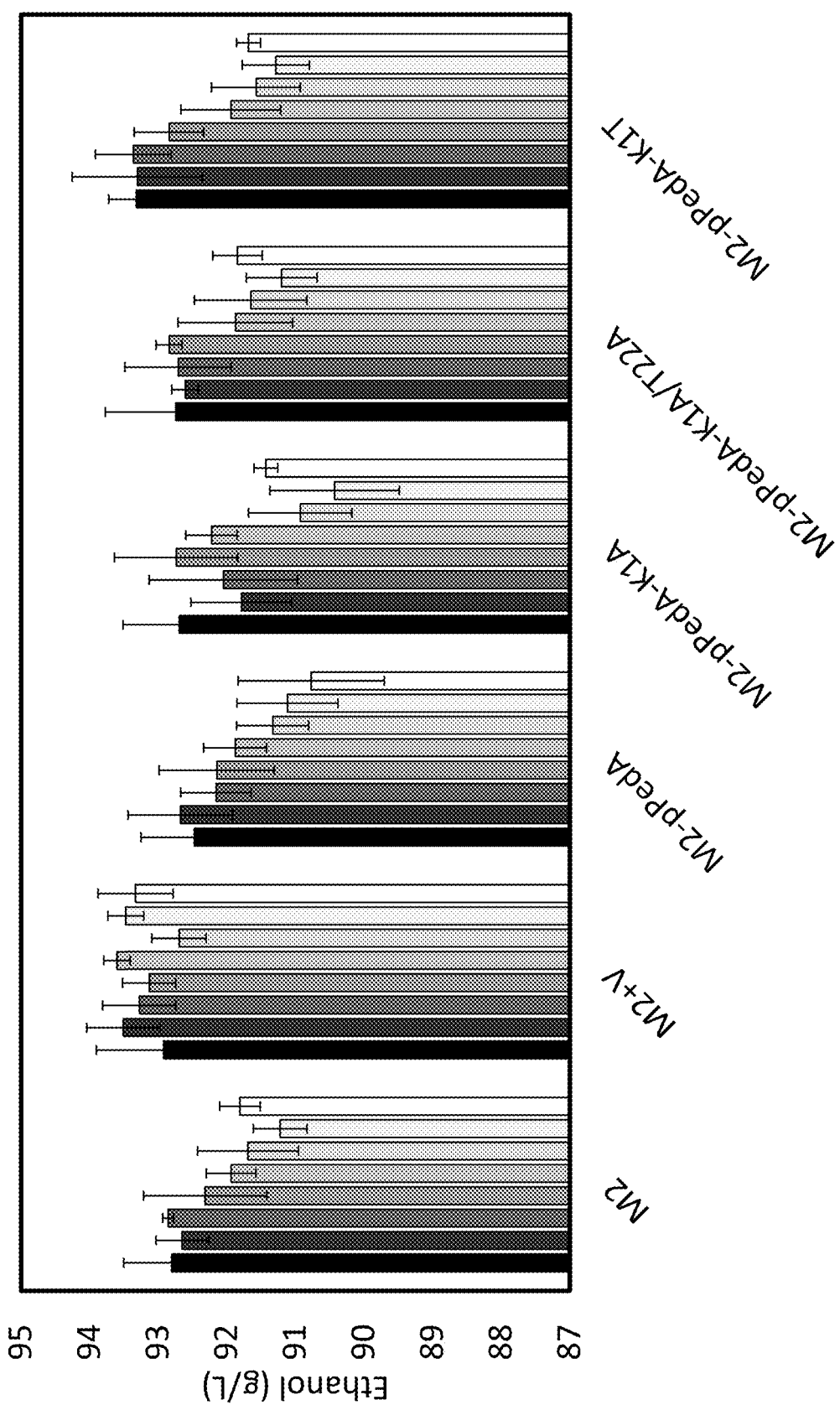
FIG. 15A-15D show exemplary results for fermentations with M2 wild-type, M2-pPedA, M2-pPedA-K1A, M2-pPedA-K1A/T22A, and M2-pPedA-K1T expressing wild-type and engineered pediocin having the mutations K1A, K1A/T22A, or K1LT from plasmids with varying levels of *P. pentosaceus* contamination. Filtered corn mash supplemented with 1.2 g/L ammonium sulfate was inoculated with M2, M2-pPedA, M2-pPedA-K1A, M2-pPedA-K1A/T22A, and M2-pPedA-K1T to an $OD_{600}=1$. M2+V was supplemented with 2 mg/L virginiamycin. Fermentations were not contaminated (black bars) or artificially contaminated with *P. pentosaceus* to $OD_{600}$ levels of 0.00005, 0.00025, 0.0005, 0.0025, 0.005, 0.025, and 0.05 (increasing levels represented by progressively lighter bars). After 72 hours, levels of ethanol (FIG. 15A), glucose (FIG. 15B), lactic acid (FIG. 15C), and acetic acid (FIG. 15D) were determined by HPLC. Fermentations were performed in triplicate and the error bars represent standard deviation.
Figure 15B:
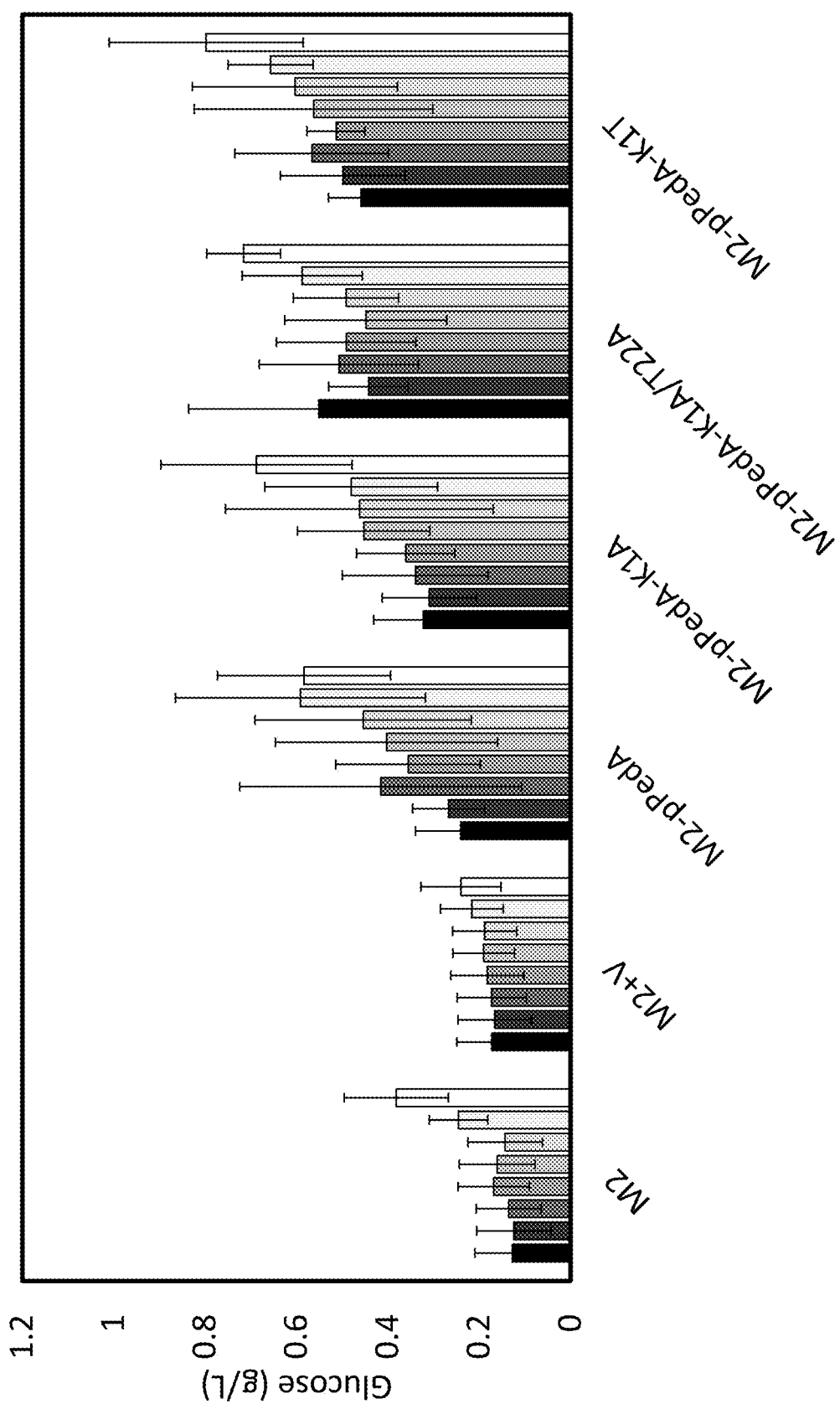
Figure 15C:
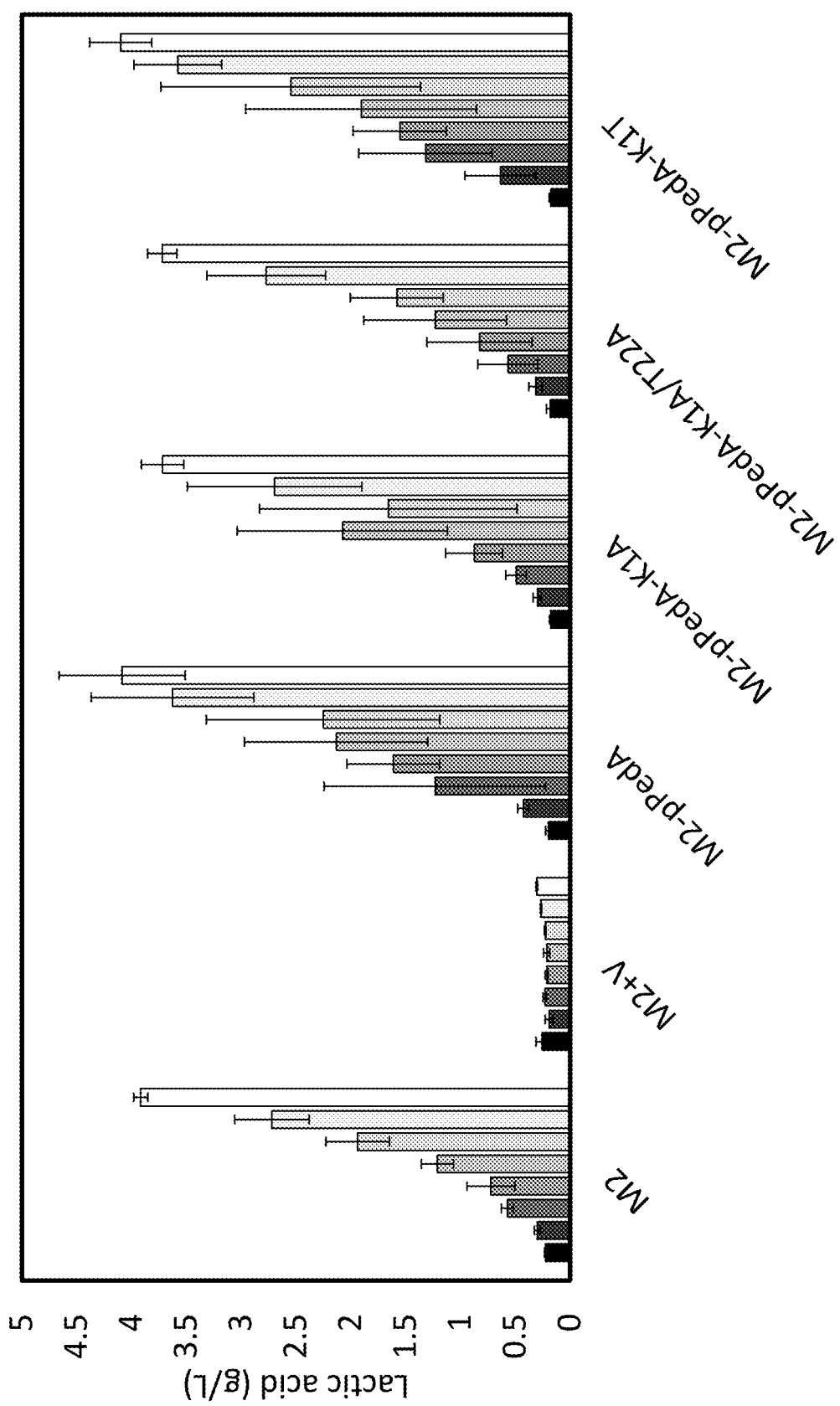
Figure 15D:
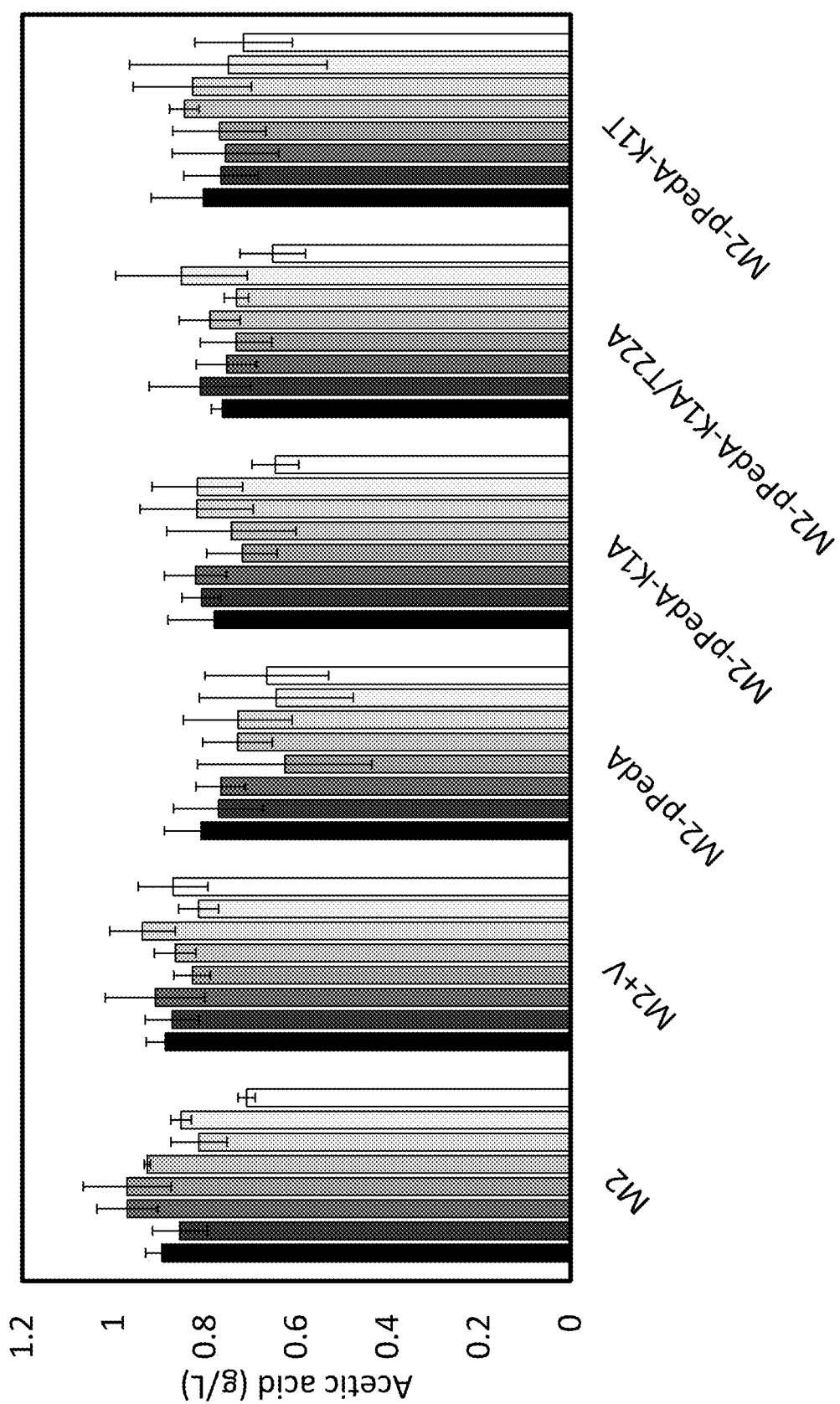

Small-scale mock ethanol fermentations were carried out similar to those described Example IV, but were artificially contaminated with L. delbrueckii or P. pentosaceus instead of L. fermentum. M2 wild-type with and without virginiamycin, M2-pPedA, M2-pPedA-K1A, M2-pPedA-K1A/T22A, and M2-pPedA-K1T were compared (FIGS. 14A-14D, 15A-15D). L. delbrueckii or P. pentosaceus contamination at the highest levels appeared to reduce ethanol yield and increase residual glucose in the samples without virginiamycin (FIGS. 14A-14B, 15A-15B). Increasing levels of L. delbrueckii or P. pentosaceus contamination resulted in increasing levels of lactic acid production in the samples without virginiamycin (FIG. 14C, 15C). Virginiamycin was effective at preventing the lactic acid production by L. delbrueckii and P. pentosaceus at all levels of contamination tested. The pediocin-expressing strains were not effective at completely preventing the lactic acid production by L. delbrueckii or P. pentosaceus. However, less lactic acid was observed with M2-pPedA-K1A/T22A compared to M2-pPedA and M2-pPedA-K1T. In fermentations contaminated with P. pentosaceus, less lactic acid was also observed with M2-pPedA-K1A compared to M2-pPedA or M2-pPedA-K1T. Increasing levels of L. delbrueckii or P. pentosaceus contamination did not lead to increasing levels of acetic acid production, as observed with L. fermentum contamination (FIG. 14D, 15D). Higher amounts of acetic acid were observed in fermentations with M2 with and without virginiamycin compared to the pediocin-expressing strains.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An engineered persulcatusin comprising a variant of the amino acid sequence of SEQ ID NO: 1, wherein the variant amino acid sequence comprises one or more amino acid substitutions at positions selected from F6, N7, G9, R13, H14, R16, 118, R20, R21, A26, L28, F29, and R38 of SEQ ID NO: 1.

2. The engineered persulcatusin of claim 1, wherein the one or more amino acid substitutions are selected from F6A, F6L, F65, F6V, N7D, G9D, R13A, R13S, H14F, H14Q, R16A, R16G, R16K, R16S, 118F, 118N, 118V, R20A, R20K, R20S, R20T, R21A, R21G, R21S, A26D, L28A, L28M, F29A, F29V, and R38A.

3. The engineered persulcatusin of claim 2, wherein the engineered persulcatusin comprises at least two, at least three, or at least four of said amino acid substitutions.

4. The engineered persulcatusin of claim 3, wherein the at least four amino acid substitutions are F6L, G9D, R13S and H140.

5. The engineered persulcatusin of claim 1, wherein the engineered persulcatusin comprises an amino acid sequence selected from SEQ ID NOS: 2-35.

6. The engineered persulcatusin of claim 1, wherein the engineered persulcatusin is fused to a secretion signal peptide.

7. A culture medium comprising the engineered persulcatusin of claim 1.

8. The engineered persulcatusin of claim 4, wherein the engineered persulcatusin having the F6L, G9D, R13S and H14Q amino acid substitutions has antibacterial activity against *Lactobacillus reuteri, Weissella confusa, Lactobacillus fermentum, Lactobacillus amylovorus,* and *Lactobacillus casei.*

9. The engineered persulcatusin of claim 2, wherein the engineered persulcatusin with the amino acid substitution F6A, R13A, R13S, R16A, R20A, R21A, R21G, A26D, L28A, F29A or R38A has antibacterial activity against *Lactobacillus fermentum.*

10. The engineered persulcatusin of claim 2, wherein the engineered persulcatusin with two, three or four of the amino acid substitutions has antibacterial activity against *Lactobacillus fermentum.*

11. A method of culturing a yeast comprising culturing cells of the yeast in the presence of the engineered persulcatusin of claim 1.

12. The method of culturing of claim 11, wherein the culturing of the yeast is by a fermentation process.

13. A method of inhibiting the growth of a contaminant lactic acid bacterium in a yeast culture comprising culturing a yeast in the presence of the engineered persulcatusin of claim 2.

14. The method of claim 13, wherein the yeast culture is a commercial yeast culture.

\* \* \* \* \*

UNITED STATES PATENT AND TRADEMARK OFFICE
CERTIFICATE OF CORRECTION

PATENT NO. : 11,788,053 B2
APPLICATION NO. : 17/347413
DATED : October 17, 2023
INVENTOR(S) : Steve Good-Sung Wong and Hendrik Jurgens Jansen Van Vuuren It is certified that error appears in the above-identified patent and that said Letters Patent is hereby corrected as shown below:

In the Claims

Column 109, Line 42, delete "118" and replace with --I18--

Column 109, Line 46, delete "F65" and replace with --F6S--

Column 109, Line 47, delete "118F, 118N, 118V," and replace with --I18F, I18N, I18V,--

Column 109, Line 48, delete "R2OK" and replace with --R20K--

Column 109, Line 55, delete "H140" and replace with --H14Q--

Signed and Sealed this
Fourth Day of June, 2024

Katherine Kelly Vidal
*Director of the United States Patent and Trademark Office*